(12) United States Patent
Coe et al.

(10) Patent No.: US 7,205,300 B2
(45) Date of Patent: *Apr. 17, 2007

(54) ARYL FUSED AZAPOLYCYCLIC COMPOUNDS

(75) Inventors: Jotham Wadsworth Coe, Niantic, CT (US); Paige Roanne Palmer Brooks, North Stonington, CT (US)

(73) Assignee: Pfizer Inc, New York, NY (US)

( * ) Notice: Subject to any disclaimer, the term of this patent is extended or adjusted under 35 U.S.C. 154(b) by 378 days.

This patent is subject to a terminal disclaimer.

(21) Appl. No.: 10/336,508

(22) Filed: Jan. 3, 2003

(65) Prior Publication Data

US 2003/0130261 A1 Jul. 10, 2003

Related U.S. Application Data

(63) Continuation of application No. 09/514,002, filed on Feb. 25, 2000, now Pat. No. 6,605,610, which is a continuation-in-part of application No. 09/402,010, filed as application No. PCT/IB98/01813 on Nov. 13, 1998, now Pat. No. 6,410,550.

(60) Provisional application No. 60/070,245, filed on Dec. 31, 1997.

(51) Int. Cl.
*A61P 1/00* (2006.01)
*A61K 31/495* (2006.01)
*A61K 31/44* (2006.01)
*C07D 241/36* (2006.01)
*C07D 221/22* (2006.01)

(52) U.S. Cl. ............ 514/250; 514/286; 514/295; 544/343; 546/63; 546/97

(58) Field of Classification Search .......... 514/250, 514/286, 295; 544/343; 546/63, 97
See application file for complete search history.

(56) References Cited

U.S. PATENT DOCUMENTS

| 3,471,503 A | 10/1969 | Carson ............... 260/294.7 |
| 6,410,550 B1 * | 6/2002 | Coe et al. ............... 514/289 |
| 6,887,884 B2 * | 5/2005 | Coe et al. ............... 514/295 |
| 2005/0020616 A1 * | 1/2005 | Coe et al. ............... 514/295 |

FOREIGN PATENT DOCUMENTS

| WO | EP 0955301 | 11/1999 |
| WO | WO 9955680 | 11/1999 |

OTHER PUBLICATIONS

P. Mazzocchi et al., "Synthesis and Pharmacological Activity of 2,3,4,5-Tetrahydro-1,5-methano-1H-3-benzazepines," *J. Med. Chem.*, 22(4), 455-457 (1979).

* cited by examiner

*Primary Examiner*—Brenda Coleman
(74) *Attorney, Agent, or Firm*—Steve T. Zelson; A. David Joran

(57) ABSTRACT

This invention is directed to compounds of the formula (I):

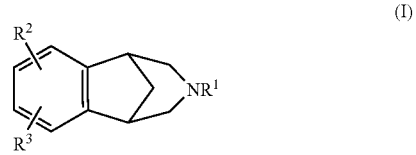

and their pharmaceutically acceptable salts, wherein $R^1$, $R^2$, and $R^3$ are as defined herein; intermediates for the synthesis of such compounds, pharmaceutical compositions containing such compounds; and methods of using such compounds in the treatment of neurological and psychological disorders.

24 Claims, No Drawings

ARYL FUSED AZAPOLYCYCLIC COMPOUNDS

This application is a continuation of application Ser. No. 09/514,002, now U.S. Pat. No. 6,605,610, filed Feb. 25, 2000, which is a CIP of application Ser. No. 09/402,010, now U.S. Pat. No. 6,410,550, filed Sep. 28, 1999, which is a 371 of PCT/IB98/01813, filed Nov. 13, 1998, which claims the benefit of provisional application 60/070,245 filed Dec. 31, 1997.

BACKGROUND OF THE INVENTION

This invention relates to aryl fused azapolycyclic compounds, as defined more specifically by formula I below. Compounds of formula I bind to neuronal nicotinic acetylcholine specific receptor sites and are useful in modulating cholinergic function. Such compounds are useful in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome.

The compounds of this invention may also be used in combination with an antidepressant such as, for example, a tricyclic antidepressant or a serotonin reuptake inhibiting antidepressant (SRI), in order to treat both the cognitive decline and depression associated with AD, PD, stroke, Huntington's chorea or traumatic brain injury (TBI); in combination with muscarinic agonists in order to stimulate both central muscarinic and nicotinic receptors for the treatment, for example, of ALS, cognitive dysfunction, age-related cognitive decline, AD, PD, stroke, Huntington's chorea and TBI; in combination with neurotrophic factors such as NGF in order to maximize cholinergic enhancement for the treatment, for example, of ALS, cognitive dysfunction, age-related cognitive decline, AD, PD stroke, Huntington's chorea and TBI; or in combination with agents that slow or arrest AD such as cognition enhancers, amyloid aggregation inhibitors, secretase inhibitors, tau kinase inhibitors, neuronal anti-inflammatory agents and estrogen-like therapy.

Other compounds that bind to neuronal nicotinic receptor sites are referred to in U.S. patent application Ser. No. 08/963,852, which was filed on Nov. 4, 1997. The foregoing application is owned in common with the present application, and is incorporated herein by reference in its entirety.

SUMMARY OF THE INVENTION

This invention relates to aryl fused azapolycyclic compounds of the formula

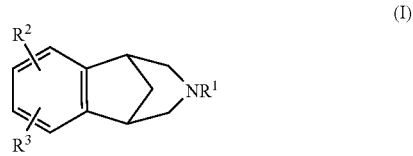

(I)

$R^1$ is hydrogen, $(C_1-C_6)$alkyl, unconjugated $(C_3-C_6)$alkenyl, benzyl, $XC(=O)R^{13}$ or $-CH_2CH_2-O-(C_1-C_4)$alkyl;

$R^2$ and $R^3$ are selected, independently, from hydrogen, $(C_2-C_6)$alkenyl, $(C_2-C_6)$alkynyl, hydroxy, nitro, amino, halo, cyano, $-SO_q(C_1-C_6)$alkyl wherein q is zero, one or two, $(C_1-C_6)$alkylamino-, $[(C_1-C_6)$alkyl$]_2$amino-, $-CO_2R^4$, $-CONR^5R^6$, $-SO_2NR^7R^8$, $-C(=O)R^{13}$, $-XC(=O)R^{13}$, aryl-$(C_0-C_3)$alkyl- or aryl-$(C_0-C_3)$alkyl-O—, wherein said aryl is selected from phenyl and naphthyl, heteroaryl-$(C_0-C_3)$alkyl- or heteroaryl-$(C_0-C_3)$alkyl-O—, wherein said heteroaryl is selected from five to seven membered aromatic rings containing from one to four heteroatoms selected from oxygen, nitrogen and sulfur; $X^2(C_0-C_6)$alkyl- and $X^2(C_1-C_6)$alkoxy-$(C_0-C_6)$alkyl-, wherein $X^2$ is absent or $X^2$ is $(C_1-C_6)$alkylamino- or $[(C_1-C_6)$alkyl$]_2$amino-, and wherein the $(C_0-C_6)$alkyl- or $(C_1-C_6)$alkoxy-$(C_0-C_6)$alkyl- moieties of said $X^2(C_0-C_6)$alkyl- or $X^2(C_1-C_6)$alkoxy-$(C_0-C_6)$alkyl- contains at least one carbon atom, and wherein from one to three of the carbon atoms of said $(C_0-C_6)$alkyl- or $(C_1-C_6)$alkoxy-$(C_0-C_6)$alkoxy- moieties may optionally be replaced by an oxygen, nitrogen or sulfur atom, with the proviso that any two such heteroatoms must be separated by at least two carbon atoms, and wherein any of the alkyl moieties of said $(C_0-C_6)$alkyl- or $(C_1-C_6)$alkoxy-$(C_0-C_6)$alkyl- groups may be optionally substituted with from two to seven fluorine atoms, and wherein one of the carbon atoms of each of the alkyl moieties of said aryl-$(C_0-C_3)$alkyl- and said heteroaryl-$(C_0-C_3)$alkyl- may optionally be replaced by an oxygen, nitrogen or sulfur atom, and wherein each of the foregoing aryl and heteroaryl groups may optionally be substituted with one or more substituents, preferably from zero to two substituents, independently selected from $(C_1-C_6)$alkyl optionally substituted with from one to seven fluorine atoms, $(C_1-C_6)$alkoxy optionally substituted with from two to seven fluorine atoms, halo (e.g., chloro, fluoro, bromo or iodo), $(C_2-C_6)$alkenyl, $(C_2-C_6)$alkynyl, hydroxy, nitro, cyano, amino, $(C_1-C_6)$alkylamino-, $[(C_1-C_6)$alkyl$]_2$amino-, $-CO_2R^4$, $-CONR^5R^6$, $-SO_2NR^7R^8$, $-C(=O)R^{13}$ and $-XC(=O)R^{13}$;

or $R^2$ and $R^3$, together with the carbons to which they are attached, form a four to seven membered monocyclic, or a ten to fourteen membered bicyclic, carbocyclic ring that can be saturated or unsaturated, wherein from one to three of the non-fused carbon atoms of said monocyclic rings, and from one to five of the carbon atoms of said bicyclic rings that are not part of the benzo ring shown in formula I, may optionally and independently be replaced by a nitrogen, oxygen or sulfur, and wherein said monocyclic and bicyclic rings may optionally be substituted with one or more substituents, preferably from zero to two substituents for the monocyclic rings and from zero to three substituents for the bicyclic rings, that are selected, independently, from $(C_0-C_6)$alkyl- or $(C_1-C_6)$alkoxy-$(C_0-C_6)$alkyl-, wherein the total number of carbon atoms does not exceed six and wherein any of the alkyl moieties may optionally be substituted with from one to seven fluorine atoms; nitro, oxo, cyano, halo, $(C_2-C_6)$ alkenyl, $(C_2-C_6)$alkynyl, hydroxy, amino, $(C_1-C_6)$alkylamino-, [$(C_1-C_6)$alkyl]$_2$amino-, —CO$_2$R$^4$, —CONR$^5$R$^6$, —SO$_2$NR$^7$R$^8$, —C(=O)R$^{13}$, and —XC(=O)R$^{13}$;

each R$^4$, R$^5$, R$^6$, R$^7$, R$^8$ and R$^{13}$ is selected, independently, from hydrogen and $(C_1-C_6)$ alkyl, or R$^5$ and R$^6$, or R$^7$ and R$^8$ together with the nitrogen to which they are attached, form a pyrrolidine, piperidine, morpholine, azetidine, piperazine, —N—$(C_1-C_6)$alkylpiperazine or thiomorpholine ring, or a thiomorpholine ring wherein the ring sulfur is replaced with a sulfoxide or sulfone; and each X is, independently, $(C_1-C_6)$alkylene;

with the proviso that: (a) at least one of R$^1$, R$^2$ and R$^3$ must be the other than hydrogen, and (b) when R$^2$ and R$^3$ are hydrogen, R$^1$ cannot be hydrogen, $(C_1-C_6)$alkyl, or unconjugated $(C_3-C_6)$alkenyl, and pharmaceutically acceptable salts of such compounds.

Examples of possible heteroaryl groups within the definition of R$^2$ and R$^3$ are the following: thienyl, oxazoyl, isoxazolyl, pyridyl, pyrimidyl, thiazolyl, tetrazolyl, isothiazolyl, triazolyl, imidazolyl, tetrazolyl, pyrrolyl and the following groups:

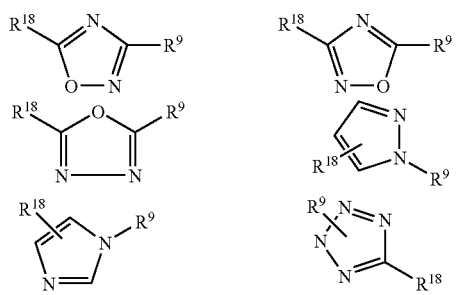

wherein one of R$^9$ and R$^{18}$ is hydrogen or $(C_1-C_6)$alkyl, and the other is a bond to the benzo ring of formula I.

Examples of compounds of this invention are compounds of the formula I, and their pharmaceutically acceptable salts, wherein R$^2$ and R$^3$, together with the benzo ring of formula I, form a bicyclic ring system selected from the following:

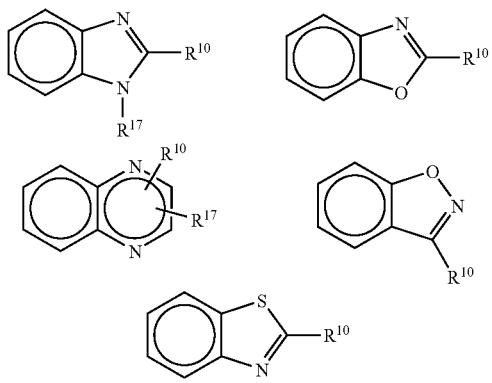

wherein R$^{10}$ and R$^{17}$ are selected, independently, from hydrogen, $(C_1-C_6)$alkyl; and $(C_1-C_6)$alkoxy-$(C_0-C_6)$alkyl- wherein the total number of carbon atoms does not exceed six and wherein any of the alkyl moieties may optionally be substituted with from one to seven fluorine atoms; nitro, cyano, halo, amino, $(C_1-C_6)$alkylamino-, [$(C_1-C_6)$ alkyl]$_2$amino-, —CO$_2$R$^4$, —CONR$^5$R$^6$, —SO$_2$NR$^7$R$^8$, —C(=O)R$^{13}$, —XC(=O)R$^{13}$, phenyl and monocyclic heteroaryl wherein said heteroaryl is defined as R$^2$ and R$^3$ are defined in the definition of compounds of the formula I above;

Other embodiments of this invention relate to compounds of the formula I, and their pharmaceutically acceptable salts, wherein R$^2$ and R$^3$, together with the benzo ring of formula I, form a bicyclic or tricyclic ring system selected from the following:

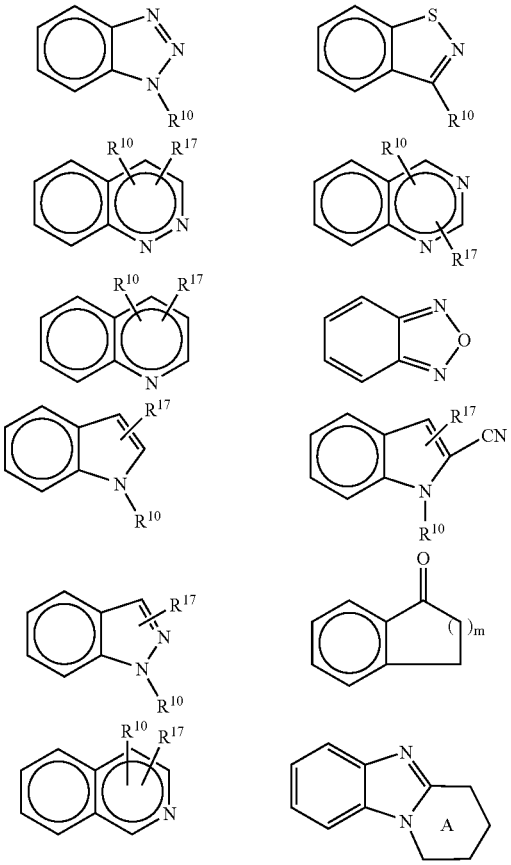

wherein R$^{10}$ and R$^{17}$ are defined as above, and m is zero, one or two, and wherein one of the carbon atoms of ring A can optionally be replaced with oxygen or N$(C_1-C_6)$alkyl.

Other embodiments of this invention relate to compounds of the formula I, and their pharmaceutically acceptable salts, wherein neither R$^2$ nor R$^3$ is attached to the benzo ring of formula I via an oxygen atom.

Other embodiments of this invention relate to compounds of the formula I, and their pharmaceutically acceptable salts, wherein R$^2$ and R$^3$ do not, together with the benzo ring of formula I, form a bicyclic or tricyclic ring system.

Other embodiments of this invention relate to compounds of the formula I wherein one or both of R$^2$ and R$^3$ are —C(=O)R$^{13}$, wherein R$^{13}$ is $(C_1-C_6)$alkyl. Further embodiments of this invention relate to compounds of the formula I wherein one or both of R$^2$ and R$^3$ are —C(=O)

R[13], wherein R[13] is $(C_1-C_6)$alkyl or $(C_1-C_3)$alkyl optionally substituted with from one to seven fluorine atoms. Other embodiments relate to compounds of the formula I wherein one of R[2] and R[3] is $CF_3$, fluoro, cyano, $(C_2-C_6)$alkynyl or $C_2F_5$.

Other further embodiments of the present invention relates to compounds of formula I having the structure

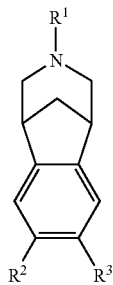

wherein R[1] is as defined above; and R[2] and R[3] are hydrogen, $(C_1-C_6)$alkyl optionally substituted with from one to seven fluorine atoms; $—C(=O)(C_1-C_6)$alkyl, cyano, hydroxy, nitro, amino, $—O(C_1-C_6)$alkyl or halo;

with the proviso that R[2] and R[3] can not both be hydrogen when R[1] is hydrogen, $(C_1-C_6)$alkyl, or unconjugated $(C_3-C_6)$alkenyl.

Examples of specific compounds of the formula I are the following compounds, which, in the instances where there is a center or centers of asymmetry in the molecule, may comprise a racemic mixture or the single enantiomer.

5,13-diazatetracyclo[9.3.1.0$^{2,10}$.0$^{4,8}$]pentadeca-2,4(8),9-trien-6-one;
6-oxo-5-oxa-7,13-diazatetracyclo[9.3.1.0$^{2,10}$.0$^{4,8}$]pentadeca-2(10),3,8-triene;
2-fluoro-N-(4-hydroxy-10-aza-tricyclo[6.3.1.0$^{2,7}$]dodeca-2(7),3,5-trien-5-yl)-benzamide;
6-methyl-5-thia-7,13-diazatetracyclo[9.3.1.0$^{2,10}$.0$^{4,8}$]pentadeca-2(10),3,6,8-tetraene;
6-methyl-7-propyl-5,7,13-triazatetracyclo[9.3.1.0$^{2,10}$.0$^{4,8}$]pentadeca-2(10),3,5,8-tetraene;
5,7,13-triazatetracyclo[9.3.1.0$^{2,10}$.0$^{4,8}$]pentadeca-2(10),3,5,8-tetraene;
7-methyl-5,7,13-triazatetracyclo[9.3.1.0$^{2,10}$.0$^{4,8}$]pentadeca-2(10),3,5,8-tetraene;
6-methyl-5,7,13-triazatetracyclo[9.3.1.0$^{2,10}$.0$^{4,8}$]pentadeca-2(10),3,5,8-tetraene;
6,7-dimethyl-5,7,13-triazatetracyclo[9.3.1.0$^{2,10}$.0$^{4,8}$]pentadeca-2(10),3,5,8-tetraene;
7-propyl-5,7,13-triazatetracyclo[9.3.1.0$^{2,10}$.0$^{4,8}$]pentadeca-2(10),3,5,8-tetraene;
7-butyl-5,7,13-triazatetracyclo[9.3.1.0$^{2,10}$.0$^{4,8}$]pentadeca-2(10),3,5,8-tetraene;
6-methyl-7-isobutyl-5,7,13-triazatetracyclo[9.3.1.0$^{2,10}$.0$^{4,8}$]pentadeca-2(10),3,5,8-tetraene;
7-phenyl-5,7,13-triazatetracyclo[9.3.1.0$^{2,10}$.0$^{4,8}$]-pentadeca-2(10),3,5,8-tetraene;
6-methyl-7-phenyl-5,7,13-triazatetracyclo[9.3.1.0$^{2,10}$.0$^{4,8}$]-pentadeca-2(10),3,5,8-tetraene;
7-neopentyl-5,7,13-triazatetracyclo[9.3.1.0$^{2,10}$.0$^{4,8}$]-pentadeca-2(10),3,5,8-tetraene;
6-methyl-7-neopentyl-5,7,13-triazatetracyclo[9.3.1.0$^{2,10}$.0$^{4,8}$]-pentadeca-2(10),3,5,8-tetraene;
6,7-dimethyl-5,8,14-triazatetracyclo[10.3.1.0$^{2,11}$.0$^{4,9}$]hexadeca-2(11),3,5,7,9-pentaene;
5,8,14-triazatetracyclo[10.3.1.0$^{2,11}$.0$^{4,9}$]hexadeca-2(11),3,5,7,9-pentaene;
14-methyl-5,8,14-triazatetracyclo[10.3.1.0$^{2,11}$.0$^{4,9}$]hexadeca-2(11),3,5,7,9-pentaene;
5-oxa-7,13-diazatetracyclo[9.3.1.0$^{2,10}$.0$^{4,8}$]pentadeca-2(10),3,6,8-tetraene;
6-methyl-5-oxa-7,13-diazatetracyclo[9.3.1.0$^{2,10}$.0$^{4,8}$]pentadeca-2(10),3,6,8-tetraene;
7-methyl-5-oxa-6,13-diazatetracyclo[9.3.1.0$^{2,10}$.0$^{4,8}$]pentadeca-2,4(8),6,9-tetraene;
4-methyl-10-aza-tricyclo[6.3.1.0$^{2,7}$]dodeca-2(7),3,5-triene;
4-nitro-10-azatricyclo[6.3.1.0$^{2,7}$]dodeca-2(7),3,5-triene;
4-amino-10-azatricyclo[6.3.1.0$^{2,7}$]dodeca-2(7),3,5-triene;
N[1]-[10-azatricyclo[6.3.1.0$^{2,7}$]dodeca-2(7),3,5-trien-4-yl]acetamide;
4,5-dinitro-10-aza-tricyclo[6.3.1.0$^{2,7}$]dodeca-2(7),3,5-triene;
4,5-difluoro-10-aza-tricyclo[6.3.1.0$^{2,7}$]dodeca-2(7),3,5-triene;
4-chloro-10-azatricyclo[6.3.1.0$^{2,7}$]dodeca-2(7),3,5-triene;
3-(10-azatricyclo[6.3.1.0$^{2,7}$]dodeca-2(7),3,5-trien-4-yl)-5-methyl-1,2,4-oxadiazole;
10-azatricyclo[6.3.1.0$^{2,7}$]dodeca-2(7),3,5-trien-4-ol;
4,5-dichloro-10-azatricyclo[6.3.1.0$^{2,7}$]dodeca-2(7),3,5-triene;
N[4],N[4]-dimethyl-10-azatricyclo[6.3.1.0$^{2,7}$]dodeca-2(7),3,5-triene-4-sulfonamide;
4-(1-pyrrolidinylsulfonyl)-10-azatricyclo[6.3.1.0$^{2,7}$]dodeca-2(7),3,5-triene;
1-(10-azatricyclo[6.3.1.0$^{2,7}$]dodeca-2(7),3,5-trien-4-yl)-1-ethanone;
3-trifluoromethyl-10-aza-tricyclo[6.3.1.0$^{2,7}$]dodeca-2(7),3,5-triene;
4-trifluoromethyl-10-aza-tricyclo[6.3.1.0$^{2,7}$]dodeca-2(7),3,5-triene;
3-fluoro-10-aza-tricyclo[6.3.1.0$^{2,7}$]dodeca-2(7),3,5-triene;
10-azatricyclo[6.3.1.0$^{2,7}$]dodeca-2(7),3,5-trien-4-yl cyanide;
4-fluoro-10-aza-tricyclo[6.3.1.0$^{2,7}$]dodeca-2(7),3,5-triene;
5,14-diazatetracyclo[10.3.1.0$^{2,11}$.0$^{4,9}$]hexadeca-2(11),3,5,7,9-pentaene;
6-methyl-5,14-diazatetracyclo[10.3.1.0$^{2,11}$.0$^{4,9}$]hexadeca-2(11),3,5,7,9-pentaene;
7-methyl-5,14-diazatetracyclo[10.3.1.0$^{2,11}$.0$^{4,9}$]hexadeca-2(11),3,5,7,9-pentaene;
7-ethyl-5,14-diazatetracyclo[10.3.1.0$^{2,11}$.0$^{4,9}$]hexadeca-2(11),3,5,7,9-pentaene;
8-methyl-5,14-diazatetracyclo[10.3.1.0$^{2,11}$.0$^{4,9}$]hexadeca-2(11),3,5,7,9-pentaene;
5,14-diazatetracyclo[10.3.1.0$^{2,11}$.0$^{4,9}$]hexadeca-2(11),3,5,7,9-pentaene;
6-chloro-5,14-diazatetracyclo[10.3.1.0$^{2,11}$.0$^{4,9}$]hexadeca-2(11),3,5,7,9-pentaene;
6-methoxy-5,14-diazatetracyclo[10.3.1.0$^{2,11}$.0$^{4,9}$]hexadeca-2(11),3,5,7,9-pentaene;
6-chloro-10-fluoro-5,14-diazatetracyclo[10.3.1.0$^{2,11}$.0$^{4,9}$]hexadeca-2(11),3,5,7,9-pentaene;
5,8,14-triazatetracyclo[10.3.1.0$^{2,11}$.0$^{4,9}$]hexadeca-2(11),3,7,9-tetraen-one;
6-chloro-3-fluoro-5,14-diazatetracyclo[10.3.1.0$^{2,11}$.0$^{4,9}$]hexadeca-2(11),3,5,7,9-pentaene;
and pharmaceutically acceptable salts thereof.

Other embodiments compounds of the invention include but are not limited to:
6-methyl-5,7-dioxo-6,13-diazatetracyclo[9.3.1.0$^{2,10}$.0$^{4,8}$]pentadeca-2(10),3,8-triene;

6-methyl-5-oxo-6,13-diazatetracyclo[9.3.1.0$^{2,10}$.0$^{4,8}$]pentadeca-2(10),3,8-triene;

5,7-dimethyl-6-oxo-5,7,13-triazatetracyclo[9.3.1.0$^{2,10}$.0$^{4,8}$]pentadeca-2(10),3,8-triene;

5,7-dioxo-6,13-diazatetracyclo[9.3.1.0$^{2,10}$.0$^{4,8}$]pentadeca-2(10),3,8-triene;

5-oxo-6,13-diazatetracyclo[9.3.1.0$^{2,10}$.0$^{4,8}$]pentadeca-2(10),3,8-triene;

6-oxo-5,7,13-triazatetracyclo[9.3.1.0$^{2,10}$.0$^{4,8}$]pentadeca-2(10),3,8-triene;

6-methyl-5-thia-5-dioxo-6,13-diazatetracyclo[9.3.1.0$^{2,10}$.0$^{4,8}$]pentadeca-2(10),3,6,8-tetraene;

7-dimethylamino-5-thia-5-dioxo-6,13-diazatetracyclo[9.3.1.0$^{2,10}$.0$^{4,8}$]pentadeca-2(10),3,6,8-tetraene;

6,7-dioxo-5,8,14-triazatetracyclo[10.3.1.0$^{2,11}$.0$^{4,9}$]hexadeca-2(11),3,9-triene;

5,8-dimethyl-6,7-dioxo-5,8,14-triazatetracyclo[10.3.1.0$^{2,11}$.0$^{4,9}$]hexadeca-2(11),3,9-triene;

5-oxa-7-methyl-6-oxo-7,13-diazatetracyclo[9.3.1.0$^{2,10}$.0$^{4,8}$]pentadeca-2(10),3,8-triene;

5-fluoro-10-aza-tricyclo[6.3.1.0$^{2,7}$]dodeca-2(7),3,5-triene-4-carbonitrile;

4-ethynyl-5-fluoro-10-aza-tricyclo[6.3.1.0$^{2,7}$]dodeca-2(7),3,5-triene;

5-ethynyl-10-aza-tricyclo[6.3.1.0$^{2,7}$]dodeca-2(7),3,5-triene-4-carbonitrile;

5-chloro-10-aza-tricyclo[6.3.1.0$^{2,7}$]dodeca-2(7),3,5-triene-4-carbonitrile;

4-ethynyl-5-chloro-10-aza-tricyclo[6.3.1.0$^{2,7}$]dodeca-2(7),3,5-triene;

4-fluoro-5-trifluoromethyl-10-aza-tricyclo[6.3.1.0$^{2,7}$]dodeca-2(7),3,5-triene;

4-chloro-5-trifluoromethyl-10-aza-tricyclo[6.3.1.0$^{2,7}$]dodeca-2(7),3,5-triene;

5-trifluoromethyl-10-aza-tricyclo[6.3.1.0$^{2,7}$]dodeca-2(7),3,5-triene-4-carbonitrile;

4-ethynyl-5-trifluoromethyl-10-aza-tricyclo[6.3.1.0$^{2,7}$]dodeca-2(7),3,5-triene;

4,5-bistrifluoromethyl-10-aza-tricyclo[6.3.1.0$^{2,7}$]dodeca-2(7),3,5-triene;

and pharmaceutically acceptable salts thereof. Other embodiments of the invention are the hydrochloride salts of the above enumerated compounds.

This invention also relates to compounds of the formula

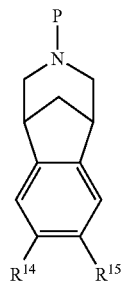

wherein P is hydrogen, methyl, COOR$^{16}$ wherein R$^{16}$ is (C$_1$–C$_6$)alkyl, allyl, 2,2,2-trichloroethyl or (C$_1$–C$_8$)alkyl; —C(=O)NR$^5$R$^6$ wherein R$^5$ and R$^6$ are defined as in formula I above; —C(=O)H, —C(=O)(C$_1$–C$_6$)alkyl wherein the alkyl moiety may optionally be substituted with from 1 to 3 halo atoms, preferably with from 1 to 3 fluoro or chloro atoms; benzyl or t-butoxycarbonyl (t-Boc); and R$^{14}$ and R$^{15}$ are selected, independently, from hydrogen, (C$_1$–C$_6$)alkyl optionally substituted with from one to seven fluorine atoms; —C(=O)(C$_1$–C$_6$)alkyl, cyano, hydroxy, nitro, amino, —O(C$_1$–C$_6$)alkyl or halo; with the proviso that R$^{14}$ and R$^{15}$ can not both be hydrogen when P is hydrogen, (C$_1$–C$_6$)alkyl, or unconjugated (C$_3$–C$_6$)alkenyl. Such compounds are useful as intermediates in the synthesis of compounds of the formula I.

The invention also relates to compounds of the formula:

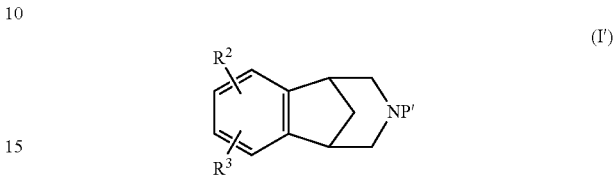

wherein R$^2$ and R$^3$ are defined above; and P' is COOR$^{16}$ wherein R$^{16}$ is allyl, 2,2,2-trichloroethyl or (C$_1$–C$_6$)alkyl; —C(=O)NR$^5$R$^6$ wherein R$^5$ and R$^6$ are also as defined above; —C(=O)H, —C(=O)(C$_1$–C$_6$)alkyl wherein the alkyl moiety may optionally be substituted with from 1 to 3 halo atoms, preferably with from 1 to 3 fluoro or chloro atoms; benzyl, or t-butoxycarbonyl.

Unless otherwise indicated, the term "halo", as used herein, includes fluoro, chloro, bromo and iodo.

Unless otherwise indicated, the term "alkyl", as used herein, includes straight chain moieties, and where the number of carbon atoms suffices, branched and cyclic moieties.

The term "alkoxy", as used herein, means "—O-alkyl" or "alkyl-O—", wherein "alkyl" is defined as above.

The term "alkylene, as used herein, means an alkyl radical having two available bonding sites (i.e., -alkyl-), wherein "alkyl" is defined as above.

Unless otherwise indicated, the term "one or more substituents", as used herein, refers to from one to the maximum number of substituents possible based on the number of available bonding sites.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The compounds of formula I may have optical centers and therefore may occur in different enantiomeric configurations. The invention includes all enantiomers, diastereomers, and other stereoisomers of such compounds of formula I, as well as racemic and other mixtures thereof.

Particularly, preferred enantiomers of the invention include:

(+)-5,13-diazatetracyclo[9.3.1.0$^{2,10}$.0$^{4,8}$]pentadeca-2,4(8),9-trien-6-one;

(+)-6-oxo-5-oxa-7,13-diazatetracyclo[9.3.1.0$^{2,10}$.0$^{4,8}$]pentadeca-2(10),3,8-triene;

(+)-2-fluoro-N-(4-hydroxy-10-aza-tricyclo[6.3.1.0$^{2,7}$]dodeca-2(7),3,5-trien-5-yl)benzamide;

(+)-6-methyl-5-thia-7,13-diazatetracyclo[9.3.1.0$^{2,10}$.0$^{4,8}$]pentadeca-2(10),3,6,8-tetraene;

(+)-6-methyl-7-propyl-5,7,13-triazatetracyclo[9.3.1.0$^{2,10}$.0$^{4,8}$]pentadeca-2(10),3,5,8-tetraene;

(+)-7-methyl-5,7,13-triazatetracyclo[9.3.1.0$^{2,10}$.0$^{4,8}$]pentadeca-2(10),3,5,8-tetraene;

(+)-6,7-dimethyl-5,7,13-triazatetracyclo[9.3.1.0$^{2,10}$.0$^{4,8}$]pentadeca-2(10),3,5,8-tetraene;

(+)-7-propyl-5,7,13-triazatetracyclo[9.3.1.0$^{2,10}$.0$^{4,8}$]pentadeca-2(10),3,5,8-tetraene;
(+)-7-butyl-5,7,13-triazatetracyclo[9.3.1.0$^{2,10}$.0$^{4,8}$]pentadeca-2(10),3,5,8-tetraene;
(+)-6-methyl-7-isobutyl-5,7,13-triazatetracyclo[9.3.1.0$^{2,10}$.0$^{4,8}$]pentadeca-2(10),3,5,8-tetraene;
(+)-7-phenyl-5,7,13-triazatetracyclo[9.3.1.0$^{2,10}$.0$^{4,8}$]pentadeca-2(10),3,5,8-tetraene;
(+)-6-methyl-7-phenyl-5,7,13-triazatetracyclo[9.3.1.0$^{2,10}$.0$^{4,8}$]pentadeca-2(10),3,5,8-tetraene;
(+)-7-neopentyl-5,7,13-triazatetracyclo[9.3.1.0$^{2,10}$.0$^{4,8}$]pentadeca-2(10),3,5,8-tetraene;
(+)-6-methyl-7-neopentyl-5,7,13-triazatetracyclo[9.3.1.0$^{2,10}$.0$^{4,8}$]pentadeca-2(10),3,5,8-tetraene;
(+)-5-oxa-7,13-diazatetracyclo[9.3.1.0$^{2,10}$.0$^{4,8}$]pentadeca-2(10),3,6,8-tetraene;
(+)-6-methyl-5-oxa-7,13-diazatetracyclo[9.3.1.0$^{2,10}$.0$^{4,8}$]pentadeca-2(10),3,6,8-tetraene;
(+)-7-methyl-5-oxa-6,13-diazatetracyclo[9.3.1.0$^{2,10}$.0$^{4,8}$]pentadeca-2,4(8),6,9-tetraene;
(+)-4-methyl-10-aza-tricyclo[6.3.1.0$^{2,7}$]dodeca-2(7),3,5-triene;
(+)-4-nitro-10-azatricyclo[6.3.1.0$^{2,7}$]dodeca-2(7),3,5-triene;
(+)-4-amino-10-azatricyclo[6.3.1.0$^{2,7}$]dodeca-2(7),3,5-triene;
(+)-N$^1$-[10-azatricyclo[6.3.1.0$^{2,7}$]dodeca-2(7),3,5-trien-4-yl]acetamide;
(+)-4-chloro-10-azatricyclo[6.3.1.0$^{2,7}$]dodeca-2(7),3,5-triene;
(+)-3-(10-azatricyclo[6.3.1.0$^{2,7}$]dodeca-2(7),3,5-trien-4-yl)-5-methyl-1,2,4-oxadiazole; (+)-10-azatricyclo[6.3.1.0$^{2,7}$]dodeca-2(7),3,5-trien-4-ol;
(+)-N$^4$,N$^4$-methyl-10-azatricyclo[6.3.1.0$^{2,7}$]dodeca-2(7),3,5-triene-4-sulfonamide;
(+)-4-(1-pyrrolidinylsulfonyl)-10-azatricyclo[6.3.1.0$^{2,7}$]dodeca-2(7),3,5-triene;
(+)-1-(10-azatricyclo[6.3.1.0$^{2,7}$]dodeca-2(7),3,5-trien-4-yl)-1-ethanone;
(+)-3-trifluoromethyl-10-aza-tricyclo[6.3.1.0$^{2,7}$]dodeca-2(7),3,5-triene;
(+)-4-trifluoromethyl-10-aza-tricyclo[6.3.1.0$^{2,7}$]dodeca-2(7),3,5-triene;
(+)-3-fluoro-10-aza-tricyclo[6.3.1.0$^{2,7}$]dodeca-2(7),3,5-triene;
(+)-10-azatricyclo[6.3.1.0$^{2,7}$]dodeca-2(7),3,5-trien-4-yl cyanide;
(+)-4-fluoro-10-aza-tricyclo[6.3.1.0$^{2,7}$]dodeca-2(7),3,5-triene;
(+)-6-methyl-5-oxo-6,13-diazatetracyclo[9.3.1.0$^{2,10}$.0$^{4,8}$]pentadeca-2(10),3,8-triene;
(+)-5-oxo-6,13-diazatetracyclo[9.3.1.0$^{2,10}$.0$^{4,8}$]pentadeca-2(10),3,8-triene;
(+)-6-methyl-5-thia-5-dioxo-6,13-diazatetracyclo[9.3.1.0$^{2,10}$.0$^{4,8}$]pentadeca-2(10),3,6,8-tetraene;
(+)-7-dimethylamino-5-thia-5-dioxo-6,13-diazatetracyclo[9.3.1.0$^{2,10}$.0$^{4,8}$]pentadeca-2(10),3,6,8-tetraene;
(+)-5-oxa-7-methyl-6-oxo-7,13-diazatetracyclo[9.3.1.0$^{2,10}$.0$^{4,8}$]pentadeca-2(10),3,8-triene;
(+)-5-fluoro-10-aza-tricyclo[6.3.1.0$^{2,7}$]dodeca-2(7),3,5-triene-4-carbonitrile;
(+)-4-ethynyl-5-fluoro-10-aza-tricyclo[6.3.1.0$^{2,7}$]dodeca-2(7),3,5-triene;
(+)-5-ethynyl-10-aza-tricyclo[6.3.1.0$^{2,7}$]dodeca-2(7),3,5-triene-4-carbonitrile;
(+)-5-chloro-10-aza-tricyclo[6.3.1.0$^{2,7}$]dodeca-2(7),3,5-triene-4-carbonitrile;
(+)-4-ethynyl-5-chloro-10 aza-tricyclo[6.3.1.0$^{2,7}$]dodeca-2(7),3,5-triene;
(+)-4-fluoro-5-trifluoromethyl-10-aza-tricyclo[6.3.1.0$^{2,7}$]dodeca-2(7),3,5-triene;
(+)-4-chloro-5-trifluoromethyl-10-aza-tricyclo[6.3.1.0$^{2,7}$]dodeca-2(7),3,5-triene;
(+)-5-trifluoromethyl-10-aza-tricyclo[6.3.1.0$^{2,7}$]dodeca-2(7),3,5-triene-4-carbonitrile;
(+)-4-ethynyl-5-trifluoromethyl-10-aza-tricyclo[6.3.1.0$^{2,7}$]dodeca-2(7),3,5-triene;
(+)-5,14-diazatetracyclo[10.3.1.0$^{2,11}$.0$^{4,9}$]hexadeca-2(11),3,5,7,9-pentaene;
(+)-6-methyl-5,14-diazatetracyclo[10.3.1.0$^{2,11}$.0$^{4,9}$]hexadeca-2(11),3,5,7,9-pentaene;
(+)-7-methyl-5,14-diazatetracyclo[10.3.1.0$^{2,11}$.0$^{4,9}$]hexadeca-2(11),3,5,7,9-pentaene;
(+)-7-ethyl-5,14-diazatetracyclo[10.3.1.0$^{2,11}$.0$^{4,9}$]hexadeca-2(11),3,5,7,9-pentaene;
(+)-8-methyl-5,14-diazatetracyclo[10.3.1.0$^{2,11}$.0$^{4,9}$]hexadeca-2(11),3,5,7,9-pentaene;
(+)-5,14-diazatetracyclo[10.3.1.0$^{2,11}$.0$^{4,9}$]hexadeca-2(11),3,7,9-tetraen-6-one;
(+)-6-chloro-5,14-diazatetracyclo[10.3.1.0$^{2,11}$.0$^{4,9}$]hexadeca-2(11),3,5,7,9-pentaene;
(+)-6-methoxy-5,14-diazatetracyclo[10.3.1.0$^{2,11}$.0$^{4,9}$]hexadeca-2(11),3,5,7,9-pentaene;
(+)-6-chloro-10-fluoro-5,14-diazatetracyclo[10.3.1.0$^{2,11}$.0$^{4,9}$]hexadeca-2(11), 3,5,7,9-pentaene;
(+)-5,8,14-triazatetracyclo[10.3.1.0$^{2,11}$.0$^{4,9}$]hexadeca-2(11),3,7,9-tetraen-6-one;
(+)-6-chloro-3-fluoro-5,14-diazatetracyclo[10.3.1.0$^{2,11}$.0$^{4,9}$]hexadeca-2(11),3,5,7,9-pentaene;
and pharmaceutically acceptable salts thereof.

In addition, other preferred enantiomers of the compounds of the invention include:
(−)-5,13-diazatetracyclo[9.3.1.0$^{2,10}$.0$^{4,8}$]pentadeca-2,4(8),9-trien-6-one;
(−)-6-oxo-5-oxa-7,13-diazatetracyclo[9.3.1.0$^{2,10}$.0$^{4,8}$]pentadeca-2(10),3,8-triene;
(−)-2-fluoro-N-(4-hydroxy-10-aza-tricyclo[6.3.1.0$^{2,7}$]dodeca-2(7),3,5-trien-5-yl)-benzamide;
(−)-6-methyl-6-thia-7,13-diazatetracyclo[9.3.1.0$^{2,10}$.0$^{4,8}$]pentadeca-2(10),3,6,8-tetraene;
(−)-6-methyl-7-propyl-5,7,13-triazatetracyclo[9.3.1.0$^{2,10}$.0$^{4,8}$]pentadeca-2(10),3,5,8-tetraene;
(−)-7-methyl-5,7,13-triazatetracyclo[9.3.1.0$^{2,10}$.0$^{4,8}$]pentadeca-2(10),3,5,8-tetraene;
(−)-6,7-dimethyl-5,7,13-triazatetracyclo[9.3.1.0$^{2,10}$.0$^{4,8}$]pentadeca-2(10),3,5,8-tetraene;
(−)-7-propyl-5,7,13-triazatetracyclo[9.3.1.0$^{2,10}$.0$^{4,8}$]pentadeca-2(10),3,5,8-tetraene;
(−)-7-butyl-5,7,13-triazatetracyclo[9.3.1.0$^{2,10}$.0$^{4,8}$]pentadeca-2(10),3,5,8-tetraene;
(−)-6-methyl-7-isobutyl-5,7,13-triazatetracyclo[9.3.1.0$^{2,10}$.0$^{4,8}$]pentadeca-2(10),3,5,8-tetraene;
(−)-7-phenyl-5,7,13-triazatetracyclo[9.3.1.0$^{2,10}$.0$^{4,8}$]pentadeca-2(10),3,5,8-tetraene;
(−)-6-ethyl-7-phenyl-5,7,13-triazatetracyclo[9.3.1.0$^{2,10}$.0$^{4,8}$]pentadeca-2(10),3,5,8-tetraene;
(−)-7-neopentyl-5,7,13-triazatetracyclo[9.3.1.0$^{2,10}$.0$^{4,8}$]pentadeca-2(10),3,5,8-tetraene;
(−)-6-methyl-7-neopentyl-5,7,13-triazatetracyclo[9.3.1.0$^{2,10}$.0$^{4,8}$]pentadeca-2(10),3,5,8-tetraene;
(−)-5-oxa-7,13-diazatetracyclo[9.3.1.0$^{2,10}$.0$^{4,8}$]pentadeca-2(10),3,5,8-tetraene;
(−)-6-methyl-5-oxa-7,13-diazatetracyclo[9.3.1.0$^{2,10}$.0$^{4,8}$]pentadeca-2(10),3,5,8-tetraene;

(−)-7-methyl-5-oxa-6,13-diazatetracyclo[9.3.1.0$^{2,10}$.0$^{4,8}$]pentadeca-2,4(8),6,9-tetraene;
(−)-4-methyl-10-aza-tricyclo[6.3.1.0$^{2,7}$]dodeca-2(7),3,5-triene;
(−)-4-nitro-10-azatricyclo[6.3.1.0$^{2,7}$]dodeca-2(7),3,5-triene;
(−)-4-amino-10-azatricyclo[6.3.1.0$^{2,7}$]dodeca-2(7),3,5-triene;
(−)-N$^1$-[10-azatricyclo[6.3.1.0$^{2,7}$]dodeca-2(7),3,5-trien-4-yl]acetamide;
(−)-4-chloro-10-azatricyclo[6.3.1.0$^{2,7}$]dodeca-2(7),3,5-triene;
(−)-3-(10-azatricyclo[6.3.1.0$^{2,7}$]dodeca-2(7),3,5-trien-4-yl)-5-methyl-1,2,4-oxadiazole;
(−)-10-azatricyclo[6.3.1.0$^{2,7}$]dodeca-2(7),3,5-trien-4-ol;
(−)-N$^4$,N$^4$-dimethyl-10-azatricyclo[6.3.1.0$^{2,7}$]dodeca-2(7),3,5-trien-4-sulfonamide;
(−)-4-(1-pyrrolidinylsulfonyl)-10-azatricyclo[6.3.1.0$^{2,7}$]dodeca-2(7),3,5-triene;
(−)-1-(10-azatricyclo[6.3.1.0$^{2,7}$]dodeca-2(7),3,5-trien-4-yl)-1-ethanone;
(−)-3-trifluoromethyl-10-aza-tricyclo[6.3.1.0$^{2,7}$]dodeca-2(7),3,5-triene;
(−)-4-trifluoromethyl-10-aza-tricyclo[6.3.1.0$^{2,7}$]dodeca-2(7),3,5-triene;
(−)-3-fluoro-10-azatricyclo[6.3.1.0$^{2,7}$]dodeca-2(7),3,5-triene;
(−)-10-azatricyclo[6.3.1.0$^{2,7}$]dodeca-2(7),3,5-trien-4-yl cyanide;
(−)-4-fluoro-10-aza-tricyclo[6.3.1.0$^{2,7}$]dodeca-2(7),3,5-triene;
(−)-6-methyl-5-oxo-6,13-diazatetracyclo-[9.3.1.0$^{2,10}$.0$^{4,8}$]pentadeca-2(10),3,8-triene;
(−)-5-oxo-6,13-diazatetracyclo[9.3.1.0$^{2,10}$.0$^{4,8}$]pentadeca-2(10),3,8-triene;
(−)-6-methyl-5-thia-5-dioxo-6,13-diazatetracyclo[9.3.1.0$^{2,10}$.0$^{4,8}$]pentadeca-2(10),3,6,8-tetraene;
(−)-7-dimethylamino-5-thia-5-dioxo-6,13-diazatetracyclo[9.3.1.0$^{2,10}$.0$^{4,8}$]pentadeca-2(10),3,6,8-tetraene;
(−)-5-oxa-7-methyl-6-oxo-7,13-diazatetracyclo[9.3.1.0$^{2,10}$.0$^{4,8}$]pentadeca-2(10),3,8-triene;
(−)-5-fluoro-10-aza-tricyclo[6.3.1.0$^{2,7}$]dodeca-2(7),3,5-triene-4-carbonitrile;
(−)-4-ethynyl-5-fluoro-10-aza-tricyclo[6.3.1.0$^{2,7}$]dodeca-2(7),3,5-triene;
(−)-5-ethynyl-10-aza-tricyclo[6.3.1.0$^{2,7}$]dodeca-2(7),3,5-triene-4-carbonitrile;
(−)-5-chloro-10-aza-tricyclo[6.3.1.0$^{2,7}$]dodeca-2(7),3,5-triene-4-carbonitrile;
(−)-4-ethynyl-5-chloro-10-aza-tricyclo[6.3.1.0$^{2,7}$]dodeca-2(7),3,5-triene;
(−)-4-fluoro-5-trifluoromethyl-10-aza-tricyclo[6.3.1.0$^{2,7}$]dodeca-2(7),3,5-triene;
(−)-4-chloro-5-trifluoromethyl-10-aza-tricyclo[6.3.1.0$^{2,7}$]dodeca-2(7),3,5-triene;
(−)-5-trifluoromethyl-10-aza-tricyclo[6.3.1.0$^{2,7}$]dodeca-2(7),3,5-triene-4-carbonitrile;
(−)-4-ethynyl-5-trifluoromethyl-10-aza-tricyclo[6.3.1.0$^{2,7}$]dodeca-2(7),3,5-triene;
(−)-5,14-diazatetracyclo[10.3.1.0$^{2,11}$.0$^{4,9}$]hexadeca-2(11),3,5,7,9-pentaene;
(−)-6-methyl-5,14-diazatetracyclo[10.3.1.0$^{2,11}$.0$^{4,9}$]hexadeca-2(11),3,5,7,9-pentaene;
(−)-7-methyl-5,14-diazatetracyclo[10.3.1.0$^{2,11}$.0$^{4,9}$]hexadeca-2(11),3,5,7,9-pentaene;
(−)-7-ethyl-5,14-diazatetracyclo[10.3.1.0$^{2,11}$.0$^{4,9}$]hexadeca-2(11),3,5,7,9-pentaene;
(−)-8-methyl-5,14-diazatetracyclo[10.3.1.0$^{2,11}$.0$^{4,9}$]hexadeca-2(11),3,5,7,9-pentaene;
(−)-5,14-diazatetracyclo[10.3.1.0$^{2,11}$.0$^{4,9}$]hexadeca-2(11),3,7,9-tetraen-6-one;
(−)-6-chloro-5,14-diazatetracyclo[10.3.1.0$^{2,11}$.0$^{4,9}$]hexadeca-2(11),3,5,7,9-pentaene;
(−)-6-methoxy-5,14-diazatetracyclo[10.3.1.0$^{2,11}$.0$^{4,9}$]hexadeca-2(11),3,5,7,9-pentaene;
(−)-6-chloro-10-fluoro-5,14-diazatetracyclo[10.3.1.0$^{2,11}$.0$^{4,9}$]hexadeca-2(11),3,5,7,9-pentaene;
(−)-5,8,14-triazatetracyclo[10.3.1.0$^{2,11}$.0$^{4,9}$]hexadeca-2(11),3,7,9-tetraen-6-one;
(−)-6-chloro-3-fluoro-5,14-diazatetracyclo[10.3.1.0$^{2,11}$.0$^{4,9}$]hexadeca-2(11),3,5,7, pentaene;
and pharmaceutically acceptable salts thereof.

The present invention also relates to all radiolabeled forms of the compounds of the formula I. Preferred radiolabeled compounds of formula I are those wherein the radiolabels are selected from as $^3$H, $^{11}$C, $^{14}$C, $^{18}$F, $^{123}$I and $^{125}$I. Such radiolabeled compounds are useful as research and diagnostic tools in metabolism studies, such as pharmacokinetics studies, etc., and in binding assays in both animals and man.

The present invention also relates to a pharmaceutical composition for use in reducing nicotine addiction or aiding in the cessation or lessening of tobacco use in a mammal, including a human, comprising an amount of a compound of the formula I, or a pharmaceutically acceptable salt thereof, that is effective in reducing nicotine addiction or aiding in the cessation or lessening of tobacco use and a pharmaceutically acceptable carrier.

The present invention also relates to a method for reducing nicotine addiction or aiding in the cessation or lessening of tobacco use in a mammal, including a human, comprising administering to said mammal an amount of a compound of the formula I, or a pharmaceutically acceptable salt thereof, that is effective in reducing nicotine addiction or aiding in the cessation or lessening of tobacco use.

The present invention also relates to a method of treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising administering to a mammal in need of such treatment an amount of a compound of the formula I, or a pharmaceutically acceptable salt thereof, that is effective in treating such disorder or condition.

The present invention also relates to a pharmaceutical composition for treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising an amount of a compound of the formula I, or a pharmaceutically acceptable salt thereof, and a pharmaceutically acceptable carrier.

The present invention also relates to a method for reducing nicotine addiction or aiding in the cessation or lessening of tobacco use in a mammal, comprising administering to said mammal an amount of a compound comprising an amount of a compound of the formula

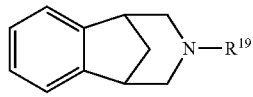

wherein $R^{19}$ is selected from the group consisting of hydrogen, $(C_1-C_6)$alkyl, or unconjugated $(C_3-C_6)$alkenyl, or a pharmaceutically acceptable salt thereof, that is effective in reducing nicotine addiction or aiding in the cessation or lessening of tobacco use.

The present invention also relates to a method for treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.g., dependencies on, or addictions to nicotine and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising administering to a mammal in need of such treatment an amount of a compound of the formula

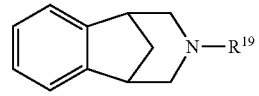

where $R^{19}$ is defined above, or a pharmaceutically acceptable salt thereof, that is effective in treating such disorder or condition.

This invention also relates to the pharmaceutically acceptable acid addition salts of the compounds of formula I. Examples of pharmaceutically acceptable acid addition salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, malic acid, di-p-toluoyl tartaric acid, and mandelic acid, as well salts formed from other acids known to those of skill in the art to form pharmaceutically acceptable acid addition salts to basic compounds. Other possible acid addition salts are, e.g., salts containing pharmaceutically acceptable anions, such as the hydroiodide, nitrate, sulfate or bisulfate, phosphate or acid phosphate, acetate, lactate, gluconate, saccharate, benzoate, methanesulfonate, ethanesulfonate, benzenesulfonate, and pamoate (i.e., 1.1'-methylene-bis-(2-hydroxy-3-naphthoate) salts).

The present invention also relates to methods for the preparation of the novel compounds of formula I. The invention is directed to a process for the preparation of a compound of formula IA:

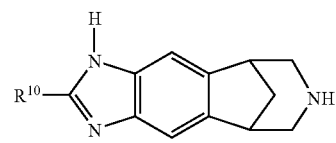

wherein $R^{10}$ is defined above, comprising the step of reacting a compound of formula VI:

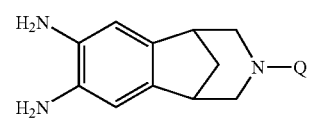

wherein Q is a nitrogen protecting group, with a compound of formula XXIIB:

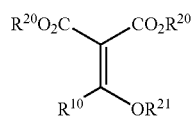

wherein $R^{20}$ and $R^{21}$ are each independently $(C_1-C_6)$ alkyl, and wherein $R^{10}$ is defined above; and
(ii) removing the protecting group Q.

The nitrogen protecting group Q may be chosen from suitable groups known to those of skill in the art including —COCF$_3$, —COCCl$_3$, —COOCH$_2$CCl$_3$, —COO(C$_1$–C$_6$)

alkyl and —COOCH$_2$C$_6$H$_5$. These groups may be added or removed by methods described for each in T. W. Greene and G. M. Wuts, *Protective Groups in Organic Synthesis* (John Wiley & Sons, New York, 1991). Preferably, the nitrogen protecting group Q is a trifluoroacetyl or a t-butoxycarbonyl group.

The invention also relates to a process for the preparation of a compound of formula IB:

IB wherein R$^{10}$ and R$^{17}$ are defined above, comprising the steps of
(i) of reacting a compound of formula VI:

VI wherein Q is a nitrogen protecting group, with a compound of formula XXIIB:

XXIIB wherein R$^{20}$ and R$^{21}$ are each independently (C$_1$–C$_6$)alkyl, and wherein R$^{10}$ is defined above; and
(ii) allowing the product of step (i) to react with a compound of the formula R$^{17}$Z,
wherein R$^{17}$ is defined above, and Z is a leaving group, in the presence of a base;
(iii) removing the protecting group Q.

Preferably, in this method to prepare IB the leaving group is selected from the group consisting of halo, halosulfonate, mesylate and tosylate, and the base is an alkali metal hydride, hydroxide or carbonate. Preferably, the protecting group Q is a trifluoroacetyl or a t-butoxycarbonyl group.

The invention also relates to another process for the preparation of a compound of formula IB:

IB wherein R$^{10}$ and R$^{17}$ are defined above, comprising the steps of
(i) of reacting a compound of formula XXIIIA:

XXIVA wherein Q is a nitrogen protecting group, with a compound of formula XXIIB:

XXIIB wherein R$^{20}$ and R$^{21}$ are each independently (C$_1$–C$_6$)alkyl, and wherein R$^{10}$ is defined above; and
(iii) removing the protecting group Q.

Preferably, in this method to prepare IB, the protecting group Q is a trifluoroacetyl or a t-butoxycarbonyl group.

The invention is also directed to a process for preparing a compound of formula IC

IC wherein R$^{10}$ and R$^{17}$ are as defined above, comprising the steps of
(i) allowing a compound of formula VI:

VI wherein Q is a nitrogen protecting group, to react with a compound of formula wherein Y is an alkali metal or alkaline earth metal cation; or a compound of formula

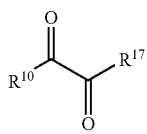

wherein $R^{10}$ and $R^{17}$ are as defined above; and (ii) removing the protecting group Q.

The protecting group Q is preferably a trifluoroacetate group or a t-butoxycarbonyl group. Preferably, step (i) is conducted in a polar solvent, more preferably, water, THF, DMF, DMSO, a mixture of water and any of THF, DMF or DMSO. In addition, the processes to make each of compounds IA, IB and IC, preferably comprise the further step of reducing the nitro groups of a compound of formula IIC:

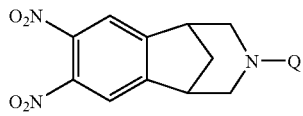

IIC wherein Q is a nitrogen protecting group to form a compound of formula VI

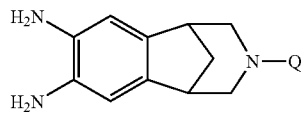

VI

More preferably, the reduction is conducted in the presence of hydrogen gas employing a palladium catalyst. Preferably, the protecting group Q is a trifluoroacetyl or a t-butoxycarbonyl group.

The invention is also directed to a process for the preparation of a compound of formula IE:

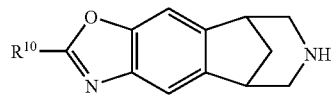

IE wherein $R^{10}$ is defined above, comprising the steps of (i) reducing the nitro group of a compound of formula VIIIA

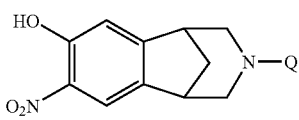

VIIIA wherein Q is a nitrogen protecting group;

(ii) allowing the amino product to react with an acid chloride of the formula $R^{10}COCl$ or an acid anhydride of the formula $(R^{10}CO)_2O$ wherein $R^{10}$ is $(C_1-C_6)$alkyl, or a compound of the formula $R^{10}C((C_1-C_6)alkoxy)_3$;

(iii) removing the protecting group Q.

Preferably, in this process to prepare IE, the reduction of step (i) is conducted by hydrogenation with a palladium or platinum catalyst. Preferably, the protecting group Q is a trifluoroacetyl or a t-butoxycarbonyl group.

The invention is further related to a process for the preparation of a compound of formula IF:

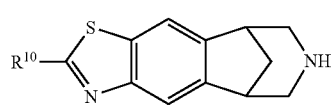

IF wherein $R^{10}$ is as defined above; comprising the steps of (i) allowing a compound of formula XA:

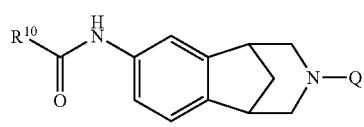

XA wherein $R^{10}$ is as defined above, and Q is a nitrogen protecting group, to react with Lawesson's reagent;

(ii) allowing the product of step (i) to react with potassium ferricyanide and sodium hydroxide;

(iii) removing the protecting group Q.

Preferably, the protecting group Q is a trifluoroacetyl or a t-butoxycarbonyl group.

The invention also relates to a process for preparing compounds the formula:

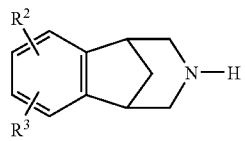

wherein $R^2$ and $R^3$ are defined above; comprising the steps of (i) subjecting a compound of formula XIIIB:

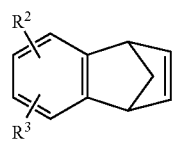

XIIIB to ozonolysis conditions;

(ii) partially reducing the resulting ozonide product of step (i) to a dialdehyde or product of equivalent oxidation state;

(iii) allowing the product of step (ii) to react with an arylmethylamine; and (iv) removing the arylmethyl group.

The ozonolysis conditions used may be any of those known to those of skill in the art. Preferably, the ozonolysis conditions are ozone in methanol or dichloromethane, preferably methanol. In step (ii), the reduction of the ozonolysis product or ozonide is preferably conducted by hydrogenation, e.g., in the presence of hydrogen gas and a platinum or palladium catalyst with or without carbon/charcoal. The arylmethylamine employed in step (iii) is benzylamine, 4-methoxybenzylamine or 3,4-dimethoxybenzylamine, preferably benzylamine, and is preferably added in the presence of an acid catalyst, preferably formic acid. The removal of the arylmethyl group in step (iv) is preferably a hydrogenolysis reaction conducted, e.g., in the presence of hydrogen gas and a platinum or palladium catalyst with or without carbon/charcoal, and in the presence of an acid catalyst.

The invention also relates to a novel process for the preparation of a compound of formula

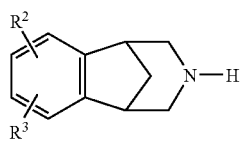

comprising the steps of
(i) hydrogenating a compound having the formula XXVIII or XXVIII':

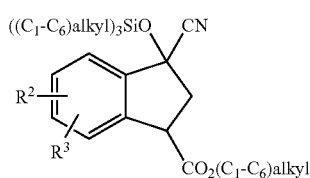

wherein $R^2$ and $R^3$ are defined above;
(ii) cyclizing the amine-ester compound of formula XXIX

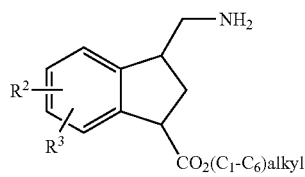

obtained from step (i) to form a lactam ring compound of formula XXX

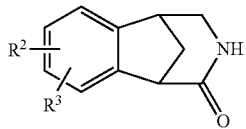

; and
(iii) reducing the carbonyl moiety.

The preferred starting material in step (i) is the trimethylsiloxy compound. The hydrogenation of step (i) is preferably conducted with a palladium or platinum catalyst under hydrogen gas, preferably in the presence of an acid catalyst. The lactam formation of step (ii) is preferably performed in the presence of a base, preferably an alkoxyalkalide compound in a nonaqueous protic solvent, more preferably sodium tert-butoxide in methanol. The reduction of step (iii) is preferably performed in the presence of a borane tetrahydrofuran complex, diborane, borane dimethysulfide complex, lithium aluminum hydride or a combination of sodium borohydride and boron trifluoride, more preferably a combination of sodium borohydride and boron trifluoride.

DETAILED DESCRIPTION OF THE INVENTION

Except where otherwise stated, $R^1$ through $R^{19}$, m, P and P', and structural formula I in the reaction schemes and discussion that follow are defined as above. Schemes 1–10, below, illustrate methods of synthesizing compounds of the formula I.

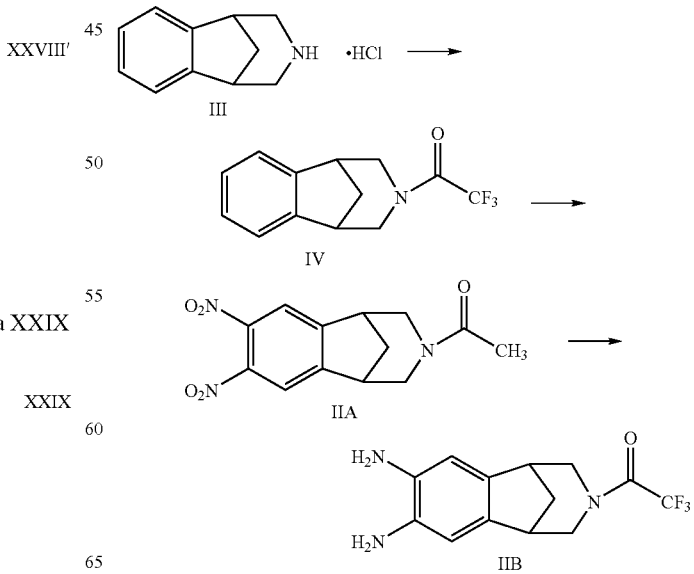

SCHEME 2
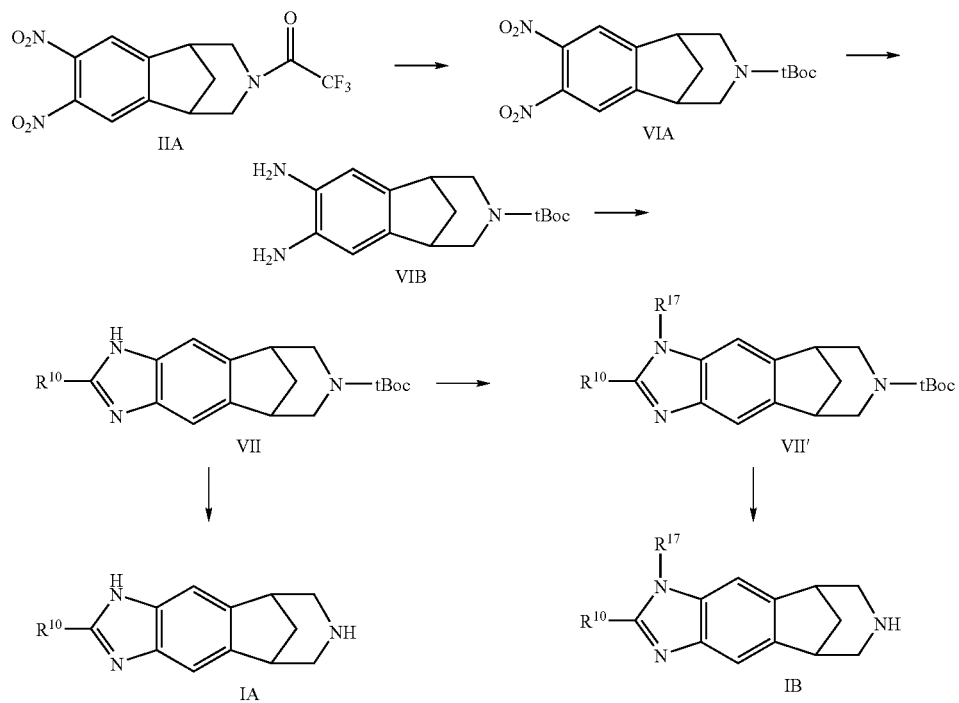
SCHEME 3
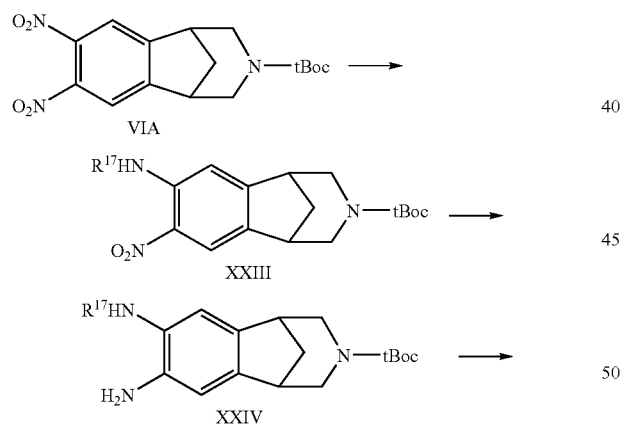
SCHEME 4
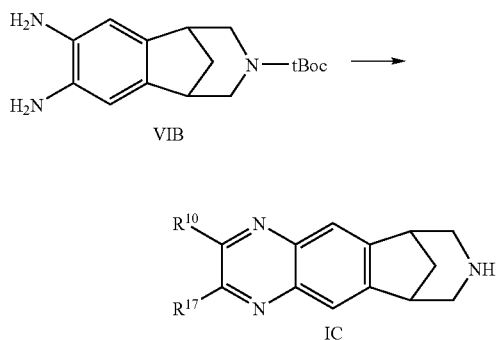
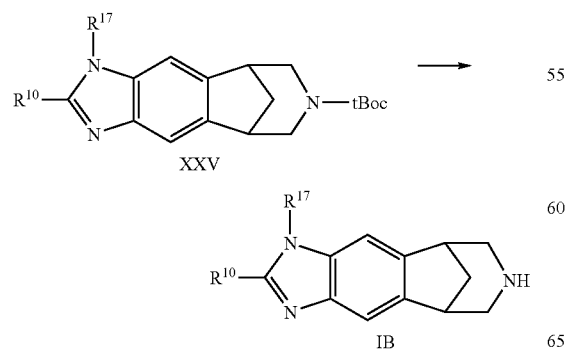
SCHEME 5
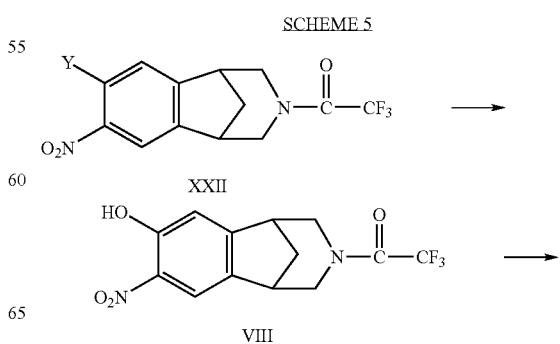

-continued

IE

SCHEME 6

III

IX

IX'

X

XI

IF

SCHEME 7

XII
(ring A = present or absent)

XIII
(ring A = present or absent)

XIIIA
(ring A = present or absent)

XIV
(ring A = present or absent)

IG: ($R^7$ and $R^3$ form ring A)
III: (ring A = absent)

SCHEME 7A

XXVI

XXVIIA

XXVIIIA

L is H— or $((C_1-C_6)alkyl)_3Si$—

XXIXA

-continued
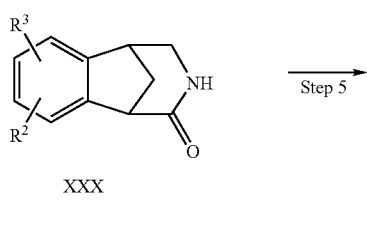
XXX
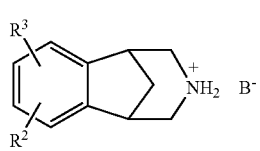
B⁻ is halide, tosylate, mesylate, ⁻OSO₂R² or ⁻OCOR²
IG': where R² and R³ form a ring A (See Scheme 7)
III': where R² and R³ do not form a ring
Step 5
-continued
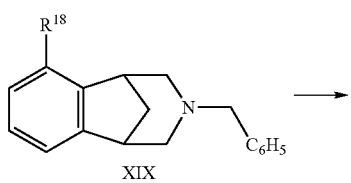
XIX
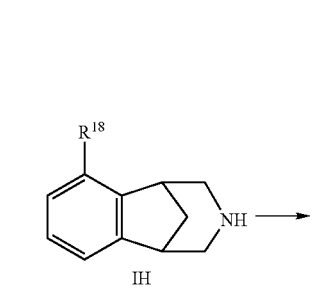
IH
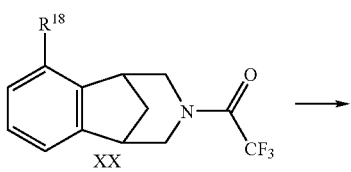
XX
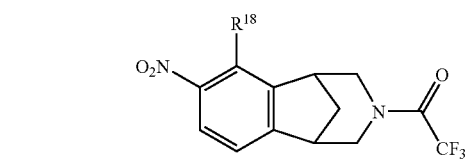
XXI
(R¹⁸ is, e.g., F, (C₁-C₆)alkoxy or any suitable R² and/or R³ groud member)
SCHEME 8
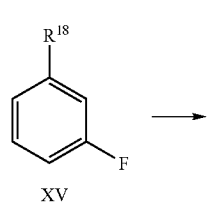
XV
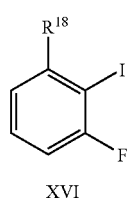
XVI
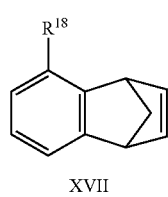
XVII
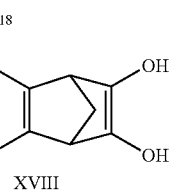
XVIII
SCHEME 8A
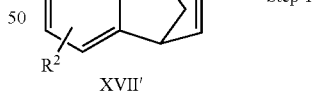
XVII'
Step 1
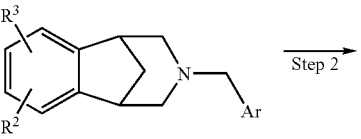
XIX'
Step 2
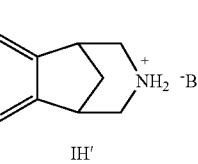
IH'

SCHEME 9

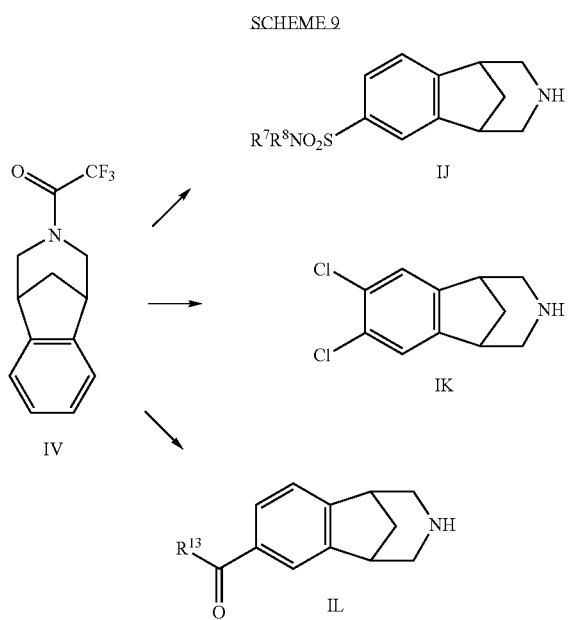

SCHEME 10

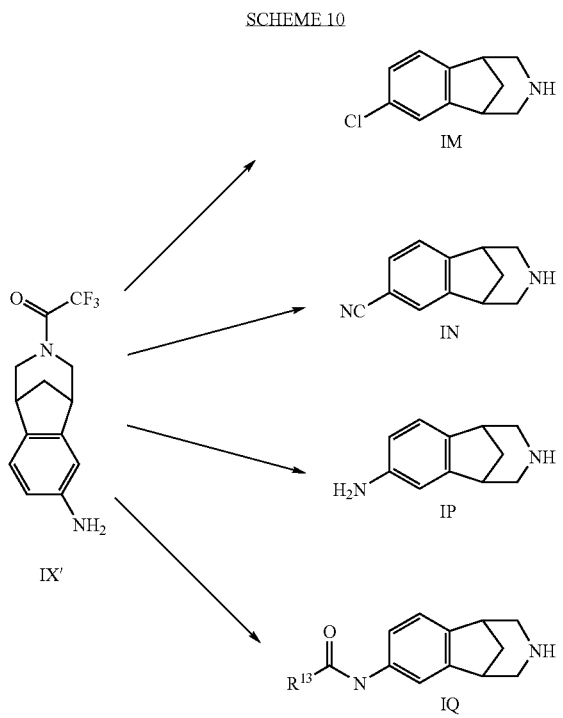

Referring to Scheme 1, the starting material of formula III is reacted with trifluoroacetic anhydride, in the presence of pyridine, to form the compound of formula IV. This reaction is typically conducted in methylene chloride at a temperature from about 0° C. to about room temperature. Other methods of generating a trifluoroacetate protecting group that may be used are recognized by those of skill in the art.

The compound of formula IV is then converted into the dinitro derivative of formula IIA by the following process. The compound of the formula IV is added to a mixture of 4 or more equivalents of trifluoromethanesulfonic acid ($CF_3SO_2OH$) and 2 to 3 equivalents of nitric acid, in a chlorinated hydrocarbon solvent such as chloroform, dichloroethane (DCE) or methylene chloride. The resulting mixture is allowed to react for about 5 to 24 hours. Both of the foregoing reactions are generally conducted at a temperature ranging from about −78° C. to about 0° C. for about 2 hours, and then allowed to warm to room temperature for the remaining time.

Reduction of the compound of formula IIA, using methods well known to those of skill in the art, yields the compound of formula IIB. This reduction can be accomplished, for example, using hydrogen and a palladium catalyst such as palladium hydroxide or palladium on carbon and running the reaction in methanol at about room temperature. The steps of Scheme 1 can also be performed with a nitrogen-protecting group, other than an a trifluoroacetyl group, that would be deemed suitable by those of skill in the art. Other suitable nitrogen protecting groups that can be used in the procedures described throughout this document include —$COCF_3$, —$COCCl_3$, —$COOCH_2CCl_3$, —$COO(C_1–C_6)alkyl$ and —$COOCH_2C_6H_5$. These groups may be added or removed by methods described for each in T. W. Greene and G. M. Wuts, *Protective Groups in Organic Synthesis* (John Wiley & Sons, New York, 1991).

Referring to Scheme 2, the compound of formula IIA is converted into the corresponding compound wherein the trifluoroacetyl protecting group is replaced by a t-Boc protecting group (VIA) by reacting it first with an alkali metal or alkaline earth metal (or ammonium) hydroxide or carbonate, and then reacting the isolated product from the foregoing reaction with di-t-butyldicarbonate. Although t-Boc is used in this instance, other appropriate nitrogen-protecting groups known to those of skill in the art may be used. The reaction with the alkali or alkaline earth metal (or ammonium) hydroxide or carbonate is generally carried out in an aqueous alcohol, dioxane or tetrahydrofuran (THF) at a temperature from about room temperature to about 70° C., preferably at about 70° C., for about one to about 24 hours. The reaction of the isolated, unprotected amine or an acid addition salt of such amine, from the above reaction with di-t-butyldicarbonate is preferably carried out in a solvent such as THF, dioxane or methylene chloride at a temperature from about 0° C. to about room temperature. This reaction may or may not be conducted in the presence of a base. When the reactant is a salt of the amine, use of a base is preferred. The resulting compound of formula VIA can be converted into the corresponding diamino derivative of formula VIB using the procedure described above for converting the dinitro compound of formula IIA into the corresponding diamino compound of formula IIB, or other generally accepted nitro group reduction methods known to those of skill in the art, e.g., zinc-, tin-, or iron-mediated reductions, etc.

The conversion of the compound of formula VIB into the desired compound of the formula VII can be accomplished by reacting the compound of formula VIB with a compound of the formula XXIIA

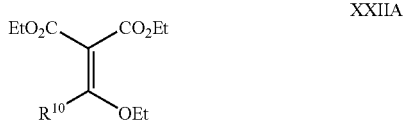

wherein $R^{10}$ is hydrogen, $(C_1-C_6)$alkyl optionally substituted with from one to seven fluorine atoms, aryl-$(C_0-C_3)$alkyl wherein said aryl is selected from phenyl and naphthyl, or heteroaryl-$(C_0-C_3)$alkyl wherein said heteroaryl is selected from five to seven membered aromatic rings containing from one to four heteroatoms selected from oxygen, nitrogen and sulfur, and wherein each of the foregoing aryl and heteroaryl groups may optionally be substituted with one or more substituents, preferably from zero to two substituents, independently selected from $(C_1-C_6)$alkyl optionally substituted with from one to seven fluorine atoms, $(C_1-C_6)$alkoxy optionally substituted with from one to seven fluorine atoms and cyano. The preferred solvent for this reaction is a 10:1 mixture of ethanol/acetic acid. The reaction temperature can range from about 40° C. to about 100° C. It is preferably about 60° C. Other appropriate solvents include acetic acid, ethanol and isopropanol.

Alternate methods of preparing compounds of the formula VII the compound of formula VIB are described by Segelstein et al., *Tetrahedron Lett.*, 1993, 34, 1897.

Removal of the t-Boc protecting group from the compound of formula VII yields corresponding compound of formula IA. The protecting group can be removed using methods well known to those of skill in the art. For example, the compound of formula VII can be treated with an anhydrous acid such as hydrochloric acid, hydrobromic acid, methanesulfonic acid, or trifluoroacetic acid, preferably hydrochloric acid in ethyl acetate, at a temperature from about 0° C. to about 100° C., preferably from about room temperature to about 70° C., for about one to 24 hours.

The compound of formula VII can be converted into the corresponding compound of formula IB by reacting it with a compound of the formula $R^{17}Z$, wherein $R^{17}$ is defined as $R^{10}$ is defined above, and Z is a leaving group such as a halo or sulfonate (e.g., chloro, bromo, mesylate or tosylate), in the presence of a base such as an alkali metal hydride, hydroxide or carbonate, preferably potassium hydroxide, in a polar solvent such as water, dimethylsulfoxide (DMSO), THF or DMF, preferably a mixture of DMSO and water, and then removing the protecting group as described above. The reaction with $R^{17}Z$ is generally carried out at a temperature from about room temperature to about 100° C., preferably at about 50° C., for about five hours.

Scheme 3 illustrates an alternate method of preparing compounds of the formula IB from the compound of formula VIA. This method is the preferred method of making compounds of the formula IB wherein $R^{17}$ is a bulky group such as an aryl or heteroaryl containing group, or when $R^{17}$ can not be attached, as illustrated in Scheme 2, by alkylation or aryl substitution methods. Referring to Scheme 3, the compound of formula VIA is reacted with the appropriate compound of formula $R^{17}NH_2$ in a polar solvent such as THF, DMF or DMSO, preferably THF, at a temperature from about room temperature to about 100° C., preferably at the reflux temperature, for about four to eighteen hours. The resulting compound of formula XXIII is then converted into the corresponding compound of the formula XXIV by reducing the nitro group to an amino group using methods well known to those of skill in the art. Such methods are referred to above for the conversion of the compounds of the formula IIA into a compound of the formula IIB in Scheme 1, and exemplified in experimental Examples 12B and 18B. Closure to the imidazole ring to form the corresponding compound of formula XXV can then be accomplished by reacting the compound of formula XXIV from the above reaction with a compound of the formula XXIIA:

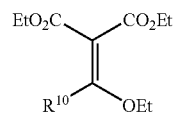

wherein $R^{10}$ is defined as above, as described above for converting compounds of the formula VIB into those of the formula VIII.

Removal of the protecting group from the compound of formula XXV yields the corresponding compound of formula IB. This can be accomplished using methods well known in the art, for example, as described above for forming compounds of the formula IA from the corresponding compounds of the formula VIII.

Scheme 4 illustrates a method of preparing compounds of the formula IC, wherein $R^{10}$ and $R^{17}$ are as defined above. Referring to Scheme 4, the compound of formula VIB, or analogously formula IIB in Scheme I, is reacted with a compound of the formula

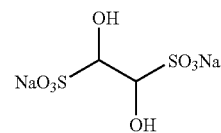

(sodium bisulfite ethane dione addition adduct) in water or another polar solvent such as THF, DMF or DMSO, preferably a mixture of water and a water miscible solvent such as THF, for about one to four hours. The reaction temperature can range from about 40° C. to about 100° C., and is preferably at about the reflux temperature.

Alternatively, the compound of formula VIB can be reacted with a compound of the formula

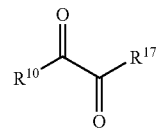

(double condensation reaction) in a polar solvent such as THF, water, or acetic acid, preferably a mixture of water and THF. This reaction is typically carried out at a temperature from about 40° C. to about 100° C., preferably at the reflux temperature, for about two to four hours. The desired quinoxoline of formula IC can then be formed by deprotecting the compound formed in either of the foregoing reactions, using the method described above for converting a compound of the formula VII into one of the formula IA. Alternatively, in place of compound VIB in Scheme 4, the compound IIB of Scheme 1 may be used analogously in this procedure with deprotection/reprotection as outlined in Scheme 2 (i.e., the process of transforming IIA to VIA) in order to arrive at ultimately the compound IC. In general, alternative nitrogen protection groups are equally suited to the procedure of Scheme 4.

Scheme 5 illustrates a method of preparing compounds of the formula I wherein $R^2$ and $R^3$, together with the benzo ring to which they are attached, form a benzoxazole ring system. Such a compound, wherein $R^1$ is hydrogen, is depicted in Scheme 5 as chemical formula IE. Referring to Scheme 5, the compound of formula XXII, wherein Y is nitro, halo, trifluoromethanesulfonate or a diazonium salt, is reacted with potassium acetate or another alkali or alkaline earth metal carboxylate in a solvent such as dimethylsulfoxide (DMSO), DMF or acetonitrile, preferably DMSO. This reaction is generally allowed to run for about 12–24 hours. Appropriate reaction temperatures range from about 70° C. to about 140° C. Approximately 100° C. is preferred.

The above reaction yields the compound of formula VIII, which can then be converted into the desired compound having formula IE by the following procedure. First, the compound of formula VIII is reduced by reaction with hydrogen and a palladium or platinum catalyst such as palladium hydroxide in methanol at a temperature from about 0° C. to about 70° C., preferably at about room temperature, to form the corresponding amino derivative. The product of this reaction is then reacted with an acid chloride of the formula $R^{10}COCl$ or an acid anhydride of the formula $(R^{10}CO)_2O$ wherein $R^{10}$ is $(C_1-C_6)$alkyl, or a compound of the formula $R^{10}C(OC_2H_5)_3$, in an appropriate inert solvent such as decalin, chlorobenzene or xylenes. A mixture of xylenes is preferred. This reaction is typically conducted at a temperature from about 120–150° C., preferably at about 140° C. When $R^{10}COCl$ is used as a reactant, it is preferable to add a stoichiometric amount of triethylamine (TEA) or another organic tertiary amine base and a catalytic amount of pyridinium p-toluenesulfonic acid or pyridinium p-toluenesulfonate (PPTs) to the reaction mixture. When $R_{10}C(OC_2H_5)_3$ is used as a reactant, it is preferable to add a catalytic amount of PPTs to the reaction mixture.

Removal of the trifluoroacetyl nitrogen protecting group yields the desired compound of the formula IE. This can be accomplished using methods well known to those of skill in the art, for example, reacting the protected compound with a lower alkanol and an aqueous alkali or alkaline earth metal (or ammonium) hydroxide or carbonate, aqueous sodium carbonate, at a temperature from about 50° C. to about 100° C., preferably at about 70° C., for about two to six hours.

Scheme 6 illustrates the preparation of compounds of the formula I wherein $R^1$ is hydrogen and $R^2$ and $R^3$, together with the benzo ring to which they are attached, form a benzothiazole ring system. Referring to Scheme 6, the compound of formula III is reacted with trifluoroacetic anhydride to form the corresponding compound wherein the ring nitrogen is protected by a trifluoroacetyl group, and the resulting nitrogen protected compound is then reacted with two equivalents of trifluoromethanesulfonic anhydride and one equivalent of nitric acid to form the corresponding compound of formula IX, wherein there is a single nitro substituent on the benzo ring. The reaction with trifluoroacetic acid is typically conducted in the presence of pyridine. Both of the above reactions are typically conducted in a reaction inert solvent such as a chlorinated hydrocarbon solvent, preferably methylene chloride, at a temperature from about 0° C. to about room temperature, preferably at about room temperature.

The above transformation can also be accomplished using other nitration methods known to those skill in the art. Reduction of the nitro group to an amine group can be accomplished as described above to provide a compound of the formula IX'.

The compound of formula IX' is then reacted with a carboxylic acid halide or anhydride of the formula $R^{10}COX$ or $(R^{10}CO)_2O$, wherein X is halo and $R^{10}$ is hydrogen or $(C_1-C_6)$alkyl, and pyridine, TEA or another tertiary amine base, to form a compound of the formula X, which can then be converted to the desired compound having formula XI by reacting it with Lawesson's reagent:

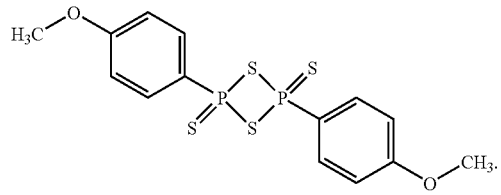

The reaction with $R^{10}COX$, wherein X is halo, or $(R^{10}CO)_2O$ is generally carried out at a temperature from about 0° C. to about room temperature, preferably at about room temperature. The reaction with Lawesson's reagent is generally carried out in a reaction inert solvent such as benzene or toluene, preferably toluene, at a temperature from about room temperature to about the reflux temperature of the reaction mixture, preferably at about the reflux temperature.

Closure to the benzothiazole ring and nitrogen deprotection to form the desired compound of formula IF can be accomplished by reacting the compound of formula XI with potassium ferricyanide and sodium hydroxide in a mixture of water and methanol (NaOH/$H_2O$/$CH_3OH$), at a temperature from about 50° C. to about 70° C., preferably at about 60° C. for about 1.5 hours.

Scheme 7 illustrates a method of preparing the compound of formula III, which is used as the starting material for the process of Scheme 1, or a compound of the formula IG, wherein $R^2$ and $R^3$ form a ring (labeled "A" in the Scheme), as defined above in the definition of compounds of the formula I. Referring to Scheme 7, the compound of formula XII, wherein $X^1$ and $X^2$ are selected, independently, from chloro, fluoro, bromo and iodo, but where at least one of $X^1$ and $X^2$ is Br— or I—, reacted with cyclopentadiene, in the presence of magnesium metal, in a THF, dioxane or other ethereal solvent, at a temperature from about 40° C. to about 100° C., preferably at about the reflux temperature, to form a compound of the formula XIII. Reaction of the resulting compound of formula XIII with N-methylmorpholine-N-oxide (NMO) and osmium tetroxide in acetone at about room temperature yields the corresponding compound of the formula XIIIA.

The compound having formula XIIIA is then converted into the corresponding compound of formula XIV using the following procedure. First, the compound of formula XIIIA is reacted with sodium periodate in a mixture of a chlorinated hydrocarbon, preferably dichloroethane (DCE), and water, or with lead tetraacetate in a chlorinated hydrocarbon solvent, at a temperature from about 0° C. to about room temperature, to generate a dialdehyde or glycal intermediate. The product of this reaction is then reacted with benzylamine and sodium triacetoxyborohydride in a chlorinated hydrocarbon solvent at a temperature from about 0° C. to about room temperature, preferably at about room temperature, to form the desired compound of formula XIV. Removal of the benzyl group from the compound of formula XIV yields the compound of formula III (when ring A is absent) or IG, (when ring A is present). This can be accomplished using methods well known to those of skill in the art, for example, optionally reacting the free base with one equivalent of acid, e.g., hydrochloric acid, (to form the corresponding acid addition salt), followed by hydrogenolysis and palladium hydroxide in methanol at about room temperature.

In the reductive animation step described above and throughout this document, alternatives to benzyl amine, such as ammonia, hydroxylamine, alkoxy amines, methyl amine, allyl amine, and substituted benzylamines (e.g., diphenylmethyl amine and 2- and 4-alkoxy substituted benzyl amines) can also be used. They can be used as free bases, or as their salts, preferably their acetate salts, and can be subsequently removed by methods described for each in T. W. Greene and G. M. Wuts, *Protective Groups in Organic Synthesis* (John Wiley & Sons, New York 1991).

The procedure of Scheme 7 can also be used to prepare compounds of the formula I wherein $R^2$ and $R^3$ do not form a ring and are not both hydrogen, by replacing the starting material of formula XII with the appropriate compound having the formula XII'

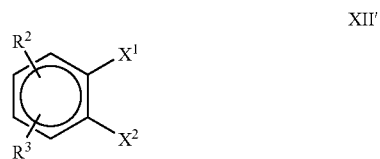

XII'

Alternatively, a compound of formula XIII can be converted, via methods described below and in Scheme 8, to compounds of formula XIV or formula IG or formula III.

An alternative means of preparing a compound of formula III', or as appropriate IG', is illustrated in Scheme 7A. This process can be applied to produce compounds of compounds of formula I, where $R^1$ is hydrogen, and $R^2$ and $R^3$ are as defined above, with the exception of when $R^2$ and $R^3$ are hydroxy, amino, $(C_1-C_6)$alkylamino, $((C_1-C_6)$alkyl$)_2$amino, —C(=O)$R^{13}$, or —$(C_1-C_6)$alkylene-C(=O)$R^{13}$.

Referring to Scheme 7A, step 1 of is an esterification of a carboxylic acid. A carboxylic acid of formula XXVI is treated with a Lewis acid catalyst such as boron trifluoride, or with an acid catalyst such as sulfuric acid, hydrochloric acid, p-toluenesulfonic acid, methane sulfonic acid, trifluoroacetic acid, or hydrobromic acid, preferably sulfuric acid, in an alcohol solvent such as methanol, ethanol, propanol, butanol, pentanol, or hexanol, preferably methanol, at a temperature between 25 and 120° C., preferably 65° C., for a period of 30 minutes to 24 hours, preferably 4 hours, to afford a compound of formula XXVIIA.

Step 2 of Scheme 7A is a cyanohydrin formation. A ketone of formula XXVIIA is treated with a Lewis acid catalyst such as zinc iodide, zinc triflate, trimethylsilyl triflate, trimethylsilyl iodide, aluminum chloride, tin (II) chloride, or trimethyl aluminum, preferably zinc iodide, or with catalytic potassium cyanide and 18-crown-6, and trimethylsilyl cyanide, in a solvent such as acetonitrile, toluene, methylene chloride, ethyl acetate, isopropyl acetate, methyl-tert-butyl ether, or tetrahydrofuran, preferably a mixture of acetonitrile and toluene, at a temperature between 0 and 100° C., preferably at 50° C., for a period of time between 1 and 24 hours, preferably 5 hours, to afford a compound of formula XXVIIIA.

Step 3 of Scheme 7A is a hydrogenolysis reaction. A nitrile of formula XXVIIIA is treated with an acid catalyst such as p-toluenesulfonic acid, methane sulfonic acid, hydrochloric acid, sulfuric acid, phosphoric acid, or trifluoroacetic acid, preferably p-toluenesulfonic acid, and a palladium catalyst such as palladium on carbon or palladium hydroxide on carbon, preferably palladium hydroxide on carbon, in a solvent such as methanol, ethanol, isopropanol, butanol, propanol, ethyl acetate, isopropyl acetate, or toluene, preferably methanol, under a hydrogen pressure of 15 to 100 psi, preferably 50 psi, for a time period between 2 and 72 hours, preferably 24 hours, to afford a compound of formula XXIXA.

Step 4 of Scheme 7A is an amide formation. An amine of formula XXIXA is treated with a base such as sodium tert-butoxide, sodium methoxide, sodium ethoxide, sodium hydroxide, potassium tert-butoxide, potassium methoxide, potassium ethoxide, potassium hydroxide, sodium carbonate, potassium carbonate, cesium carbonate, sodium hydride, triethylamine, methylimidazole, lutidine, pyridine, methylmorpholine, ethylmorpholine, or diisopropylethylamine, preferably sodium tert-butoxide, in a solvent such as methanol, ethanol, isopropanol, ethyl acetate, acetonitrile or toluene, preferably methanol, at a temperature between 0 and 120° C., preferably 65° C., for a time period between 30 minutes and 72 hours, preferably 2 hours, to afford a compound of formula XXX.

Step 5 of Scheme 7A is a reduction of an amide. An amide of formula XXX is treated with a reducing agent such as borane tetrahydrofuran complex, diborane, borane dimethylsulfide complex, lithium aluminum hydride, or a combination of sodium borohydride and boron trifluoride, preferably a combination of sodium borohydride and boron trifluoride, in a solvent such as tetrahydrofuran, 1,2-dimethoxyethane, 1,2-diethoxyethane, diisopropyl ether, 1,4-dioxane, or methyl-tert-butyl ether, preferably tetrahydrofuran, at a temperature between 0 and 80° C., preferably 50° C., for time period between 1 and 24 hours, preferably 5 hours. The product is isolated by crystallization as a salt of an acid such as p-toluenesulfonic acid, methane sulfonic acid, hydrochloric acid, oxalic acid, citric acid or acetic acid, preferably p-toluenesulfonic acid, in a solvent such as isopropanol, hexane, acetone, ethyl acetate, methyl ethyl ketone, or toluene, preferably isopropanol, to afford the salt form of compound of formula IG or III.

Scheme 8, 9 and 10 illustrate methods of preparing compounds of the formula I wherein $R^1$ is hydrogen, and $R^2$ and $R^3$ represent a variety of different substituents, as defined above, but do not form a ring.

Scheme 8 illustrates a variation of the process shown in Scheme 7, which can be used to make a compound identical to that of formula III except that the benzo ring is substituted with a fluoro group, an alkoxy group or any other suitable $R^2$ and/or $R^3$ group ($R^{18}$ in Scheme 8). This compound is depicted in Scheme 8 as chemical structure 1H. Referring to Scheme 8, where, for example, $R^{18}$ is F, 1,3-difluorobenzene is reacted with a strong base such as an alkali metal dialkylamine or an alkali metal alkyl (or aryl) in an ethereal solvent such as ethyl ether or THF, at a temperature below −50° C., followed by quenching with iodine or N-iodosuccinamide, to form 1,3-difluoro-2-iodobenzene. The compound 1,3-difluoro-2-iodobenzene (structural formula XVI in Scheme 8) is then converted into the compound of formula IH by a series of reactions (represented in Scheme 8 as XVI→XVII→XVIII→XIX→IH) that are analogous to the series of reactions described above and illustrated in Scheme 7 or Scheme 8A for converting compounds of the formula XIII into those of the formula IG or III. Conversion of the compound of formula XVI into the compound of formula XVII can also be accomplished by treating a mixture of the compound of formula XVI and cyclopentadiene with an alkyl lithium reagent, preferably n-butyl lithium, in an inert hydrocarbon solvent such as petroleum ether, toluene or methyl cyclohexane, at a temperature from about −20° C. to about room temperature, preferably at about 0° C. This procedure is equally effective to effect the conversion as set forth in Scheme 7 with or without the $R^{18}$ group present.

The compound of formula IH can then be converted into the corresponding nitrogen protected derivative of formula XX, using the methods described above for synthesizing the compound of formula IV in Scheme 1. Nitration of the compound of formula XX using the method described above for preparing the compound of formula IX in Scheme 6, yields the compound of formula XXI wherein the benzo ring is substituted with both a fluoro and nitro group, an alkoxy group and nitro group, or an $R^{18}$ substituent and a nitro group. The compound of formula XXI can be used to make a variety of compounds of the formula I wherein one of $R^2$ and $R^3$ is fluoro, using methods that are well known to those of skill in the art, for example, by first converting the nitro group to an amino group, converting the amino group to a variety of other substituents, as illustrated in Scheme 10, and then removing the nitrogen protecting group.

The compound of formula XXI acts as a regioisomeric functional equivalent of the compounds having formulas IIA, VIA and XXII, in that the fluorine atom of formula XXI reacts similarly to the nitro and Y groups of formula IIA, VIA, and XXII, and thus can be subjected to the same series of reactions as those described above for the latter three compounds, providing an alternate means for preparing the products of such reactions. Similarly, the alkoxy group of formula XXI ($R^{18}$=alkoxy) may be converted into a hydroxyl group before or after introduction of the nitro group, and then converted to isomeric products as described above. Also, the trifluoromethanesulfonate ester of such hydroxy derivative can act as a Y-group as described.

Preparation of compounds of formula I where $R^2$=—O ($C_1$–$C_6$)alkyl, ($C_1$–$C_6$) alkyl or aryl wherein aryl is defined as above in the definition of formula I, and $R^3$ is H or one of the other substituents described above in the definition of formula I, can be prepared as described above and illustrated in Scheme 8 by replacing one of the fluorine atoms of the compound of formula XV with —O—($C_1$–$C_6$)alkyl, ($C_1$–$C_6$)alkyl or aryl, respectively.

Scheme 8A illustrates an alternative procedure for obtaining compounds of formula I, where $R^2$ and $R^3$ are as defined above, with the exception of ($C_2$–$C_6$)alkenyl, ($C_2$–$C_6$)alkynyl or nitro (1H', as depicted). Step 1 of Scheme 8A is an oxidation followed by a reductive amination. A benzonorbornadiene derivative of formula XVII' is first treated with ozone until the solution develops a blue color between 0° C. and −78° C., preferably −78° C., in a solvent such as methanol, or dichloromethane, preferably methanol. The ozonide formed is reduced by hydrogenolysis between −78° C. and room temperature, preferably between 0° C. and room temperature, with platinum or palladium catalyst such as platinum oxide, platinum on carbon, palladium on carbon, or palladium hydroxide on carbon, preferably 5% platinum on carbon, for a period of time between 5 minutes and 6 hours, preferably 1 hour, under a hydrogen atmosphere between 15 and 100 psi, preferably between 30 and 50 psi. Next, an arylmethylamine, such as benzylamine, 4-methoxybenzylamine, or 3,4-dimethoxybenzylamine, preferably benzylamine is added to the reaction mixture at room temperature with an acid catalyst such as formic acid, acetic acid, p-toluenesulfonic acid, oxalic acid, or hydrochloric acid, preferably formic acid, and hydrogenolysis is resumed for a period of time between 1 and 12 hours, preferably 4 hours, at a hydrogen pressure between 15 and 100 psi, preferably 50 psi, to afford a compound of formula XIX', where Ar is an aryl group.

Step 2 of Scheme 8A is a hydrogenolysis reaction. A compound of formula II is treated with an acid such as p-toluenesulfonic acid, hydrochloric acid, sulfuric acid, acetic acid, formic acid, or methane sulfonic acid, preferably p-toluenesulfonic acid, and a palladium catalyst such as palladium hydroxide on carbon or palladium on carbon, preferably palladium hydroxide on carbon, in a solvent such as methanol, ethanol, isopropanol, ethyl acetate, or methyl acetate, preferably methanol, under a hydrogen pressure between 15 and 100 psi, preferably 50 psi, at a temperature between room temperature and 60° C., preferably 40° C., for a period of time between 1 and 48 hours, preferably 15 hours. The product is crystallized as a salt depending on which acid catalyst is used in a solvent such as isopropanol, hexane, acetone, ethyl acetate, methyl ethyl ketone, or toluene, preferably in a mixture of isopropanol and hexane, to afford a compound of formula IH'.

Scheme 9 illustrates methods of preparing compounds of the formula I wherein: (a) $R^1$ is hydrogen and $R^2$ is $R^7R^8NO_2S$—; (b) $R^1$ and $R^2$ are both chloro; and (c) $R^1$ is hydrogen and $R^2$ is $R^{13}C(=O)$—. These compounds are referred to in Scheme 9, respectively, as compounds of formulas IJ, IK and IL.

Referring to Scheme 9, compounds of the formula IJ can be prepared by reacting the compound of formula IV with two or more equivalents of a halosulfonic acid, preferably chlorosulfonic acid, at a temperature from about 0° C. to about room temperature. Reaction of the chlorosulfonic acid derivative so formed with an amine having the formula $R^7R^8NH$, wherein $R^7$ and $R^8$ are defined as above, followed by removal of the nitrogen protecting group, yields the desired compound having formula IJ.

Compounds of the formula IK can be prepared by reacting the compound of formula IV with iodine trichloride in a chlorinated hydrocarbon solvent, followed by removal of the nitrogen protecting group. The reaction with iodine trichloride is typically carried out at a temperature from about 0° C. to about room temperature, and is preferably carried out at about room temperature. In a similar fashion, the analogous mono- or di-brominated or mono- or di-iodinated compounds can be prepared by reacting the compound of IV with N-iodosuccinamide or N-bromosuccinimide in a trifluoromethanesulfonic acid solvent, followed by removal of the nitrogen protecting group as described above.

Reaction of the compound of IV with an acid halide of the formula $R^{13}COCl$ or an acid anhydride of the formula ($R^{13}CO)_2O$, with or without a reaction inert solvent such as a chlorinated hydrocarbon solvent, preferably methylene chloride, in the presence of Lewis acid such as aluminum chloride, at a temperature from about 0° C. to about 100° C., followed by nitrogen deprotection, yields the compound of formula IL. The reaction with the acid halide or anhydride can be carried out using other known Lewis acids or other Friedel-Crafts acylation methods that are known in the art.

The reactions described herein in which —$NO_2$, —$SO_2NR^7R^8$, —$COR^3$, I, Br or Cl are introduced on the compound of formula IV, as depicted in Scheme 9 and described above, can be performed on any analogous compound wherein $R^2$ is hydrogen, ($C_1$–$C_6$)alkyl, halo, ($C_1$–$C_6$) alkoxy or —$NHCONR^7R^8$, producing compounds of the formula I wherein $R^2$ and $R^3$ are defined as in the definition of compounds of the formula I above.

Compounds that are identical to those of the formula IL, but which retain the nitrogen protecting group, can be converted into the corresponding O-acyl substituted compounds, i.e., those wherein the —C(═O)$R^{13}$ group of formula IL is replaced with a —O—C(═O)$R^{13}$ group, using Baeyer-Villiger processes well known to those skilled in the art. The resulting compounds can be partially hydrolyzed, as described in Example 35, to yield the corresponding hydroxy substituted compounds, and then alkylated to form the corresponding alkoxy substituted compounds. Also, as described in Example 36, such O-acyl substituted compounds can be used to prepare variably substituted benzisoxazoles.

Scheme 10 illustrates methods of making compounds of the formula I wherein: (a) $R^1$ is hydrogen and $R^2$ is chloro; (b) $R^1$ is hydrogen and $R^2$ is cyano; (c) $R^1$ is hydrogen and $R^2$ is amino; and (d) $R^1$ is hydrogen and $R^2$ is $R^{13}$C(═O)N(H)—. These compounds are referred to in Scheme 10, respectively, as compounds of the formula IM, IN, IP and IQ.

Compounds of formula IM can be prepared from compounds of the formula IX' by generation of a diazonium salt with, for instance, an alkali metal nitrite and strong mineral acid (e.g., hydrochloric acid, sulfuric acid, hydrobromic acid) in water, followed by reaction with a copper halide salt, such as copper (I) chloride. Nitrogen deprotection by the methods described above yields the desired compound of formula IM. Alternative methods for the generation of diazonium salts, as known and practiced by those of skill in the art, can also be used. The foregoing reaction is generally carried out by temperatures ranging from about 0° C. to about 60° C., preferably about 60° C. for about 15 minutes to one hour.

Reaction of the diazodium salt, prepared as described above, with potassium iodide in an aqueous medium provides the analogous iodide derivative. This reaction is generally carried out at a temperature from about 0° C. to about room temperature, preferably at about room temperature. The resulting compound, or its analogous N-tert-butylcarbonate protected form, can be used to prepare the corresponding cyano derivative by reaction with copper (I) cyanide and sodium cyanide in DMF, N,N-dimethylpropylurea (DMPU) or DMSO, preferably DMF, at a temperature from about 50° C. to about 180° C., preferably about 150° C. Nitrogen deprotection as described above provides the desired compound of formula IM.

The above described iodide derivative can also be used to access a variety of other substituents such as aryl, acetylene and vinyl substituents, as well as the corresponding carbonyl esters and amides, by palladium and nickel catalyzed processes known to those of skill in the art, such as Heck, Suzuki and Stille couplings and Heck carbonylations. These compounds and others, wherein $R^2$ is halo, alkyl, alkoxy, etc., may be similarly functionalized to generate compounds wherein $R^2$ and $R^3$ are as defined above.

Nitrogen deprotection of the compound of formula IX' provides the compound of the formula IP. The compound of formula IX' can be reacted with a acyl group having the formula $R^{13}$COCl or $(R^{13}CO)_2O$ using the methods described above, followed by nitrogen deprotection to provide compounds of the formula IQ. In a similar fashion, treatment of the protected amine with a compound having the formula $R^{13}SO_2X$, when X is chloro or bromo, followed by nitrogen deprotection, provides the corresponding sulfonamide derivative.

As noted above, suitable amine protecting groups that can be used, alternatively, in the procedures described throughout this document include —COCF$_3$, —COCCl$_3$, —COOCH$_2$CCl$_3$, —COO(C$_1$–C$_6$)alkyl and —COOCH$_2$C$_6$H$_5$. These groups may be removed by methods described for each in Greene et al.'s *Protective Groups in Organic Chemistry*, referred to above. Instances where protecting groups would be modified under the reaction conditions, such as, e.g., a —COOCH$_2$C$_6$H$_5$ group during nitration, still permit said procedures to operate as described with said modified protecting group. Modifying the order of protecting group incorporation and/or methods of functional group introduction or modification may also be applied where appropriate.

In each of the reactions discussed above, or illustrated in Schemes 1–10, above, pressure is not critical unless otherwise indicated. Pressures from about 0.5 atmospheres to about 5 atmospheres are generally acceptable, with ambient pressure, i.e., about 1 atmosphere, being preferred as a matter of convenience.

The compounds of the formula I and their pharmaceutically acceptable salts (hereafter "the active compounds") can be administered via either the oral, transdermal (e.g., through the use of a patch), intranasal, sublingual, rectal, parenteral or topical routes. Transdermal and oral administration are preferred. These compounds are, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds topically and this can be done by way of creams, a patch, jellies, gels, pastes, ointments and the like, in accordance with standard pharmaceutical practice.

Biological Assay

The effectiveness of the active compounds in suppressing nicotine binding to specific receptor sites is determined by the following procedure which is a modification of the methods of Lippiello, P. M. and Fernandes, K. G. (in *The Binding of L-[$^3$H]Nicotine To A Single Class of High-Affinity Sites in Rat Brain Membranes, Molecular Pharm.*, 29, 448–54, (1986)) and Anderson, D. J. and Arneric, S. P. (in *Nicotinic Receptor Binding of $^3$H-Cystisine, $^3$H-Nicotine and $^3$H-Methylcarmbamylcholine In Rat Brain, European J. Pharm.*, 253, 261–67 (1994)).

Procedure

Male Sprague-Dawley rats (200–300 g) from Charles River were housed in groups in hanging stainless steel wire cages and were maintained on a 12 hour light/dark cycle (7 a.m.–7 p.m. light period). They received standard Purina Rat Chow and water ad libitum.

The rats were killed by decapitation. Brains were removed immediately following decapitation. Membranes were prepared from brain tissue according to the methods of Lippiello and Fernandez (*Molec Pharmacol*, 29, 448–454, (1986) with some modifications. Whole brains were removed, rinsed with ice-cold buffer, and homogenized at 0° in 10 volumes of buffer (w/v) using a Brinkmann Polytron™, setting 6, for 30 seconds. The buffer consisted of 50 mM Tris HCl at a pH of 7.5 at room temperature. The homogenate was sedimented by centrifugation (10 minutes; 50,000×g; 0 to 4° C. The supernatant was poured off and the membranes were gently resuspended with the Polytron and centrifuged again (10 minutes; 50,000×g; 0 to 4° C. After the second centrifugation, the membranes were resuspended in assay buffer at a concentration of 1.0 g/100 mL. The composition of the standard assay buffer was 50 mM Tris HCl, 120 mM NaCl, 5 mM KCl, 2 mM MgCl$_2$, 2 mM CaCl$_2$ and has a pH of 7.4 at room temperature.

Routine assays were performed in borosilicate glass test tubes. The assay mixture typically consisted of 0.9 mg of membrane protein in a final incubation volume of 1.0 mL. Three sets of tubes were prepared wherein the tubes in each set contained 50 µL of vehicle, blank, or test compound solution, respectively. To each tube was added 200 µL of [$^3$H]-nicotine in assay buffer followed by 750 µL of the membrane suspension. The final concentration of nicotine in each tube was 0.9 nM. The final concentration of cytisine in the blank was 1 µM. The vehicle consisted of deionized water containing 30 µL of 1 N acetic acid per 50 mL of water. The test compounds and cytisine were dissolved in vehicle. Assays were initiated by vortexing after addition of the membrane suspension to the tube. The samples were incubated at 0 to 4° C. in an iced shaking water bath. Incubations were terminated by rapid filtration under vacuum through Whatman GF/B™ glass fiber filters using a Brandel™ multi-manifold tissue harvester. Following the initial filtration of the assay mixture, filters were washed two times with ice-cold assay buffer (5 m each). The filters were then placed in counting vials and mixed vigorously with 20 ml of Ready Safe™ (Beckman) before quantification of radioactivity. Samples were counted in a LKB Wallach Rackbeta™ liquid scintillation counter at 40–50% efficiency. All determinations were in triplicate.

Calculations

Specific binding (C) to the membrane is the difference between total binding in the samples containing vehicle only and membrane (A) and non-specific binding in the samples containing the membrane and cytisine (B), i.e., Specific binding=$(C)=(A)-(B)$.

Specific binding in the presence of the test compound (E) is the difference between the total binding in the presence of the test compound (D) and non-specific binding (B), i.e., (E)=(D)−(B).

% Inhibition=$(1-((E)/(C)))$ times 100.

The compounds of the invention that were tested in the above assay exhibited IC$_{50}$ values of less than 10 µM.

The following experimental examples illustrate, but do not limit the scope of, this invention.

EXAMPLE 1

10-AZA-TRICYCLO[6.3.1.0$^{2,7}$]DODECA-2(7), 3,5-TRIENE

A) 1,4-Dihydro-1,4-methano-naphthalene (Based wholly or in part on a) Wittig, G.; Knauss, E. *Chem. Ber.* 1958, 91, 895. b) Muir, D. J.; Stothers, J. B. *Can. J. Chem.* 1993, 71, 1290.)

Magnesium turnings (36.5 g, 1.5 M) were stirred in anhydrous THF (250 mL) in a dried 2 L 3 neck round bottom flask equipped with a 250 mL non-equalizing addition funnel with a nitrogen (N$_2$) flow adapter, mechanical stirrer and efficient condenser equipped with a N$_2$ flow adapter. The flask was stirred and warmed to reflux by a removable heating mantle. 2-Fluorobromobenzene (2 g) was added followed by 1 mL of 3N ethylmagnesium bromide (EtMgBr in THF). The addition funnel was charged with a mixture of cyclopentadiene (94.4 g, 1.43 M, Prepared by the method described in *Org. Syn. Col.*, Vol. V, 414–418) and bromofluorobenzene (250 g, 1.43 M) which was maintained at 0° C. in a separate flask by an ice bath, and transferred to the addition funnel via cannula. Small portions (~1 mL) of the intimate mixture were introduced to assist initiation (~4 times). After ~15 minutes, the reaction initiated (exothermic, vapor condensation), the heating mantle was removed and the contents of the addition funnel was added dropwise at such rate as to maintain reflux (1.5 hours). The heating mantle was re-applied and a reflux maintained for 1.5 hours. (TLC 100% hexanes $R_f$ 0.67).

The reaction was cooled to room temperature and quenched with $H_2O$ (500 mL) and carefully with 1N HCl (200 mL, produces $H_2$ evolution from unconsumed Mg). To this ~50 mL concentrated HCl was added to dissolve solids. Total addition/quench time ~1 hour. Saturated aqueous sodium chloride (NaCl) solution (300 mL) was added and product hexanes extracted until no potassium permanganate ($KMnO_4$) active product is removed. (4×~250 mL). The combined organic layer was washed with saturated $NaHCO_3$ solution (250 mL), sodium bicarbonate $Na_2SO_4$ dried and concentrated to an oil (~200 g). The product was distilled at 78–83° C. at 15 mm (131 g, 64%). (An alternative work-up is described on p. 419 Fieser and Fieser, Vol. I, Reagents for Organic Synthesis, Wiley, NY., NY.; 1967).

B) 1,2,3,4-Tetrahydro-1,4-methano-naphthalene-2,3-diol (Except for the work-up method and the quantity of $OsO_4$ used, based on VanRheenen, V.; Cha, D. Y.; Hartley, W. M. Org. Syn. 1988, 6, 342.)

In a 2 L 3 neck round bottom flask equipped with a $N_2$ flow adapter, mechanical stirrer was placed 1,4-dihydro-1,4-methano-naphthalene (79.5 g, 560 mmol) stirred in acetone (800 mL) and $H_2O$ (100 mL) and N-methyl morpholine N-oxide (67.5 g, 576 mmol). To this was added osmium tetroxide ($OsO_4$) (15 mL of a 15 mol % t-butyl alcohol solution, 1.48 mmol, 0.26 mol %) and the mixture was stirred vigorously. After 60 hours, the reaction was filtered, and the white product rinsed with acetone and air dried (60.9 g). The mother liquor was concentrated to an oily solid: acetone trituration, filtration and acetone rinse provided (27.4 g, total 88.3 g, 89%). (TLC 50% ethyl acetate/hexanes $R_f$~0.5). M.p. 176–177.5° C.

C) 10-Benzyl-10-aza-tricyclo[6.3.1.0$^{2,7}$]dodeca-2(7),3,5-triene (Based on Abdel-Magid, A. F.; Carson, K. G.; Harris, B. D.; Maryanoff, C. A.; Shah, R. D. J. Org. Chem. 1996, 61, 3849; and Mazzocchi, P. H.; Stahly, B. C. J. Med. Chem. 1979, 22, 455.)

1,2,3,4-Tetrahydro-1,4-methano-naphthalene-2,3-diol (40 g, 227.3 mmol) was stirred in $H_2O$ (1050 mL) and 1,2-dichloroethane (DCE) (420 mL) in a 2 L round bottom flask under nitrogen with cool water bath (~10° C.). To this sodium periodate ($NaIO_4$) (51 g, 239 mmol) and triethylbenzyl ammonium chloride ($Et_3BnNCl$) (50 mg) were added. The resulting mixture was stirred for 1 hour (slight initial exotherm), then the layers were separated and the aqueous layer was extracted with DCE (200 mL). The organic layer was washed with $H_2O$ (4×200 mL, or until no reaction to starch iodide is observed in the aqueous wash) then dried through a cotton plug. To this was added benzyl amine (25.5 g, 238.6 mmol) and the mixture was stirred for 2 minutes then immediately transferred into the sodium triacetoxyborohydride $NaHB(OAc)_3$/DCE (see below) over 10 minutes.

In a separate 2 L round-bottomed flask under nitrogen was magnetically stirred $NaHB(OAc)_3$ (154 g, 0.727 mmol) in DCE (800 mL) at 0° C. (ice bath). To this was added the above mixture over 10 minutes, without delay after the dialdehyde and amine were mixed. The resulting orange mixture was allowed to warm to room temperature and stirred for 30–60 minutes.

The reaction was quenched by addition of saturated sodium carbonate ($Na_2CO_3$) solution (~300 mL) carefully at first and the mixture was stirred for 1 hour (pH 9). The layers were separated and the aqueous layer was extracted with $CH_2Cl_2$ (2×300 mL). The organic layer was washed with saturated aqueous NaCl solution (200 mL), dried through a cotton plug, then evaporated to a red oil. This was dissolved in a minimum of $Et_2O$ and filtered through a Silica pad (3×4 inch) eluting with 15% ethyl acetate (ethyl acetate)/hexanes +1% of 37% aqueous ammonium hydroxide ($NH_4OH$) solution to remove baseline red color. Concentration affords a light yellow oil (48.5 g, 194.8 mmol, 85.7%). (TLC 10% ethyl acetate/hexanes $R_f$ 0.75). $^1H$ NMR (400 MHz, $CDCl_3$) δ 7.16 (m, 7H), 6.89 (m, 2H), 3.48 (m, 2H), 3.08 (m, 2H), 2.80 (d, J=9.5 Hz, 2H), 2.42 (d, J=9.5 Hz, 2H), 2.27 (m, 1H), 1.67 (d, J=10.0 Hz, 1H). APCI MS m/e 250.3 [(M+1)$^+$].

D) 10-Aza-tricyclo[6.3.1.0$^{2,7}$]dodeca-2(7),3,5-triene (For an alternative synthesis, see; Mazzocchi, P. H.; Stahly, B. C. J. Med. Chem. 1979, 22, 455.)

10-Benzyl-10-aza-tricyclo[6.3.1.0$^{2,7}$]dodeca-2(7),3,5-triene (70.65 g, 284 mmol) was stirred in ethyl acetate (250 mL) and treated with 3N HCl ethyl acetate (1.03 eq.) slowly with cooling (ice bath). The resulting precipitate was filtered and rinsed with ethyl acetate. The solids were dissolved in methanol (250 mL) in a Parr bottle. To this was added $Pd(OH)_2$ (7 g of 20% wt/C) and the mixture was shaken under 50–40 psi of $H_2$ for 24 hours or until done by TLC. The reaction was filtered through a Celite pad and concentrated to an oily solid. This was azeotroped with methanol (methanol) (3 times) then triturated with acetone, treated with ethyl ether ($Et_2O$) to precipitate product and filtered. Concentration of the mother liquors and a second treatment provided an off white solid (48.95 g, 251 mmol, 88%). (TLC 10% methanol/$CH_2Cl_2$ ($NH_3$) $R_f$ 0.2). $^1H$ NMR (400 MHz, $CDCl_3$) δ 7.18 (m, 4H), 2.97 (m, 4H), 2.68 (d, J=12.5 Hz, 2H), 2.41 (m, 1H), 1.95 (d, J=11.0 Hz, 1H). APCI MS m/e 160.2 [(M+1)$^+$].

EXAMPLE 2

4-FLUORO-10-AZA-TRICYCLO[6.3.1.0$^{2,7}$]DODECA-2(7),3,5-TRIENE HYDROCHLORIDE

A) 6-Fluoro-1,4-dihydro-1,4-methano-naphthalene (Eisch, J. J.; Burlinson, N. E. J. Amer. Chem. Soc. 1976, 98, 753–761. Paquette, L. A.; Cottrell, D. M.; Snow, R. A. J. Amer. Chem. Soc. 1977, 99, 3723–3733.)

Magnesium turnings (0.66 g, 27.2 mmol) were stirred in anhydrous THF (10 mL) in a flame dried 75 mL 3 neck round bottom flask equipped with a non-equalizing addition funnel with a $N_2$ flow adapter, magnetic stirrer and efficient condenser equipped with a $N_2$ flow adapter. The flask was stirred and warmed to reflux by a removable heating mantle. 2,5-Difluorobromobenzene (0.1 g) was added followed by of 3N EtMgBr in THF (0.1 mL). The addition funnel was charged with an intimate mixture of cyclopentadiene (1.71 g, 25.9 mmol) and 2,5-difluorobromobenzene (5.0 g, 25.9 mmol). Small portions (~0.2 mL) of the intimate mixture were introduced to assist initiation (~4 times). After ~15 minutes, the reaction initiated (exotherm, and vapor condensation) and heating was maintained as necessary during the addition of the contents of the addition funnel. The reaction was then maintained at reflux for 1 hour.

The reaction was cooled to room temperature and quenched with H$_2$O (20 mL) followed by aqueous 1N HCl solution (20 mL) to dissolve the solids. Saturated aqueous NaCl solution (30 mL) was added and product was extracted with hexanes (4×25 mL). The combined organic layer was washed with saturated aqueous NaHCO$_3$ solution (25 mL), dried (Na$_2$SO$_4$), filtered through a Silica plug with hexanes rinse and concentrated to an oil. Chromatography on Silica gel eluting with hexanes provided an oil (780 mg, 19%). (TLC hexanes R$_f$ 0.38). $^1$H NMR (400 MHz, CDCl$_3$) δ 7.10 (m, 1H), 6.97 (d, J=8.0 Hz, 1H), 6.80 (br s, 1H), 6.78 (br s, 1H), 6.59 (m, 1H), 3.87 (br s, 2H), 2.32 (d, J=7.0 Hz, 1H), 2.25 (d, J=7.0 Hz, 1H).

B) 6-Fluoro-1,2,3,4-tetrahydro-1,4-methano-naphthalene-2,3-diol

6-Fluoro-1,4-dihydro-1,4-methano-naphthalene (680 mg, 4.22 mmol) and N-methyl morpholine N-oxide (599 mg, 4.43 mmol) were stirred in acetone (50 mL) and H$_2$O (5 mL). To this was added a solution of OsO$_4$ (0.2 mL, 2.5% wt. solution in t-butyl alcohol, 0.02 mmol). After 72 hours, Florisil (5 g) and saturated aqueous NaHSO$_3$ solution (3 mL) were added and stirred for 1 hour. The Florisil was filtered and the filtrate concentrated to produce a crystalline product which was triturated with acetone and filtered (524 mg, 64%). $^1$H NMR (400 MHz, CDCl$_3$) δ 7.10 (dd, J=8.0,5.0 Hz, 1H), 6.90 (dd, J=8.0,2.3 Hz, 1H), 6.75 (ddd, J=8.0,8.0,2.3 Hz, 1H), 3.79 (s, 2H), 3.18 (d, J=1.5 Hz, 2H), 2.22 (d, J=10.0 Hz, 1H), 1.92 (dd, J=10.0,1.5 Hz, 1H). GCMS m/e 194 (M$^+$).

C) 10-Benzyl-4-fluoro-10-aza-tricyclo[6.3.1.0$^{2,7}$]dodeca-2(7),3,5-triene 6-Fluoro-1,2,3,4-tetrahydro-1,4-methano-naphthalene-2,3-diol (524 mg, 2.68 mmol) and Et$_3$NBnCl (10 mg) were vigorously stirred in dichloroethane (15 mL) and H$_2$O (45 mL) then treated with sodium periodate (0.603 mg, 2.82 mmol). After 1.5 hours, the layers were separated and the aqueous layer extracted with DCE (2×20 mL). The combined organic layer was washed with H$_2$O (4×20 mL) until no reaction to starch iodide paper was observed, then with saturated aqueous NaCl solution (20 mL). The organic layer was dried through a cotton plug and treated with benzyl amine (0.308 mL, 2.82 mmol) and stirred for 2 minutes then transferred to an addition funnel. This solution was added over ~10 minutes to a vigorously stirred cooled (0° C.) mixture of NaHB(OAc)$_3$ (1.82 g, 8.58 mmol) in DCE (50 mL). After addition was complete, the mixture was stirred without cooling for 2 hours. The mixture was quenched with saturated aqueous Na$_2$CO$_3$ solution (100 mL) and stirred for 1 hour, then the layers were separated and the aqueous layer was extracted with CH$_2$Cl$_2$ (3×30 mL). The combined organic layer was washed with saturated aqueous NaCl solution (50 mL), dried through a cotton plug and concentrated. Chromatography on Silica gel provided an oil (520 mg, 80%). (TLC 2% acetone/CH$_2$Cl$_2$ R$_f$ 0.40). $^1$H NMR (400 MHz, CDCl$_3$) δ 7.18 (m, 1H), 3.48 (s, 2H), 3.06 (m, 2H), 2.78 (m, 2H), 2.41 (m, 2H), 2.27 (m, 1H), 1.69 (d, J=10.5 Hz, 1H).

D) 4-Fluoro-10-aza-tricyclo[6.3.1.0$^{2,7}$]dodeca-2(7),3,5-triene hydrochloride 10-Benzyl-4-fluoro-10-aza-tricyclo[6.3.1.0$^{2,7}$]dodeca-2(7),3,5-triene (390 mg, 1.461 mmol), ammonium formate (3.04 g, 48.2 mmol) and 10% Pd(OH)$_2$/C (30 mg) were combined in methanol (50 mL) and brought to reflux under N$_2$ for 1.5 hours. Ammonium formate (1.0 g) was added and reflux continued for 0.5 hour. The reaction mixture was filtered through a Celite pad which was rinsed with methanol. The filtrate was concentrated. The residues were treated with saturated aqueous Na$_2$CO$_3$ solution (30 mL) and product extracted with methylene chloride (CH$_2$Cl$_2$) (3×25 mL). The organic layer was washed with saturated aqueous NaCl solution (50 mL), dried through a cotton plug and concentrated. The residue was treated with 2N HCl methanol (5 mL) and concentrated then taken up in minimum of methanol and saturated with Et$_2$O. After stirring 18 h, the white crystals were collected by filtration (86 mg, 28%). (TLC 5% methanol/CH$_2$Cl$_2$ (NH$_3$) R$_f$ 0.27). (data for free base) $^1$H NMR (400 MHz, CDCl$_3$) δ 7.06 (m, 1H), 6.83 (m, 2H), 2.89 (m, 4H), 2.61 (dd, J=12.0 Hz, 2H), 2.37 (m, 1H), 1.87 (d, J=11.5 Hz, 1H). APCI MS m/e 178.2 [(M+1)$^+$]. (HCl salt) M.p. 260–262° C.

EXAMPLE 3

4-METHYL-10-AZA-TRICYCLO[6.3.1.0$^{2,7}$]DODECA-2(7),3,5-TRIENE HYDROCHLORIDE

The title compound was prepared by the methods described in Examples 1 and 2 starting with 2-fluoro-5-methylbromobenzene. (data for free base) $^1$H NMR (400 MHz, CDCl$_3$) δ 7.04 (d, J=7.5 Hz, 1H), 6.99 (s, 1H), 6.98 (d, J=7.5 Hz, 1H), 2.98–2.90 (m, 4H), 2.63 (m, 2H), 2.35 (m, 1H), 2.32 (s, 3H), 1.87 (d, J=11.5 Hz, 1H). APCI MS m/e 174.2 [(M+1)$^+$]. (HCl salt) M.p. 254–255° C. Anal. Calcd. for C$_{12}$H$_{12}$F$_3$N.HCl.1/3H$_2$O: C, 53.44; H, 5.11; N, 5.19. Found C, 53.73; H, 4.82; N, 5.15.

EXAMPLE 4

4-TRIFLUOROMETHYL-10-AZA-TRICYCLO[6.3.1.0$^{2,7}$]-DODECA-2(7),3,5-TRIENE HYDROCHLORIDE (See Grunewald, G. L.; Paradkar, V. M.; Pazhenchevsky, B.; Pleiss, M. A.; Sall, D. J.; Seibel, W. L.; Reitz, T. J. *J. Org. Chem.* 1983, 48, 2321–2327. Grunewald, G. L.; Markovich, K. M.; Sall, D. J. *J. Med. Chem.* 1987, 30, 2191–2208.)

The title compound was prepared by the methods described in Examples 1 and 2 starting with 2-fluoro-5-trifluoromethylbromobenzene. $^1$H NMR (400 MHz, CD$_3$OD) δ 7.71 (s, 1H), 7.64 (d, J=8.0 Hz, 1H), 7.57 (d, J=8.0 Hz, 1H), 3.46 (m, 4H), 3.21 (d, J=12.5 Hz, 2H), 2.41 (m, 1H), 2.16 (d, J=11.5 Hz, 1H). APCI MS m/e 228.2 [(M+1)$^+$]. (HCl salt) M.p. 244–246° C. Anal. Calcd. for C$_{12}$H$_{12}$F$_3$N.HCl.1/3H$_2$O: C, 53.44; H, 5.11; N, 5.19. Found C, 53.77; H, 4.82; N, 5.18.

EXAMPLE 5

3-TRIFLUOROMETHYL-10-AZA-TRICYCLO[6.3.1.0$^{2,7}$]-DODECA-2(7),3,5-TRIENE HYDROCHLORIDE (See Grunewald, G. L.; Paradkar, V. M.; Pazhenchevsky, B.; Pleiss, M. A.; Sall, D. J.; Seibel, W. L.; Reitz, T. J. *J. Org. Chem.* 1983, 48, 2321–2327. Grunewald, G. L.; Markovich, K. M.; Sall, D. J. *J. Med. Chem.* 1987, 30, 2191–2208.)

The title compound was prepared by the methods described in Examples 1 and 2 starting with 2-fluoro-6-trifluoromethylbromobenzene. $^1$H NMR (400 MHz, CD$_3$OD) δ 7.67–7.50 (3H), 3.65 (br s, 1H), 3.49–3.42 (m, 2H), 3.29 (s, 1H), 3.28–3.16 (m, 2H), 2.42 (m, 1H), 2.18 (d, J=11.5 Hz, 1H). APCI MS m/e 228.2 [(M+1)$^+$]. (HCl salt) M.p. 275–277° C. Anal. Calcd. for C$_{12}$H$_{12}$F$_3$N.HCl.1/3H$_2$O: C, 53.44; H, 5.11; N, 5.19. Found C, 53.73; H, 4.83; N, 5.16.

EXAMPLE 6

3-FLUORO-10-AZA-TRICYCLO[6.3.1.0$^{2,7}$]DODECA-2(7),3,5-TRIENE HYDROCHLORIDE

A) 2,6-Difluoroiodobenzene (Roe, A. M.; Burton, R. A.; Willey, G. L.; Baines, M. W.; Rasmussen, A. C. *J. Med. Chem.* 1968, 11, 814–819. Tamborski, C.; Soloski, E. *J. Org. Chem.* 1966, 31, 746–749. Grunewald, G. L.; Arrington, H. S.; Bartlett, W. J.; Reitz, T. J.; Sall, D. J. *J. Med. Chem.* 1986, 29, 1972–1982.) 1,3-Difluorobenzene (57.05 g, 0.5 M) in THF (75 mL) was added to a −78° C. stirred solution of n-butyllithium (n-BuLi) (200 mL, 2.5 M/hexanes, 0.5 M) and THF (500 mL) under N$_2$. By controlling the addition rate the internal temperature was maintained below −70° C. The total addition time was ~½ hour. The resulting slurry was stirred an additional ½ hour, then the dispersion was treated with a solution of iodine (126.9 g, 0.5 M) in THF (300 mL) at a rate that maintained an internal temperature below −70° C. After complete addition the mixture was allowed to warm to room temperature, and was treated with H$_2$O (100 mL) and 10% aqueous Na$_2$S$_2$O$_3$ solution (100 mL) and stirred. The layers were separated and the aqueous layer extracted with hexanes (2×250 mL). The combined organic layer was washed with 10% aqueous Na$_2$S$_2$O$_3$ solution (100 mL), H$_2$O (100 mL), saturated aqueous NaCl solution (100 mL), dried (Na$_2$SO$_4$) filtered and concentrated to give a yellow oil (106.5 g). Distillation at ~1–5 mm at ~80° C. provided a light yellow oil (89.5 g, 75%). $^1$H NMR (400 MHz, CDCl$_3$) δ 7.30 (m, 1H), 6.87 (m, 2H). GCMS m/e 240 (M$^+$).

B) 5-Fluoro-1,4-dihydro-1,4-methano-naphthalene

A solution of 2,6-difluoroiodobenzene (5.0 g, 20.8 mmol) and cyclopentadiene (2.07 g, 31.3 mmol) was stirred at 0° C. in P. ether (70 mL, 40–60° C.) under N$_2$ and treated with n-BuLi (8.74 mL, 2.5M in hexanes, 21.8 mmol) dropwise over 10 minutes. The reaction was quenched after 15 minutes by addition of aqueous 1N HCl solution and the product was extracted with hexanes (3×50 mL). The combined organic layer was washed with H$_2$O (50 mL), saturated aqueous NaCl solution (50 mL), dried (MgSO$_4$), filtered and evaporated. Chromatography on Silica gel provided product as an oil (1.5 g, 45%). (TLC hexanes R$_f$ 0.55). $^1$H NMR (400 MHz, CDCl$_3$) δ 7.08 (ddd, J=7.0,1.0,0.8 Hz, 1H), 6.96 (ddd, J=8.5,8.3,7.0 Hz, 1H), 6.86 (br s, 2H), 6.72 (ddd, J=8.5,8.3, 0.8 Hz, 1H), 4.25 (br s, 1H), 3.98 (br s, 1H), 2.36 (ddd, J=7.2,1.7,1.7 Hz, 1H), 2.30 (ddd, J=7.2,1.7,1.5 Hz, 1H). GCMS m/e 160 (M$^+$).

C) 3-Fluoro-10-aza-tricyclo[6.3.1.0$^{2,7}$]dodeca-2(7),3,5-triene hydrochloride The title compound was prepared by the methods described in Examples 2B, C, and D starting with 5-fluoro-1,4-dihydro-1,4-methano-naphthalene. $^1$H NMR (400 MHz, CD$_3$OD) δ 7.36 (ddd, J=8.3,7.3,5.0 Hz, 1H), 7.21 (d, J=7.3 Hz, 1H), 7.07 (t, J=8.3 Hz, 1H), 3.62 (br s, 1H), 3.42–3.30 (m, 3H), 3.21 (m, 2H), 2.38 (m, 1H), 2.12 (d, J=11.5 Hz, 1H). APCI MS m/e 178.4 [(M+1)$^+$]. M.p. 269–271° C.

EXAMPLE 7

4-NITRO-10-AZATRICYCLO[6.3.1.0$^{2,7}$]DODECA-2(7),3,5-TRIENE HYDROCHLORIDE

A) 1-(10-Aza-tricyclo[6.3.1.0$^{2,7}$]dodeca-2(7),3,5-trien-10-yl)-2,2,2-trifluoro-ethanone 10-Aza-tricyclo[6.3.1.0$^{2,7}$]dodeca-2(7),3,5-triene hydrochloride salt (12.4 g, 63.9 mmol) was stirred in CH$_2$Cl$_2$ (200 mL). This was cooled (ice bath) and treated with pyridine (12.65 g, 160 mmol) followed by trifluoroacetic anhydride (TFAA) (16.8 g, 11.3 mL, 80 mmol) from an addition funnel over 10 minutes. After ~3 hours, the solution was poured into 0.5N aqueous HCl (200 mL) and the layers separated. The aqueous layer was extracted with CH$_2$Cl$_2$ (3×50 mL) and the combined organic layer was washed with 0.5N aqueous HCl (50 mL), H$_2$O (2×50 mL) and saturated aqueous NaHCO$_3$ solution (50 mL). This solution was dried through a cotton plug, then diluted with ~3% ethyl acetate and filtered through a 2 inch Silica pad eluted with ~3% ethyl acetate/CH$_2$Cl$_2$. Concentration afforded a clear oil which crystallized to give white needles (15.35 g, 60.2 mmol, 94%). (TLC 30% ethyl acetate/hexanes R$_f$ 0.53). $^1$H NMR (400 MHz, CDCl$_3$) δ 7.18 (m, 4H), 4.29 (br d, J=12.6 Hz, 1H), 3.84 (br d, J=12.6 Hz, 1H), 3.51 (dd, J=12.6,1.5 Hz, 1H), 3.21 (br s, 1H), 3.10 (br s, 1H), 3.10 (br d, J=12.6 Hz, 1H), 2.37 (m, 1H), 1.92 (d, J=10.8 Hz, 1H). GCMS m/e 255 (M$^+$). M.p. 67–68° C.

B) 1-(4-Nitro-10-aza-tricyclo[6.3.1.0$^{2,7}$]dodeca-2(7),3,5-trien-10-yl)-2,2,2-trifluoro-ethanone (Based on the method described by Coon, C. L.; Blucher, W. G.; Hill, M. E. *J. Org. Chem.* 1973, 25, 4243.) To a solution of trifluoromethanesulfonic acid (2.4 ml, 13.7 mmol) in CH$_2$Cl$_2$ (10 ml) stirred at 0° C. was slowly added nitric acid (0.58 ml, 27.4 mmol) generating a white precipitate. After 10 minutes the resulting mixture was cooled to −78° C. and treated with 1-(10-aza-tricyclo[6.3.1.0$^{2,7}$]dodeca-2(7),3,5-trien-10-yl)-2,2,2-trifluoro-ethanone (3.5 g, 13.7 mmol) in CH$_2$Cl$_2$ (15 ml) dropwise from an addition funnel over 5 minutes. The reaction was stirred at −78° C. for 30 minutes then warmed to 0° C. for 1 hour. The reaction mixture was poured into a vigorously stirred ice (100 g). The layers were separated and the aqueous layer extracted with CH$_2$Cl$_2$ (3×30 ml). The organic layer was combined and washed with H$_2$O (3×30 ml). The combined organic layer was washed with saturated aqueous NaHCO$_3$ solution (20 mL) and H$_2$O (20 mL) then dried through a cotton plug and concentrated to give an orange oil that solidified on standing (4.2 g). Chromatography yielded pure product as a crystalline solid (3.2 g, 78%). (TLC 30% ethyl acetate/hexanes R$_f$ 0.23). $^1$H NMR (400 MHz, CDCl$_3$) δ 8.12 (br d, J=8.0 Hz, 1H), 8.08 (br s, 1H), 7.37 (br d, J=8.0 Hz, 1H), 4.38 (br d, J=12.6 Hz, 1H), 3.94 (br d, J=12.6 Hz, 1H), 3.59 (br d, J=12.6 Hz, 1H), 3.43–3.35 (m, 2H), 3.18 (br d, J=12.6 Hz, 1H), 2.48 (m, 1H), 2.07 (d, J=10.8 Hz, 1H). GCMS m/e 300 (M$^+$).

C) 4-Nitro-10-azatricyclo[6.3.1.0$^{2,7}$]dodeca-2(7),3, 5-triene hydrochloride 1-(4-Nitro-10-aza-tricyclo[6.3.1.0$^{2,7}$]dodeca-2(7),3,5-trien-10-yl)-2,2,2-trifluoro-ethanone (182 mg, 0.61 mmol) was stirred with Na$_2$CO$_3$ (160 mg, 1.21 mmol) in methanol (3 mL) and H$_2$O (1 mL) at 70° C. for 18 hours. The mixture was concentrated, water was added and the product was extracted with CH$_2$Cl$_2$. The organic layer was extracted with 1N aqueous HCl (3×20 mL) and the acidic layer washed with CH$_2$Cl$_2$ (2×20 mL). The aqueous layer was basified to pH~10 with Na$_2$CO$_3$(s) and product was extracted with CH$_2$Cl$_2$ (3×30 mL). The organic layer was dried through a cotton plug and concentrated to an oil. This was dissolved in methanol and treated with 1N HCl in methanol, concentrated to solids which were recrystallized from methanol/Et$_2$O to afford product as a white solid (73 mg, 50%). (TLC 5% methanol/CH$_2$Cl$_2$ (NH$_3$) R$_f$ 0.38). $^1$H NMR (400 MHz, DMSO-d$_6$) δ 8.21 (s, 1H), 8.18 (dd, J=8.0,2.0 Hz, 1H), 7.59 (d, J=8.0 Hz, 1H), 3.43 (br s, 2H), 3.28 (m, 2H), 3.07 (dd, J=13.0,13.0 Hz, 2H), 2.24 (m, 1H), 2.08 (d, J=11.5 Hz, 1H). APCI MS m/e 205.1 [(M+1)$^+$] M.p. 265–270° C.

EXAMPLE 8

4-AMINO-10-AZATRICYCLO[6.3.1.0$^{2,7}$]DODECA-2(7),3,5-TRIENE HYDROCHLORIDE

4-Nitro-10-azatricyclo[6.3.1.0$^{2,7}$]dodeca-2(7),3,5-triene (500 mg, 2.08 mmol) was stirred in 1,4-dioxane (40 mL) and treated with saturated aqueous Na$_2$CO$_3$ solution (15 mL). To this was added di-t-butyldicarbonate (1.8 g, 8.31 mmol). After stirring 18 hours the reaction was treated with H$_2$O (50 mL), extracted with CH$_2$Cl$_2$ (4×30 mL), dried through a cotton plug and concentrated to provide an oil (500 mg, 91%).

This oil (500 mg, 1.64 mmol) was dissolved in methanol (30 mL), treated with 10% Pd/C (~50 mg) and hydrogenated under a H$_2$ atmosphere (45 psi) for 1 hour. The mixture was filtered through a Celite pad and concentrated to a clear oil (397 mg, 88%).

This oil (50 mg, 0.18 mmol) was stirred in 3N HCl in ethyl acetate (3 mL) for 2 hours then concentrated to a white solid (25 mg, 56%). $^1$H NMR (400 MHz, DMSO-d$_6$) δ 7.38–7.10 (3H), 3.60 (br s, 2H), 3.25 (m, 2H), 2.98 (m, 2H), 2.18 (m, 1H), 1.98 (d, J=11.5 Hz, 1H). APCI MS m/e 175.1 [(M+1)$^+$] M.p. 189–192° C.

EXAMPLE 9

N$^1$-[10-AZATRICYCLO[6.3.1.0$^{2,7}$]DODECA-2(7), 3,5-TRIEN-4-YL]-ACETAMIDE HYDROCHLORIDE

A) 1-(4-Amino-10-aza-tricyclo[6.3.1.0$^{2,7}$]dodeca-2 (7),3,5-trien-10-yl)-2,2,2-trifluoro-ethanone Hydrogenation of 1-(4-nitro-10-aza-tricyclo[6.3.1.0$^{2,7}$]dodeca-2(7),3,5-trien-10-yl)-2,2,2-trifluoro-ethanone (2.0 g, 6.66 mmol) under a H$_2$ atmosphere (40 psi) and 10% Pd/C (200 mg) in methanol over 1.5 hours, filtration through Celite and concentration affords a yellow oil (1.7 g). (TLC 50% ethyl acetate/hexanes R$_f$ 0.27). $^1$H NMR (400 MHz, CDCl$_3$) δ 6.99 (m, 1H), 6.64 (br s, 1H), 6.57 (m, 1H), 4.25 (m, 1H), 3.82 (m, 1H), 3.50 (m, 1H), 3.17–3.07 (m, 3H), 2.35 (m, 1H), 1.90 (d, J=10.8 Hz, 1H). GCMS m/e 270 (M$^+$).

B) N-(10-Trifluoroacetyl-10-aza-tricyclo[6.3.1.0$^{2,7}$] dodeca-2(7),3,5-trien-4-yl)-acetamide 1-(4-Amino-10-aza-tricyclo[6.3.1.0$^{2,7}$]dodeca-2(7),3,5-trien-10-yl)-2,2,2-trifluoro-ethanone (850 mg, 3.14 mmol) was stirred in CH$_2$Cl$_2$ (5 mL) and treated with triethyl amine (0.53 mL, 3.76 mmol) and acetyl chloride (0.23 mL, 3.2 mmol) then stirred 18 hours. Standard NaHCO$_3$ work-up yielded an oil which was chromatographed to provide a clear oil (850 mg, 87%). (50% ethyl acetate/hexanes R$_f$ 0.28).

C) N$^1$-[10-Azatricyclo[6.3.1.0$^{2,7}$]dodeca-2(7),3,5-trien-4-yl]acetamide hydrochloride N-(10-Trifluoroacetyl-10-aza-tricyclo[6.3.1.0$^{2,7}$]dodeca-2(7),3,5-trien-4-yl)-acetamide (100 mg, 0.32 mmol) was stirred with Na$_2$CO$_3$ (70 mg, 0.64 mmol) in methanol (10 mL) and H$_2$O (2 mL) at 70° C. for 18 hours. The mixture was concentrated, water was added and the product was extracted with ethyl acetate. The organic layer was extracted with 1N aqueous HCl (3×20 mL) and the acidic layer washed with ethyl acetate (2×20 mL). The aqueous layer was basified to pH~10 with Na$_2$CO$_3$ (s) and product was extracted with ethyl acetate (3×20 mL). The organic layer was dried (sodium sulfate (Na$_2$SO$_4$)) and concentrated to an oil. This material was dissolved in methanol and treated with 3N HCl ethyl acetate (3 mL), concentrated and recrystallized from methanol/Et$_2$O to provide a solid (40 mg, 50%). $^1$H NMR (400 MHz, DMSO-d$_6$) δ 9.98 (s, 1H), 9.02 (br m, NH), 7.65 (s, 1H), 7.55 (br s, NH), 7.38 (d, J=8.0 Hz, 1H), 7.20 (d, J=8.0 Hz, 1H), 3.33 (m, 4H), 2.96 (m, 2H), 2.13 (m, 1H), 2.00 (s, 3H), 1.96 (d, J=10.5 Hz, 1H). APCI MS m/e 217.2 [(M+1)$^+$]. M.p. 225–230° C.

EXAMPLE 10

6-METHYL-5-THIA-7,13-DIAZATETRACYCLO [9.3.1.0$^{2,10}$.0$^{4,8}$]PENTADECA-2(10),3,6,8-TETRAENE HYDROCHLORIDE

A) N-(10-Trifluorothioacetyl-10-aza-tricyclo [6.3.1.0$^{2,7}$]dodeca-2(7),3,5-trien-4-yl)-thioacetamide N-(10-Trifluoroacetyl-10-aza-tricyclo[6.3.1.0$^{2,7}$]dodeca-2(7),3,5-trien-4-yl)-acetamide (850 mg, 2.72 mmol) and 2,4-bis(4-methoxyphenyl)-1,3-dithia-2,4-diphosphetane-2, 4-disulfide (Lawesson's reagent) (1.1 g, 2.72 mmol) were combined in toluene (10 mL) and brought to reflux for 1.5 hours. After cooling the reaction was worked up with ethyl acetate/saturated aqueous $NaHCO_3$ solution. The organic layer was dried ($Na_2SO_4$), filtered, concentrated and chromatographed on Silica gel to produce product (410 mg, 44%). (50% ethyl acetate/hexanes $R_f$ 0.38)

B) 6-Methyl-5-thia-7,13-diazatetracyclo[9.3.1.0$^{2,}$ $_{10}$.0$^{4,8}$]pentadeca-2(10),3,6,8-tetraene hydrochloride The above oil, 2,2,2-trifluoro-N-(10-trifluorothioacetyl-10-aza-tricyclo[6.3.1.0$^{2,7}$]dodeca-2(7),3,5-trien-4-yl)-thioacetamide, (360 mg, 1.05 mmol) was dissolved in methanol (10 mL) and 1N NaOH (5 mL) and added to potassium ferricyanide ($K_3Fe(CN)_6$)(1.72 g, 5.23 mmol) in $H_2O$ (10 mL). This mixture was warmed to 60° C. for 1.5 hours, cooled, concentrated and worked up with ethyl acetate/$H_2O$. This material was stirred in dioxane (20 mL) and treated with $H_2O$ (50 mL) and $Na_2CO_3$ to achieve pH 10. To this was added di-t-butyldicarbonate (436 mg, 2.0 mmol) and the mixture was stirred for 18 hours. The reaction was concentrated, treated with $H_2O$ and extracted with $CH_2Cl_2$. The product was chromatographed (Silica 30% ethyl acetate/hexanes $R_f$ 0.41) to yield an oil (100 mg).

The above product was treated with 3N HCl/ethyl acetate (3 mL) and warmed to reflux for ~15 minutes then concentrated to a solid which was azeotroped with $CH_2Cl_2$ (two times). These solids were dissolved in a minimum amount of methanol then saturated with $Et_2O$ and stirred. The resulting white crystalline powder was collected by filtration (40 mg, 14%).

$^1$H NMR (400 MHz, DMSO-$d_6$) δ 9.46 (s, NH), 7.65 (s, 1H), 7.82 (s, 1H), 7.65 (br m, NH), 3.36 (m, 2H), 3.24 (m, 2H), 3.02 (m, 2H), 2.76 (s, 3H), 2.23 (m, 1H), 2.06 (d, J=10.8 Hz, 1H). APCI MS m/e 231.1 [(M+1)$^+$]. M.p. 183–184° C.

EXAMPLE 11

4,5-DINITRO-10-AZA-TRICYCLO[6.3.1.0$^{2,7}$]DODECA-2(7),3,5-TRIENE

A) 1-(4,5-Dinitro-10-aza-tricyclo[6.3.1.0$^{2,7}$]dodeca-2(7),3,5-trien-10-yl)-2,2,2-trifluoro-ethanone (Based on the method described in Coon, C. L.; Blucher, W. G.; Hill, M. E. *J. Org. Chem.* 1973, 25, 4243. For an additional related example of dinitration see: Tanida, H.; Ishitobi, H.; Irie, T.; Tsushima, T. *J. Am. Chem. Soc.* 1969, 91, 4512.)

To a solution of trifluoromethanesulfonic acid (79.8 ml, 902.1 mmol) in $CH_2Cl_2$ (550 ml) stirred at 0° C. was slowly added nitric acid (19.1 ml, 450.9 mmol) generating a white precipitate. After 10 minutes, 1-(10-aza-tricyclo[6.3.1.0$^{2,7}$]dodeca-2(7),3,5-trien-10-yl)-2,2,2-trifluoro-ethanone (50 g, 196 mmol) in $CH_2Cl_2$ (300 ml) was added dropwise from an addition funnel over 30 minutes. The reaction was stirred at 0° C. for 2.5 hours and then stirred at room temperature for 24 hours. The reaction mixture was poured into a vigorously stirred mixture of $H_2O$ (500 ml) and ice (400 g). The layers were separated and the aqueous layer back extracted with $CH_2Cl_2$ (3×300 ml). The organic layer was combined and washed with $H_2O$ (3×300 ml). The combined aqueous layers were re-extracted with $CH_2Cl_2$ (2×100 ml). The organic layer was combined and washed with saturated aqueous $NaHCO_3$ solution (200 mL) and $H_2O$ (200 mL) then dried through a cotton plug and concentrated to solids. Trituration with ethyl acetate/hexanes produced off white solids which were filtered and dried (52 g, 151 mmol, 77%. The mother liquor was chromatographed to give an additional 4.0 g for a total of 56.0 g (82.8%). (TLC 50% ethyl acetate/hexanes $R_f$ 0.29) $^1$H NMR (400 MHz, CDCl$_3$) δ 7.77 (s, 1H), 7.75 (s, 1H), 4.39 (br d, J=13.0 Hz, 1H), 3.98 (br d, J=13.0 Hz, 1H), 3.65 (d, J=13.0 Hz, 1H), 3.49 (br s, 1H), 3.44 (br s, 1H), 3.24 (br d, J=12.6 Hz, 1H), 2.53 (m, 1H), 2.14 (d, J=11.5 Hz, 1H). GCMS m/e 345 (M$^+$).

B) 4,5-Dinitro-10-aza-tricyclo[6.3.1.0$^{2,7}$]dodeca-2(7),3,5-triene 1-(4,5-Dinitro-10-aza-tricyclo[6.3.1.0$^{2,7}$]dodeca-2(7),3,5-trien-10-yl)-2,2,2-trifluoro-ethanone (3.7 g, 10.7 mmol) and $Na_2CO_3$ (2.3 g, 21.4 mmol) were combined in methanol (50 mL) and $H_2O$ (20 mL) then warmed to reflux for 18 hours. The reaction was cooled, concentrated, treated with $H_2O$ and extracted with $CH_2Cl_2$ (3×50 mL) then dried through a cotton plug. After concentration, the residue was chromatographed to provide brown solids. (1.9 g, 71%). (TLC 5% methanol/$CH_2Cl_2$ (NH$_3$) $R_f$ 0.36). $^1$H NMR (400 MHz, CDCl$_3$) δ 7.69 (s, 2H), 3.17 (br s, 2H), 3.11 (d, J=12.6 Hz, 2H), 2.53 (m, 1H), 2.07 (d, J=11.0 Hz, 1H). GCMS m/e 249 (M$^+$).

EXAMPLE 12

6-METHYL-7-PROPYL-5,7,13-TRIAZATETRACYCLO[9.3.1.0$^{2,10}$.0$^{4,8}$]-PENTADECA-2(10),3,5,8-TETRAENE HYDROCHLORIDE

A) 4,5-Dinitro-10-aza-tricyclo[6.3.1.0$^{2,7}$]dodeca-2(7),3,5-triene-10-carboxylic acid tert-butyl ester 4,5-Dinitro-10-aza-tricyclo[6.3.1.0$^{2,7}$]dodeca-2(7),3,5-triene, (1.9 g, 7.6 mmol) was stirred in 1,4-dioxane (75 mL) and treated with saturated aqueous $Na_2CO_3$ solution (10 mL). To this was added di-t-butyldicarbonate (3.31 g, 15.2 mmol). After stirring 6 hours the reaction was treated with $H_2O$ (50 mL) and extracted with ethyl acetate (4×25 mL), dried ($Na_2SO_4$), filtered, concentrated and chromatographed to provide product (1.9 g, 71%). (TLC 30% ethyl acetate/hexanes (NH$_3$) $R_f$ 0.58). $^1$H NMR (400 MHz, CDCl$_3$) δ 7.77 (br s, 1H), 7.72 (br s, 1H), 4.08 (m, 1H), 3.92 (m, 1H), 3.39 (br s, 1H), 3.27 (br s, 1H), 3.25 (m, 1H), 3.18 (m, 1H), 2.46 (m, 1H), 2.02 (d, J=11.0 Hz, 1H).

B) 4,5-Diamino-10-aza-tricyclo[6.3.1.0$^{2,7}$]dodeca-2(7),3,5-triene-10-carboxylic acid tert-butyl ester 4,5-Dinitro-10-aza-tricyclo[6.3.1.0$^{2,7}$]dodeca-2(7),3,5-triene-10-carboxylic acid tert-butyl ester (1.9 g, 5.44 mmol) was hydrogenated in methanol under a $H_2$ atmosphere (45 psi) over 10% Pd/C (100 mg) for 1.5 hours then filtered through a Celite pad and concentrated to white solids (1.57 g, 100%). (TLC 5% methanol/$CH_2Cl_2$ (NH$_3$) $R_f$ 0.14).

C) 6-Methyl-5,7,13-triazatetracyclo[9.3.1.0$^{2,10}$.0$^{4,8}$]pentadeca-2(10),3,5,8-tetraene-13-carboxylic acid tert-butyl ester (For conditions, see; Segelstein, B. E.; Chenard, B. L.; Macor, J. E.; Post, R. J. *Tetrahedron Lett.* 1993, 34, 1897.)
4,5-Diamino-10-aza-tricyclo[6.3.1.0$^{2,7}$]dodeca-2(7),3,5-triene-10-carboxylic acid tert-butyl ester (700 mg, 2.42 mmol) was dissolved in ethanol (10 mL) and acetic acid (HOAc) (1 mL) and treated with 1-ethoxyethylenemalononitrile (329 mg, 2.42 mmol). The resulting mixture was warmed to 60° C. and stirred 18 hours. The reaction was cooled, concentrated treated with H$_2$O and saturated aqueous Na$_2$CO$_3$ solution and extracted with ethyl acetate (3×50 mL), then dried (Na$_2$SO$_4$). After filtration and concentration, the residue was chromatographed to provide brown solids (247 mg, 36%). (TLC 5% methanol/CH$_2$Cl$_2$ (NH$_3$) R$_f$ 0.28).

D) 6-Methyl-7-propyl-5,7,13-triazatetracyclo [9.3.1.0$^{2,10}$.0$^{4,8}$]pentadeca-2(10),3,5,8-tetraene-13-carboxylic acid tert-butyl ester (For conditions, see; Pilarski, B. *Liebigs Ann. Chem.* 1983, 1078.) 6-Methyl-5,7,13-triazatetracyclo[9.3.1. 0$^{2,10}$.0$^{4,8}$]pentadeca-2(10),3,5,8-tetraene-13-carboxylic acid tert-butyl ester (80 mg, 0.267 mmol) was stirred in 50% aqueous NaOH solution (3 mL) and DMSO (1 mL) then treated with 1-iodopropane (0.03 mL, 0.321 mmol). This mixture was warmed to 40° C. for 2 hours then cooled, treated with H$_2$O and extracted with ethyl acetate. The organic layer was washed with H$_2$O (3 times) then dried (Na$_2$SO$_4$), filtered and concentrated to an oil (90 mg, 0.253 mmol). (TLC 5% methanol/CH$_2$Cl$_2$ (NH$_3$) R$_f$ 0.15).

E) 6-Methyl-7-propyl-5,7,13-triazatetracyclo [9.3.1.0$^{2,10}$.0$^{4,8}$]pentadeca-2(10),3,5,8-tetraene hydrochloride 6-Methyl-7-propyl-5,7,13-triazatetracyclo[9.3.1.0$^{2,10}$. 0$^{4,8}$]pentadeca-2(10),3,5,8-tetraene-13-carboxylic acid tert-butyl ester (90 mg, 0.253 mmol) was dissolved in 3N HCl ethyl acetate (5 mL) and warmed to 100° C. for ½ hour. The mixture was cooled, concentrated, slurried in ethyl acetate, and filtered to provide a white solid (25 mg, 34%). $^1$H NMR (400 MHz, DMSO-d$_6$) δ 9.56 (s, NH), 7.91 (s, 1H), 7.83 (br m, NH), 7.74 (s, 1H), 4.38 (m, 2H), 3.48 (m, 2H), 3.32 (m, 2H), 3.10 (m, 2H), 2.87 (s, 3H), 2.28 (m, 1H), 2.15 (d, J=11.0 Hz, 1H) 1.85 (m, 2H), 0.97 (m, 3H). M.p. 147–150° C.

EXAMPLE 13

5,7,13-TRIAZATETRACYCLO[9.3.1.0$^{2,10}$.0$^{4,8}$]-PENTADECA-2(10),3,5,8-TETRAENE HYDROCHLORIDE

A) 5,7,13-Triazatetracyclo[9.3.1.0$^{2,10}$.0$^{4,8}$]pentadeca-2(10),3,5,8-tetraene-13-carboxylic acid tert-butyl ester (For conditions, see; Segelstein, B. E.; Chenard, B. L.; Macor, J. E.; Post, R. J. *Tetrahedron Lett.* 1993, 34, 1897.)

4,5-Diamino-10-aza-tricyclo[6.3.1.0$^{2,7}$]dodeca-2(7),3,5-triene-10-carboxylic acid tert-butyl ester (1.0 g, 3.45 mmol) was dissolved in ethanol (10 mL) and HOAc (1 mL) and treated with ethoxymethylenemalononitrile (421 mg, 3.45 mmol). The resulting mixture was warmed to 60° C. and stirred 18 hours. The reaction was cooled, concentrated treated with H$_2$O and saturated aqueous Na$_2$CO$_3$ solution and extracted with ethyl acetate (3×50 mL), then dried (Na$_2$SO$_4$). After filtration and concentration, the residue was chromatographed to provide brown solids (580 mg, 56%). (TLC 5% methanol/CH$_2$Cl$_2$ (NH$_3$) R$_f$ 0.28)

B) 5,7,13-triazatetracyclo[9.3.1.0$^{2,10}$.0$^{4,8}$]pentadeca-2(10),3,5,8-tetraene hydrochloride 5,7,13-Triazatetracyclo[9.3.1.0$^{2,10}$.0$^{4,8}$]pentadeca-2(10), 3,5,8-tetraene-13-carboxylic acid tert-butyl ester was converted to the title compound by the methods described in Example 12E. $^1$H NMR (400 MHz, D$_2$O) δ 8.95 (s, 1H), 7.67 (s, 2H), 3.45 (br s, 2H), 3.31 (d, J=12.5 Hz, 2H), 3.13 (d, J=12.5 Hz, 2H), 2.30 (m, 1H), 1.99 (d, J=11.5 Hz, 1H). APCI MS m/e 200.1 [(M+1)$^+$]. M.p.>250° C.

EXAMPLE 14

7-METHYL-5,7,13-TRIAZATETRACYCLO [9.3.1.0$^{2,10}$.0$^{4,8}$]-PENTADECA-2(10),3,5,8-TETRAENE HYDROCHLORIDE

Utilizing the methods described in Example 12D, 5,7,13-triazatetracyclo[9.3.1.0$^{2,10}$.0$^{4,8}$]pentadeca-2(10),3,5,8-tetraene-13-carboxylic acid tert-butyl ester was converted to the title compound by reaction with iodomethane followed by deprotection as described in Example 12E. $^1$H NMR (400 MHz, D$_2$O) δ 8.97 (s, 1H), 7.71 (s, 1H), 7.67 (s, 1H), 3.94 (s, 3H), 3.48 (m, 2H), 3.33 (d, J=12.2 Hz, 2H), 3.14 (d, J=12.2 Hz, 2H), 2.34 (m, 1H), 2.03 (d, J=11.5 Hz, 1H). APCI MS m/e 214.2 [(M+1)$^+$].

EXAMPLE 15

6-METHYL-5,7,13-TRIAZATETRACYCLO [9.3.1.0$^{2,10}$.0$^{4,8}$]-PENTADECA-2(10),3,5,8-TETRAENE HYDROCHLORIDE

6-Methyl-5,7,13-triazatetracyclo[9.3.1.0$^{2,10}$.0$^{4,8}$]pentadeca-2(10),3,5,8-tetraene-13-carboxylic acid tert-butyl ester was converted to the title compound by the methods described in Example 12E. $^1$H NMR (400 MHz, DMSO-d$_6$) δ 9.40 (br m, NH), 7.77 (br m, NH), 7.70 (s, 1H), 3.44 (m, 2H), 3.30 (m, 2H), 3.05 (br d, J=11.0 Hz, 2H), 2.79 (s, 3H), 2.23 (m, 1H), 2.10 (d, J=10.8 Hz, 1H). GCMS m/e 213.5 (M$^+$).

EXAMPLE 16

6,7-DIMETHYL-5,7,13-TRIAZATETRACYCLO [9.3.1.0$^{2,10}$.0$^{4,8}$]-PENTADECA-2(10),3,5,8-TETRAENE HYDROCHLORIDE

Utilizing the methods described in Example 12D, 6-methyl-5,7,13-triazatetracyclo[9.3.1.0$^{2,10}$.0$^{4,8}$]pentadeca-2 (10),3,5,8-tetraene-13-carboxylic acid tert-butyl ester was converted to the title compound by reaction with iodomethane followed by deprotection as described in Example 12E. $^1$H NMR (400 MHz, DMSO-d$_6$) δ 9.52 (s, NH), 7.84 (s, 1H), 7.82 (br m, NH), 7.72 (s, 1H), 3.90 (s, 3H), 3.45 (m, 2H), 3.28 (m, 2H), 3.04 (m, 2H), 2.82 (s, 3H), 2.23 (m, 1H), 2.12 (d, J=11.0 Hz, 1H). APCI MS m/e 228.2 [(M+1)$^+$]. M.p. 225–230° C.

EXAMPLE 17

7-PROPYL-5,7,13-TRIAZATETRACYCLO [9.3.1.0$^{2,10}$.0$^{4,8}$]-PENTADECA-2(10),3,5,8-TETRAENE HYDROCHLORIDE

Utilizing the methods described in Example 12D, 5,7,13-triazatetracyclo[9.3.1.0$^{2,10}$.0$^{4,8}$]pentadeca-2(10),3,5,8-tetraene-13-carboxylic acid tert-butyl ester was converted to the title compound by reaction with iodopropane followed by deprotection as described in Example 12E. $^1$H NMR (400 MHz, DMSO-d$_6$) δ 9.52 (s, 1H), 9.45 (br s, NH), 7.97 (s, 1H), 7.85 (s, 1H), 7.83 (br m, NH), 4.43 (m, 2H), 3.49 (m, 2H), 3.33 (m, 2H), 3.08 (m, 2H), 2.28 (m, 1H), 2.15 (d, J=11.0 Hz, 1H), 1.92 (m, 2H), 0.93 (m, 3H). APCI MS m/e 242.2 [(M+1)$^+$]. M.p. 170–171° C. (subl.).

EXAMPLE 18

7-BUTYL-5,7,13-TRIAZATETRACYCLO[9.3.1.0$^{2,10}$.0$^{4,8}$]-PENTADECA-2(10),3,5,8-TETRAENE HYDROCHLORIDE

A) 4-Butylamino-5-nitro-10-aza-tricyclo[6.3.1.0$^{2,7}$]dodeca-2(7),3,5-triene-10-carboxylic acid tert-butyl ester (For conditions, see; Senskey, M. D.; Bradshaw, J. D.; Tessier, C. A.; Youngs, W. J. *Tetrahedron Lett.* 1995, 36, 6217.)

4,5-Dinitro-10-aza-tricyclo[6.3.1.0$^{2,7}$]dodeca-2(7),3,5-triene-10-carboxylic acid tert-butyl ester (500 mg, 1.43 mmol) and 1-butylamine (1.42 mL, 14.3 mmol) were combined in THF (5 mL) and stirred 4 hours. The mixture was diluted with ethyl acetate (50 mL) and washed with H$_2$O (3×30 mL) then dried (Na$_2$SO$_4$), filtered and concentrated to an oil. This oil was passed through a Silica gel filter column to remove baseline impurities eluting with 30% ethyl acetate/hexanes (510 mg, 1.41 mmol, 99%).

B) 4-Butylamino-5-amino-10-aza-tricyclo[6.3.1.0$^{2,7}$]dodeca-2(7),3,5-triene-10-carboxylic acid tert-butyl ester 4-Butylamino-5-nitro-10-aza-tricyclo[6.3.1.0$^{2,7}$]dodeca-2(7),3,5-triene-10-carboxylic acid tert-butyl ester (460 mg, 1.27 mmol) was treated with ammonium formate (850 mg, 12.7 mmol) and 10% Pd(OH)$_2$/C (50 mg) in methanol (20 mL) and brought to reflux for 1 hour then filtered through a Celite pad and concentrated. The solids were treated with saturated aqueous Na$_2$CO$_3$ solution, extracted with CH$_2$Cl$_2$ (3×30 mL) and dried by filtration through a cotton plug to give an oil (440 mg, 100%).

C) 7-Butyl-5,7,13-triazatetracyclo[9.3.1.0$^{2,10}$.0$^{4,8}$]pentadeca-2(10),3,5,8-tetraene-13-carboxylic acid tert-butyl ester 4-Butylamino-5-amino-10-aza-tricyclo[6.3.1.0$^{2,7}$]dodeca-2(7),3,5-triene-10-carboxylic acid tert-butyl ester (440 mg, 1.27 mmol) was dissolved in ethanol (20 mL) and HOAc (2 mL) and treated with ethoxymethylenemalononitrile (186 mg, 1.52 mmol). The resulting mixture was warmed to 60° C. and stirred 18 hours. The reaction was cooled, concentrated, treated with H$_2$O and saturated aqueous Na$_2$CO$_3$ solution then extracted with ethyl acetate (3×50 mL) and dried (Na$_2$SO$_4$). After filtration and concentration, the residue was chromatographed to provide a yellow oil. (400 mg, 89%). (TLC 5% methanol/CH$_2$Cl$_2$ (NH$_3$) R$_f$ 0.70).

D) 7-Butyl-5,7,13-triazatetracyclo[9.3.1.0$^{2,10}$.0$^{4,8}$]pentadeca-2(10),3,5,8-tetraene hydrochloride 7-Butyl-5,7,13-triazatetracyclo[9.3.1.0$^{2,10}$.0$^{4,8}$]pentadeca-2(10),3,5,8-tetraene-13-carboxylic acid tert-butyl ester was converted to the title compound by the methods described in Example 12E. $^1$H NMR (400 MHz, DMSO-d$_6$) δ 9.93 (brs, NH), 9.68 (s, 1H), 7.99 (s, 1H), 7.92 (br m, NH), 7.87 (s, 1H), 4.50 (m, 2H), 3.49 (m, 2H), 3.30 (m, 2H), 3.08 (m, 2H), 2.26 (m, 1H), 2.15 (d, J=11.0 Hz, 1H), 1.88 (m, 2H), 1.32 (m, 2H), 0.82 (t, J=7.0 Hz, 3H). APCI MS m/e 256.2 [(M+1)$^+$]. M.p. 204–208° C.

EXAMPLE 19

7-ISOBUTYL-5,7,13-TRIAZATETRACYCLO[9.3.1.0$^{2,10}$.0$^{4,8}$]-PENTADECA-2(10),3,5,8-TETRAENE HYDROCHLORIDE 4,5-Dinitro-10-aza-tricyclo[6.3.1.0$^{2,7}$]dodeca-2(7),3,5-triene-10-carboxylic acid tert-butyl ester and isobutylamine were converted to the title compound utilizing the methods described in Example 18A–D. $^1$H NMR (400 MHz, CDCl$_3$) δ 7.74 (s, 1H), 7.52 (s, 1H), 7.14 (s, 1H), 3.90 (dd, J=7.5,2.0 Hz, 2H), 3.04–2.97 (m, 4H), 2.70 (dd, J=12.8,2.3 Hz, 2H), 2.42 (m, 1H), 2.19 (m, 1H), 1.98 (d, J=10.5 Hz, 1H), 0.93 (m, 6H). APCI MS m/e 256.2 [(M+1)$^+$]. M.p. 147–150° C. (subl.).

EXAMPLE 20

6-METHYL-7-ISOBUTYL-5,7,13-TRIAZATETRACYCLO[9.3.1.0$^{2,10}$.0$^{4,8}$]-PENTADECA-2(10),3,5,8-TETRAENE HYDROCHLORIDE

A) 6-Methyl-7-isobutyl-5,7,13-triazatetracyclo[9.3.1.0$^{2,10}$.0$^{4,8}$]-pentadeca 2(10),3,5,8-tetraene-13-carboxylic acid tert-butyl ester 4-Amino-5-isobutylamino-10-aza-tricyclo[6.3.1.0$^{2,7}$]dodeca-2(7),3,5-triene-10-carboxylic acid tert-butyl ester (250 mg, 0.74 mmol) from Example 19B was dissolved in ethanol (10 mL) and HOAc (2 mL) and treated with 1-ethoxyethylenemalononitrile (118 mg, 0.87 mmol). The reaction proceeded as in Example 18C (18 h) and was worked up similarly to provide product (TLC 3% methanol/CH$_2$Cl$_2$ (NH$_3$) R$_f$ 0.57).

B) 6-Methyl-7-isobutyl-5,7,13-triazatetracyclo[9.3.1.0$^{2,10}$.0$^{4,8}$]pentadeca-2(10),3,5,8-tetraene hydrochloride 6-Methyl-7-isobutyl-5,7,13-triazatetracyclo[9.3.1.0$^{2,10}$.0$^{4,8}$]pentadeca-2(10),3,5,8-tetraene-13-carboxylic acid tert-butyl ester was converted to the title compound by the methods described in Example 12E. APCI MS m/e 270.3 [(M+1)$^+$]. M.p. 129–130° C. (subl.).

EXAMPLE 21

7-PHENYL-5,7,13-TRIAZATETRACYCLO[9.3.1.0$^{2,10}$.0$^{4,8}$]-PENTADECA-2(10),3,5,8-TETRAENE HYDROCHLORIDE

Utilizing the methods described in Example 18A, 4,5-dinitro-10-aza-tricyclo[6.3.1.0$^{2,7}$]dodeca-2(7),3,5-triene-10-carboxylic acid tert-butyl ester and aniline were converted to 4-phenylamino-5-nitro-10-aza-tricyclo[6.3.1.0$^{2,10}$.0$^{4,8}$]dodeca-2(7),3,5-triene-10-carboxylic acid tert-butyl at 75° C. for 4 hours in the coupling step. This was then converted to the title compound utilizing the methods described in Example 18B,C,D. $^1$H NMR (400 MHz, DMSO-d$_6$) δ 9.08 (1H), 7.78–7.57 (m, 7H), 3.47–3.00 (m, 6H), 2.23 (m, 1H), 2.09 (d, J=11.5 Hz, 1H). APCI MS m/e 276.2 [(M+1)$^+$]. M.p. 210–213° C.

EXAMPLE 22

6-METHYL-7-PHENYL-5,7,13-TRIAZATETRACYCLO [9.3.1.0$^{2,10}$.0$^{4,8}$]-PENTADECA-2(10),3,5, 8-TETRAENE HYDROCHLORIDE

Utilizing the methods described in Example 21 and Example 20, 4,5-dinitro-10-aza-tricyclo[6.3.1.0$^{2,7}$]dodeca-2 (7),3,5-triene-10-carboxylic acid tert-butyl ester and aniline were converted to the title compound. $^1$H NMR (400 MHz, DMSO-d$_6$) δ 7.79 (s, 1H), 7.73–7.56 (m, 5H), 7.32 (s, 1H), 3.46–2.99 (m, 6H), 2.66 (s, 3H), 2.23 (m, 1H), 2.08 (d, J=11.0 Hz, 1H). APCI MS m/e 290.2 [(M+1)$^+$]. M.p.>250° C.

EXAMPLE 23

7-NEOPENTYL-5,7,13-TRIAZATETRACYCLO [9.3.1.0$^{2,10}$.0$^{4,8}$]-PENTADECA-2(10),3,5,8-TETRAENE HYDROCHLORIDE

Utilizing the methods described in Example 18A–D, 4,5-dinitro-10-aza-tricyclo[6.3.1.0$^{2,7}$]dodeca-2(7),3,5-triene-10-carboxylic acid tert-butyl ester and neopentylamine were converted to the title compound. t-Boc precursor GCMS m/e 369 (M$^+$). (HCl salt) M.p.>250° C.

EXAMPLE 24

6-METHYL-7-NEOPENTYL-5,7,13-TRIAZATETRACYCLO[9.3.1.0$^{2,10}$.0$^{4,8}$]PENTADECA-2(10),3, 5,8-TETRAENE HYDROCHLORIDE

Utilizing the methods described in Examples 21 and 20, 4,5-dinitro-10-aza-tricyclo[6.3.1.0$^{2,7}$]dodeca-2(7),3,5-triene-10-carboxylic acid tert-butyl ester and neopentylamine were converted to the title compound. $^1$H NMR (400 MHz, DMSO-d$_6$) δ 7.31 (s, 1H), 7.27 (s, H), 7.02 (br s, NH), 4.41 (t, J=13.0 Hz, 2H), 3.90 (s, 3H), 3.47–3.26 (m, 6H), 2.20 (m, 1H), 2.00 (d, J=11.5 Hz, 1H), 0.90 (s, 9H). t-Boc precursor APCI MS m/e 384.2 [(M+1)$^+$]. M.p.>250° C.

EXAMPLE 25

6,7-DIMETHYL-5,8,14-TRIAZATETRACYCLO [10.3.1.0$^{2,11}$.0$^{4,9}$]-HEXADECA-2(11),3,5,7,9-PENTAENE HYDROCHLORIDE (Based on the following procedure: Jones, R. G.; McLaughlin, K. C. *Org. Syn.* 1963, 4, 824. b) Ehrlich, J., Bobert, M. T. *J. Org. Chem.* 1947, 522.)

4,5-Diamino-10-aza-tricyclo[6.3.1.0$^{2,7}$]dodeca-2(7),3,5-triene-10-carboxylic acid tert-butyl ester (100 mg, 0.35 mmol) was warmed to 80° C. in H$_2$O (5 mL). To this butane 2,3-dione (0.034 mL, 0.38 mmol) was added under N$_2$ for 2 hours. The reaction was cooled to room temperature and extracted with ethyl acetate (3×40 ml). The combined organic layer was washed with H$_2$O (2×30 ml), dried (Na$_2$SO$_4$), filtered, concentrated and chromatographed on Silica gel to provide an oil (120 mg, 100%). The oil was dissolved in 2N HCl methanol (5 mL) and warmed to reflux for 30 minutes, then concentrated. Recrystallization from methanol/Et$_2$O provided a white powder (50 mg, 43%). (TLC ethyl acetate R$_f$ 0.14). $^1$H NMR (400 MHz, DMSO-d$_6$) δ 7.85 (s, 2H), 3.50 (br s, 2H), 3.32 (d, J=12.5 Hz, 2H), 3.10 (d, J=12.5 Hz, 2H), 2.64 (s, 6H), 2.24 (m, 1H), 2.13 (d, J=11.0 Hz, 1H). t-Boc precursor APCI MS m/e 340.3 [(M+1)$^+$].

EXAMPLE 26

5,8,14-TRIAZATETRACYCLO[10.3.1.0$^{2,11}$.0$^{4,9}$]-HEXADECA-2(11),3,5,7,9-PENTAENE HYDROCHLORIDE

A) 1-(4,5-Diamino-10-aza-tricyclo[6.3.1.0$^{2,7}$] dodeca-2(7),3,5-trien-10-yl)-2,2,2 trifluoro-ethanone 1-(4,5-Dinitro-10-aza-tricyclo[6.3.1.0$^{2,7}$]dodeca-2(7),3, 5-trien-10-yl)-2,2,2-trifluoro-ethanone (3.0 g, 8.70 mmol) was hydrogenated in methanol (30 ml) under H$_2$ (45 psi) over Pd(OH)$_2$ (300 mg of 20 wt %/C, 10% wt). After 2.5 hours the reaction was filtered through a Celite pad and rinsed with methanol (30 ml). The solution was concentrated to a light brown oil which crystallized (2.42 g, 96%). (TLC 10% methanol/CH$_2$Cl$_2$ R$_f$ 0.56). APCI MS m/e 286.2 [(M+1)$^+$]. M.p. 129–131° C.

B) 1-(5,8,14-Triazatetracyclo[10.3.1.0$^{2,11}$.0$^{4,9}$]hexadeca-2(11),3,5,7,9-pentaene)-2,2,2-trifluoro-ethanone 1-(4,5-Diamino-10-aza-tricyclo[6.3.1.0$^{2,7}$]dodeca-2(7),3, 5-trien-10-yl)-2,2,2-trifluoro-ethanone (500 mg, 1.75 mmol) was stirred in THF (2 ml). This mixture was treated with H$_2$O (2 mL) and glyoxal sodium bisulfite addition compound hydrate (931 mg, 3.50 mmol) then stirred at 55° C. for 2.5 hours. The reaction was cooled to room temperature and extracted with ethyl acetate (3×40 ml). The combined organic layer was washed with H$_2$O (2×30 ml), dried (Na$_2$SO$_4$), filtered, concentrated and chromatographed on Silica gel to provide an off white powder (329 mg, 60%). (TLC 25% ethyl acetate/hexanes R$_f$ 0.40). M.p. 164–166° C.

C) 5,8,14-Triazatetracyclo[10.3.1.0$^{2,11}$.0$^{4,9}$]hexadeca-2(11),3,5,7,9-pentaene hydrochloride 1-(5,8,14-Triazatetracyclo[10.3.1.0$^{2,11}$.0$^{4,9}$]hexadeca-2 (11),3,5,7,9-pentaene)-2,2,2-trifluoro-ethanone (320 mg, 1.04 mmol) was slurried in methanol (2.0 ml) and treated with Na$_2$CO$_3$ (221 mg, 2.08 mmol) in H$_2$O (2.0 ml). The mixture was warmed to 70° C. for 2 hours, then concentrated, treated with H$_2$O (20 mL) and extracted with CH$_2$Cl$_2$ (3×10 ml). The organic layer was dried through a cotton plug and concentrated to give a light yellow oil (183 mg, 83%) which solidified upon standing (M.p. 138–140° C.). This material was dissolved in methanol (10 mL), treated with 3M HCl/ethyl acetate (3 ml), concentrated and azeotroped with methanol (2×20 mL) to give solids which were recrystallized from methanol/Et$_2$O to afford product as a white solid (208 mg, 97%). (TLC 5% methanol/CH$_2$Cl$_2$ (NH$_3$) R$_f$ 0.26). $^1$H NMR (400 MHz, CD$_3$OD) δ 8.94 (s, 2H), 8.12 (s, 2H), 3.70 (m, 2H), 3.54 (d, J=12.5 Hz, 2H), 3.35 (d, J=12.5 Hz, 2H), 2.49 (m, 1H), 2.08 (d, J=11.0 Hz, 1H). GCMS m/e 211 (M$^+$). M.p. 225–230° C.

EXAMPLE 27

14-METHYL-5,8,14-TRIAZATETRACYCLO [10.3.1.0$^{2,11}$.0$^{4,9}$]-HEXADECA-2(11),3,5,7,9-PENTAENE HYDROCHLORIDE 5,8,14-Triazatetracyclo[10.3.1.0$^{2,11}$.0$^{4,9}$]hexadeca-2(11), 3,5,7,9-pentaene (207 mg, 0.98 mmol) was treated with 37% aqueous formaline solution (1 mL) and formic acid (1 mL) then warmed to 80° C. for 1 hour. The reaction was poured into water, made basic (NaOH, pH~11) and extracted with ethyl acetate. The organic layer was dried (Na$_2$SO$_4$), concentrated and chromatographed on Silica gel to provide a yellow solid. This was stirred in methanol (2 mL) and treated with 3N HCl ethyl acetate (2 mL). After concentration the solids were recrystallized from methanol/Et$_2$O to afford product as a white solid (70 mg, 27%). (2% methanol/CH$_2$Cl$_2$ (NH$_3$) R$_f$ 0.47). $^1$H NMR (400 MHz, CDCl$_3$) δ 8.71 (s, 2H), 7.80 (s, 2H), 3.37 (br s, 2H), 3.03 (m, 2H), 2.47 (m, 2H), 2.32 (m, 1H), 2.18 (br s, 3H), 1.84 (d, J=11.0 Hz, 1H). APCI MS m/e 226.2 [(M+1)$^+$]. M.p.>250° C.

EXAMPLE 28

5-OXA-7,13-DIAZATETRACYCLO[9.3.1.0$^{2,10}$.0$^{4,8}$]-PENTADECA-2(10),3,6,8-TETRAENE HYDROCHLORIDE

A) 2,2,2-Trifluoro-1-(4-hydroxy-5-nitro-10-azatricyclo[6.3.1.0$^{2,7}$]dodeca-2(7),3,5-trien-10-yl)-ethanone 1-(4,5-Dinitro-10-aza-tricyclo[6.3.1.0$^{2,7}$]dodeca-2(7),3, 5-trien-10-yl)-2,2,2-trifluoro-ethanone (900 mg, 2.61 mmol) and potassium acetate (KOAc) (2.6 g, 26.1 mmol) were dissolved in DMSO (10 mL) and warmed with stirring to 100° C. for 16 hours. The mixture was cooled and diluted with H$_2$O (50 mL) then extracted with 80% ethyl acetate/hexanes (6×25 mL). The organic layer was washed with H$_2$O (3×20 mL), dried (Na$_2$SO$_4$), filtered and concentrated and purified by chromatography to give an oil (575 mg, 70%). (TLC 50% ethyl acetate/hexanes (NH$_3$) R$_f$ 0.56)

B) 2,2,2-Trifluoro-1-(4-hydroxy-5-amino-10-azatricyclo[6.3.1.0$^{2,7}$]dodeca-2(7),3,5-trien-10-yl)-ethanone 2,2,2-Trifluoro-1-(4-hydroxy-5-nitro-10-aza-tricyclo [6.3.1.0$^{2,7}$]dodeca-2(7),3,5-trien-10-yl)-ethanone (575 mg, 1.82 mmol) was hydrogenated in methanol under a H$_2$ atmosphere at (45 psi) over 10% Pd/C (80 mg) for 1.5 hours then filtered through a Celite pad and concentrated to white solids (450 mg, 86%). (TLC 5% methanol/CH$_2$Cl$_2$ (NH$_3$) R$_f$ 0.6). $^1$H NMR (400 MHz, CD$_3$OD) δ 6.67–6.59 (m, 2H), 4.12 (m, 1H), 3.73 (m, 1H), 3.73 (m, 1H), 3.51 (m, 1H), 3.07 (m, 2H), 2.24 (m, 1H), 1.94 (d, J=10.5 Hz, 1H). GCMS m/e 286 (M$^+$).

C) 2,2,2-Trifluoro-1-(5-oxa-7,13-diazatetracyclo [9.3.1.0$^{2,10}$.0$^{4,8}$]pentadeca-2(10),3,6,8-tetraene)-ethanone (Goldstein, S. W.; Dambek, P. J. *J. Het. Chem.* 1990, 27, 335.)

2,2,2-Trifluoro-1-(4-hydroxy-5-amino-10-aza-tricyclo [6.3.1.0$^{2,7}$]dodeca-2(7),3,5-trien-10-yl)-ethanone (150 mg, 0.524 mmol), trimethyl orthoformate (0.19 mL, 1.73 mmol), pyridinium-p-toluenesulfonic acid (PPTS, 18 mg, 0.07 mmol) and xylenes (10 mL) were combined under nitrogen and stirred at 135° C. for 18 hours. The mixture was cooled, treated with H$_2$O and extracted with ethyl acetate. The extracts were dried (Na$_2$SO$_4$), filtered, concentrated and purified by chromatography to give an oil (110 mg, 71%). (TLC 20% ethyl acetate/hexanes R$_f$ 0.40)

D) 5-Oxa-7,13-diazatetracyclo[9.3.1.0$^{2,10}$.0$^{4,8}$]pentadeca-2(10),3,6,8-tetraene hydrochloride 2,2,2-Trifluoro-1-(5-oxa-7,13-diazatetracyclo[9.3.1.0$^{2,10}$.0$^{4,8}$]pentadeca-2(10),3,6,8-tetraene)-ethanone (110 mg, 0.37 mmol) was stirred in methanol (5 mL) and treated with Na$_2$CO$_3$ (78 mg, 0.74 mmol) in H$_2$O (2 mL). The stirred mixture was warmed to 80° C. for 2 hours, concentrated to solids, diluted with H$_2$O and extracted with ethyl acetate (3×40 mL). The product was extracted into aqueous 1N HCl solution (2×40 mL) which was washed with ethyl acetate then neutralized with saturated aqueous Na$_2$CO$_3$ solution to pH~10. The product was extracted with ethyl acetate (3×40 mL), dried (Na$_2$SO$_4$), concentrated and chromatographed on Silica gel to produce an oil. (TLC 5% methanol/CH$_2$Cl$_2$ (NH$_3$) R$_f$ 0.19).

The oil was dissolved in methanol and treated with 3N HCl ethyl acetate (4 mL) then concentrated, stirred in a minimum of CH$_2$Cl$_2$ and saturated with hexanes. After 18 hours, the product was collected by filtration (55 mg, 63%). $^1$H NMR (400 MHz, CD$_3$OD) δ 8.47 (s, 1H), 7.70 (s, 1H), 7.65 (s, 1H), 3.41 (m, 2H), 3.30 (m, 2H), 3.10 (d, J=12.5 Hz, 2H), 2.47 (m, 1H), 2.15 (d, J=11.0 Hz, 1H). APCI MS m/e 201.03 [(M+1)$^+$].

EXAMPLE 29

6-METHYL-5-OXA-7,13-DIAZATETRACYCLO [9.3.1.0$^{2,10}$.0$^{4,8}$]-PENTADECA-2(10),3,6,8-TETRAENE HYDROCHLORIDE

A) 2,2,2-Trifluoro-1-(6-methyl 5-oxa-7,13-diazatetracyclo[9.3.1.0$^{2,10}$.0$^{4,8}$]pentadeca-2(10),3,6,8-tetraene)-ethanone 2,2,2-Trifluoro-1-(4-hydroxy-5-amino-10-aza-tricyclo [6.3.1.0$^{2,7}$]dodeca-2(7),3,5-trien-10-yl)-ethanone (150 mg, 0.524 mmol), triethyl orthoacetate (0.34 mL, 1.83 mmol), pyridinium-p-toluenesulfonic acid (PPTS, 20 mg, 0.08 mmol) and xylenes (10 mL) were combined under nitrogen and stirred at 135° C. for 18 hours. Work-up, isolation and purification as in Example 28C provided the title compound (90 mg, 55%).

B) 6-Methyl-5-oxa-7,13-diazatetracyclo[9.3.1. 0$^{2,10}$.0$^{4,8}$]pentadeca-2(10),3,6,8-tetraene hydrochloride 2,2,2-Trifluoro-1-(6-methyl 5-oxa-7,13-diazatetracyclo [9.3.1.0$^{2,10}$.0$^{4,8}$]pentadeca-2(10),3,6,8-tetraene)-ethanone (90 mg, 0.30 mmol) was stirred in methanol (5 mL) and treated with Na$_2$CO$_3$ (61 mg, 0.58 mmol) in H$_2$O (2 mL). The stirred mixture was warmed to 80° C. for 2 hours, concentrated to solids, diluted with H$_2$O and extracted with ethyl acetate (3×40 mL). The solution was dried (Na$_2$SO$_4$), concentrated, and chromatographed on Silica gel to produce an oil. (TLC 10% methanol/CH$_2$Cl$_2$ (NH$_3$) R$_f$ 0.18). $^1$H NMR (free base) (400 MHz, CDCl$_3$) δ 7.40 (s, 1H), 7.26 (s, 1H), 3.05–2.98 (m, 4H), 2.72 (d, J=12.8 Hz, 2H), 2.59 (s, 3H), 2.46 (m, 1H), 1.98 (d, J=10.5 Hz, 1H).

The oil was dissolved in methanol and treated with 3N HCl ethyl acetate (4 mL) then concentrated, stirred in a minimum of $CH_2Cl_2$ and saturated with hexanes. After 18 hours, the product was collected by filtration (10 mg, 13%). APCI MS m/e 215.2 [(M+1)$^+$]. M.p.>250° C.

EXAMPLE 30

2-FLUORO-N-(4-HYDROXY-10-AZA-TRICYCLO [6.3.1.0$^{2,7}$]-DODECA-2(7),3,5-TRIEN-5-YL)-BENZAMIDE HYDROCHLORIDE 2,2,2-Trifluoro-1-(4-hydroxy-5-amino-10-aza-tricyclo [6.3.1.0$^{2,7}$]dodeca-2(7),3,5-trien-10-yl)-ethanone (150 mg, 0.524 mmol), 2-fluorobenzoyl chloride (0.07 mL, 0.576 mmol), pyridinium-p-toluenesulfonic acid (PPTS, 20 mg, 0.08 mmol), pyridine (0.046 mL, 0.576 mmol) and xylenes (5 mL) were combined under nitrogen and stirred at 135° C. for 18 hours. After 24 hours, additional PPTS (50 mg) was added and the material stirred at 135° C. for an additional 24 hours. Work-up as above provided crude product (145 mg, 0.375 mmol) which was combined with $Na_2CO_3$(s) (80 mg, 0.75 mmol) in methanol (5 mL) and $H_2O$ (2 mL) and heated to reflux. After 3 hours, the reaction was cooled and diluted with water then extracted with $CH_2Cl_2$ (4×40 mL), dried through a cotton plug then chromatographed to remove baseline impurity (5% methanol/$CH_2Cl_2$ ($NH_3$)). The crude material was treated with excess 3N HCl ethyl acetate and concentrated, then dissolved in a minimum of methanol and the solution was saturated with $Et_2O$ and stirred. After stirring 4 hours the product was collected by filtration (85 mg, 68%). $^1$H NMR (400 MHz, CD$_3$OD) δ 7.99 (m, 2H), 7.59 (m, 1H), 7.36–7.23 (m, 2H), 6.82 (s, 1H), 2.99 (m, 4H), 2.78 (m, 2H), 2.35 (m, 1H), 1.96 (d, J=10.5 Hz, 1H). APCI MS m/e 313.1 [(M+1)$^+$]. M.p. 125–130° C. (subl.).

EXAMPLE 31

4-CHLORO-10-AZATRICYCLO[6.3.1.0$^{2,7}$] DODECA-2(7),3,5-TRIENE HYDROCHLORIDE

A) 1-(4-Chloro-10-aza-tricyclo[6.3.1.0$^{2,7}$]dodeca-2 (7),3,5-trien-10-yl)-2,2,2-trifluoro-ethanone Copper(1)chloride (CuCl) was prepared as follows: $CuSO_4$ (4.3 g) and NaCl (1.2 g) were dissolved in hot $H_2O$ (14 mL). sodium bisulfite ($NaHSO_3$) (1 g) and sodium hydroxide (NaOH) (690 mg) were dissolved in $H_2O$ (7 mL) and added to the hot acidic solution over 5 minutes. The precipitated white solids were filtered and washed with water.

1-(4-Amino-10-aza-tricyclo[6.3.1.0$^{2,7}$]dodeca-2(7),3,5-trien-10-yl)-2,2,2-trifluoro-ethanone (460 mg, 1.7 mmol) was dissolved in $H_2O$ (2 mL) and concentrated HCl solution (1 mL) then cooled to 0° C. and treated with a solution of sodium nitrite (NaNO$_2$) (275 mg) in $H_2O$ (1 mL) dropwise. To the resulting solution was added a CuCl (202 mg, prepared as described above, 2.04 mmol) in concentrated HCl solution (2 mL) over 10 minutes (gas evolution observed). The resulting solution was warmed to 60° C. for 15 minutes, then was cooled to room temperature and extracted with ethyl acetate (4×30 mL). After drying over $Na_2SO_4$, the solution was filtered and concentrated to an oil which was filtered through a Silica pad to remove baseline material eluting with 50% ethyl acetate/hexanes to give an oil (470 mg, 95%).

B) 4-Chloro-10-azatricyclo[6.3.1.0$^{2,7}$]dodeca-2(7),3, 5-triene hydrochloride 1-(4-Chloro-10-aza-tricyclo[6.3.1.0$^{2,7}$]dodeca-2(7),3,5-trien-10-yl)-2,2,2-trifluoro-ethanone (470 mg, 1.62 mmol) and $Na_2CO_3$ (344 mg, 3.24 mmol) in methanol (30 mL) and $H_2O$ (10 mL) were heated to reflux. After 2 hours, the reaction was cooled and diluted with water then extracted with ethyl acetate (4×40 mL), dried ($Na_2SO_4$), filtered and concentrated to a yellow oil. The crude material was treated with excess 3N HCl ethyl acetate and concentrated, then dissolved in a minimum of $CH_2Cl_2$ and the solution was saturated with hexanes and stirred. After stirring 4 hours the product was collected by filtration (155 mg, 42%). $^1$H NMR (free base) (400 MHz, CDCl$_3$) δ 7.15 (m, 2H), 7.09 (d, J=8.0 Hz, 1H), 3.00–2.94 (m, 4H), 2.68, (m, 2H), 2.38 (m, 1H), 1.92 (d, J=10.5 Hz, 1H). $^1$H NMR (HCl salt) (400 MHz, DMSO-d$_6$) δ 7.30–7.20 (m, 3H), 3.30–3.15 (m, 6H), 2.37 (m, 1H), 1.89 (d, J=11.0 Hz, 1H). APCI MS m/e 194.1 [(M+1)$^+$].

EXAMPLE 32

10-AZATRICYCLO[6.3.1.0$^{2,7}$]DODECA-2(7),3,5-TRIEN-4-YL CYANIDE HYDROCHLORIDE

A) 1-(4-Iodo-10-aza-tricyclo[6.3.1.0$^{2,7}$]dodeca-2(7), 3,5-trien-10-yl)-2,2,2-trifluoro-ethanone 1-(4-Amino-10-aza-tricyclo[6.3.1.0$^{2,7}$]dodeca-2(7),3,5-trien-10-yl)-2,2,2-trifluoro-ethanone (500 mg, 1.85 mmol) was dissolved in $H_2O$ (5 mL) and concentrated $H_2SO_4$ solution (0.5 mL) then cooled to 0° C. and treated with a solution of sodium nitrite (NaNO$_2$) (140 mg, 2.04 mmol) in $H_2O$ (2 mL) dropwise. Potassium iodide (460 mg, 2.78 mmol) in 1N $H_2SO_4$ solution (0.5 mL) was added over 10 minutes (reaction becomes dark red). The resulting solution was warmed to room temperature and stirred 18 hours. The reaction was quenched with $NaHSO_3$ and water (pH 2.5) then extracted with ethyl acetate (4×30 mL). After drying ($Na_2SO_4$), the solution was filtered and concentrated to a yellow oil which was chromatographed on Silica gel to provide a yellow oil. (260 mg, 37%). (TLC 30% ethyl acetate/hexanes R$_f$ 0.70). (A 5.4 g scale performed as above yielded 5 g, 67%).

B) 4-Iodo-10-aza-tricyclo[6.3.1.0$^{2,7}$]dodeca-2(7),3, 5-triene-10-carboxylic acid tert-butyl ester 1-(4-Iodo-10-aza-tricyclo[6.3.1.0$^{2,7}$]dodeca-2(7),3,5-trien-10-yl)-2,2,2-trifluoro-ethanone (5 g, 13.1 mmol) and 37% saturated aqueous $NH_4OH$ solution (50 mL) were stirred in methanol (250 ml) for 2 hours then concentrated and azeotroped with methanol (2×50 mL). The resulting product was stirred in 1,4-dioxane (75 mL) and treated with saturated $Na_2CO_3$ solution (15 mL). To this was added di-t-butyldicarbonate (5.71 g, 26.2 mmol). After stirring 18 hours the reaction was treated with $H_2O$ (50 mL) and extracted with $CH_2Cl_2$ (4×30 mL), dried ($Na_2SO_4$), filtered, concentrated and chromatographed on Silica gel (TLC 20% ethyl acetate/hexanes) to provide product as an oil (4.9 g, 98%).

C) 4-Cyano-10-aza-tricyclo[6.3.1.0$^{2,7}$]dodeca-2(7), 3,5-triene-10-carboxylic acid tert-butyl ester (Utilizing the methods described in: House, H. O.; Fischer, W. F. *J. Org. Chem.* 1969, 3626.)

CuCN (108 mg, 1.21 mmol) and NaCN (59 mg, 1.21 mmol) were combined in dry DMF (6 mL) and warmed to 150° C. under $N_2$. Solution occurs in 20 minutes. To this was added 4-iodo-10-aza-tricyclo[6.3.1.0$^{2,7}$]dodeca-2(7),3,5-triene-10-carboxylic acid tert-butyl ester (232 mg, 0.6 mmol) in DMF (3.5 mL) and the mixture was stirred for 18 hours at 150° C. The reaction was cooled and diluted with 50% saturated aqueous NaCl solution and extracted with 50% ethyl acetate/hexanes (3×30 mL). After drying ($Na_2SO_4$), filtration and concentration the product was isolated by chromatography (86 mg, 50%). (TLC 20% ethyl acetate/hexanes $R_f$ 0.28).

D) 10-Azatricyclo[6.3.1.0$^{2,7}$]dodeca-2(7),3,5-trien-4-yl cyanide hydrochloride 4-Cyano-10-aza-tricyclo[6.3.1.0$^{2,7}$]dodeca-2(7),3,5-triene-10-carboxylic acid tert-butyl ester was treated with 3N HCl ethyl acetate (6 mL) and warmed to reflux for 2 hours, then concentrated, dissolved in a minimum of methanol which was saturated with $Et_2O$ and stirred 18 hours. The product was collected by filtration (49 mg, 73%). $^1$H NMR (400 MHz, DMSO-d$_6$) δ 9.66 (br s, NH), 7.86 (br s, NH), 7.74–7.70 (m, 2H), 7.49 (d, J=7.5 Hz, 1H), 3.33–2.97 (m, 6H), 2.17 (m, 1H), 2.01 (d, J=11.0 Hz, 1H). GCMS m/e 184 (M$^+$). M.p. 268–273° C.

EXAMPLE 33

3-(10-AZATRICYCLO[6.3.1.0$^{2,7}$]DODECA-2(7),3,5-TRIEN-4-YL)-5-M ETHYL-1,2,4-OXADIAZOLE HYDROCHLORIDE

4-Cyano-10-aza-tricyclo[6.3.1.0$^{2,7}$]dodeca-2(7),3,5-triene-10-carboxylic acid tert-butyl ester (300 mg, 1.1 mmol) was stirred in ethanol (10 mL). To this hydroxyl amine hydrochloride (382 mg, 5.5 mmol) and NaOH (242 mg, 6.05 mmol) were added and the mixture was warmed to reflux. After 45 minutes, the reaction was cooled, diluted with $H_2O$ and extracted with ethyl acetate. The organic layer was dried ($Na_2SO_4$) and concentrated to afford a yellow solid (110 mg, 0.35 mmol). This solid was dissolved in pyridine (1 mL) and treated with acetyl chloride (0.03 mL, 0.415 mmol) and warmed to 100° C. for 18 hours. The reaction was cooled, treated with $H_2O$ and extracted with ethyl acetate. The organic extracts were washed with water and saturated aqueous NaCl solution, dried ($Na_2SO_4$) and concentrated. Chromatography on Silica gel afforded product (50 mg, 0.15 mmol). (25% ethyl acetate/hexanes $R_f$ 0.18). This product was treated with 2N HCl methanol (10 mL), heated to 70° C. for 1 hour, cooled, concentrated and recrystallized from methanol/$Et_2O$ to provide product (15 mg). APCI MS m/e 242.2 [(M+1)$^+$].

EXAMPLE 34

1-(10-AZATRICYCLO[6.3.1.0$^{2,7}$]DODECA-2(7),3,5-TRIEN-4-YL)-1-ETHANONE HYDROCHLORIDE

A) 1-(4-Acetyl-10-aza-tricyclo[6.3.1.0$^{2,7}$]dodeca-2(7),3,5-trien-10-yl)-2,2,2-trifluoro-ethanone 1-(10-Aza-tricyclo[6.3.1.0$^{2,7}$]dodeca-2(7),3,5-trien-10-yl)-2,2,2-trifluoro-ethanone (253 mg, 1.0 mmol) and AcCl (0.68 mL, 10 mmol) were dissolved in DCE (3 mL) and treated with aluminum chloride ($AlCl_3$) (667 mg, 5.0 mmol). The resulting yellow mixture was stirred for 30 minutes then poured over ice and saturated aqueous $NaHCO_3$ solution. After stirring 20 minutes the mixture was extracted with $CH_2Cl_2$ (3×30 mL). The organic layer was dried through a cotton plug then concentrated to a orange-yellow oil (255 mg, 86%).

B) 4-Acetyl-10-aza-tricyclo[6.3.1.0$^{2,7}$]dodeca-2(7), 3,5-triene-10-carboxylic acid tert-butyl ester 1-(4-Acetyl-10-aza-tricyclo[6.3.1.0$^{2,7}$]dodeca-2(7),3,5-trien-10-yl)-2,2,2-trifluoro-ethanone (1.3 g, 4.37 mmol) and 37% aqueous $NH_4OH$ solution (10 mL) were stirred in methanol (30 ml) for 3 hours, then concentrated and azeotroped with methanol (2×50 mL). (This product could be converted to an HCl salt directly: see the next example.) The resulting product was stirred in 1,4-dioxane (20 mL) and treated with saturated aqueous $Na_2CO_3$ solution (5 mL). To this was added di-t-butyldicarbonate (1.91 g, 8.74 mmol). After stirring 2 hours, the reaction was treated with $H_2O$ (50 mL), extracted with $CH_2Cl_2$ (4×30 mL), dried ($Na_2SO_4$), filtered, concentrated and chromatographed to provide an oil (1.3 g, 100%). (TLC 40% ethyl acetate/hexanes $R_f$ 0.56).

C) 1-(10-Azatricyclo[6.3.1.0$^{2,7}$]dodeca-2(7),3,5-trien-4-yl)-1-ethanone hydrochloride 4-Acetyl-10-aza-tricyclo[6.3.1.0$^{2,7}$]dodeca-2(7),3,5-triene-10-carboxylic acid tert-butyl ester (190 mg, 0.63 mmol) was treated with excess 3N HCl ethyl acetate and warmed to 70° C. for 1 hour then concentrated and dissolved in a minimum of methanol. The resulting solution was saturated with $Et_2O$ and stirred. After 18 hours the white crystalline product was collected by filtration (81 mg, 54%). $^1$H NMR (400 MHz, DMSO-d$_6$) δ 9.75 (br s, NH), 7.89 (s, 1H), 7.88 (d, J=8.0 Hz, 1H), 7.74 (br s, NH), 7.44 (d, J=8.0 Hz, 1H), 3.33 (br s, 2H), 3.22 (br s, 2H), 3.00 (br m, 2H), 2.54 (s, 3H), 2.17 (m, 1H), 2.02 (d, J=11.0 Hz, 1H). GCMS m/e 201 (M$^+$). M.p. 198–202° C.

EXAMPLE 35

10-AZATRICYCLO[6.3.1.0$^{2,7}$]DODECA-2(7),3,5-TRIEN-4-OL HYDROCHLORIDE

A) Acetic acid 10-trifluoroacetyl-10-aza-tricyclo[6.3.1.0$^{2,7}$]dodeca-2(7),3,5-trien-4-yl ester 1-(4-Acetyl-10-aza-tricyclo[6.3.1.0$^{2,7}$]dodeca-2(7),3,5-trien-10-yl)-2,2,2-trifluoro-ethanone (2.5 g, 8.41 mmol) and 3-chloroperoxybenzoic acid (m-CPBA) (7.5 g, 42 mmol) were stirred in $CH_2Cl_2$ (20 mL) and warmed to 40° C. for 18 hours. The mixture was cooled to room temperature, then treated with dimethylsulfide ($Me_2S$) (3 mL, 40.8 mmol) and stirred 24 hours. The resulting mixture was poured into ice and saturated aqueous Na$_2$CO$_3$ solution (100 mL) then extracted with Et$_2$O (4×40 mL). The organic layer was washed saturated aqueous Na$_2$CO$_3$ solution (3×40 mL) then dried (Na$_2$SO$_4$), filtered and concentrated to afford an oil (1.83 g, 69%). (TLC ethyl acetate R$_f$ 0.80).

B) 2,2,2-Trifluoro-1-(4-hydroxy-10-aza-tricyclo [6.3.1.0$^{2,7}$]dodeca-2(7),3,5-trien-10-yl)-ethanone Acetic acid 10-trifluoroacetyl-10-aza-tricyclo[6.3.1.0$^{2,7}$] dodeca-2(7),3,5-trien-4-yl ester (900 mg, 2.87 mmol) was stirred in methanol (20 mL) and saturated aqueous NaHCO$_3$ solution (15 mL) for 48 hours. The mixture was concentrated, diluted with H$_2$O and extracted with CH$_2$Cl$_2$ (3×20 mL) then dried through a cotton plug. Chromatography on Silica gel provided pure product (420 mg, 54%). (TLC 5% methanol/CH$_2$Cl$_2$ R$_f$ 0.44). $^1$H NMR (400 MHz, CDCl$_3$) δ 7.05 (m, 1H), 6.70 (m, 1H), 6.62 (m, 1H), 4.32 (m, 1H), 3.84 (m, 1H), 3.48 (m, 1H), 3.21 (br s, 1H), 3.16 (br s, 1H), 3.09 (m, 1H), 2.38 (m, 1H), 1.97 (d, J=11.0 Hz, 1H).

C) 10-Azatricyclo[6.3.1.0$^{2,7}$]dodeca-2(7),3,5-trien-4-ol hydrochloride 2,2,2-Trifluoro-1-(4-hydroxy-10-aza-tricyclo[6.3.1.0$^{2,7}$] dodeca-2(7),3,5-trien-10-yl)-ethanone (50 mg, 0.184 mmol) was dissolved in methanol/H$_2$O (3/1, 5 mL), treated with Na$_2$CO$_3$(s) (40 mg, 0.369 mmol) and warmed to 65° C. for 2 hours. The mixture was concentrated, diluted with H$_2$O and extracted with CH$_2$Cl$_2$ (3×20 mL) then dried through a cotton plug. Filtration through a Silica gel plug provided an oil (10% methanol/CH$_2$Cl$_2$) which was treated with 3N HCl ethyl acetate (3 mL) then concentrated, dissolved in a minimum of methanol which was saturated with Et$_2$O and stirred. After 18 hours the white crystalline product was collected by filtration (10 mg, 26%). $^1$H NMR (400 MHz, CDOD$_3$) δ 7.16 (d, J=8.0 Hz, 1H), 6.80 (d, J=2.0 Hz, 1H), 6.72 (dd, J=8.0,2.0 Hz, 1H), 3.32–3.28 (4H), 3.09 (dd, J=14.5,12.0 Hz, 2H), 2.32 (m, 1H), 2.03 (d, J=11.0 Hz, 1H). APCI MS m/e 176.2 [(M+1)$^+$]. M.p. 308 (dec.)° C.

EXAMPLE 36

7-METHYL-5-OXA-6,13-DIAZATETRACYCLO [9.3.1.0$^{2,10}$.0$^{4,8}$]PENTADECA-2,4(8),6,9-TETRAENE HYDROCHLORIDE

A) 1-(4-Acetyl-5-hydroxy-10-aza-tricyclo[6.3.1.0$^{2,7}$] dodeca-2(7),3,5-trien-10-yl)-2,2,2-trifluoro-ethanone Acetic acid 10-trifluoroacetyl-10-aza-tricyclo[6.3.1.0$^{2,7}$] dodeca-2(7),3,5-trien-4-yl ester (800 mg, 2.55 mmol) was combined with AlCl$_3$ (1.0 g, 7.65 mmol) and warmed to 170° C. for 2 hours. The mixture was cooled and treated with 1N aqueous HCl solution (20 mL), extracted with ethyl acetate and dried (Na$_2$SO$_4$). Chromatography affords an oil (190 mg, 24%). (TLC ethyl acetate R$_f$ 0.75). $^1$H NMR (400 MHz, CDCl$_3$) δ 12.58 (s, 0.5H), 12.52 (s, 0.5H), 7.53 (s, 1H), 6.86 (s, 1H), 4.33 (m, 1H), 3.91 (m, 1H), 3.56 (m, 1H), 3.28 (br s, 1H), 3.24 (br s, 1H), 3.14 (m, 1H), 2.35 (m, 1H), 1.97 (br d, J=11.2 Hz, 1H).

B) 2,2,2-Trifluoro-1-[4-hydroxy-5-(1-hydroxyimino-ethyl)-10-aza-tricyclo[6.3.1.0$^{2,7}$]-dodeca-2(7),3,5-trien-10-yl]-ethanone 1-(4-Acetyl-5-hydroxy-10-aza-tricyclo[6.3.1.0$^{2,7}$] dodeca-2(7),3,5-trien-10-yl)-2,2,2-trifluoro-ethanone (190 mg, 0.605 mmol), hydroxylamine HCl (99 mg, 1.21 mmol) and sodium acetate (118 mg, 1.21 mmol) were combined in methanol (4 mL) and H$_2$O (1 mL) and warmed to 65° C. for 18 hours. The mixture was cooled, diluted with H$_2$O and extracted with ethyl acetate which was dried (Na$_2$SO$_4$), filtered and concentrated to provide a yellow oil (177 mg, 93%).

C) 2,2,2-Trifluoro-7-Methyl-5-oxa-6,13-diazatetra-cyclo[9.3.1.0$^{2,10}$.0$^{4,8}$]pentadeca-2,4(8),6,9-tetraene-ethanone The above oil, 2,2,2-trifluoro-1-[4-hydroxy-5-(1-hy-droxyimino-ethyl)-10-aza-tricyclo[6.3.1.0$^{2,7}$]dodeca-2(7),3,5-trien-10-yl]-ethanone (177 mg, 0.54 mmol) was stirred in DCE (3 mL), treated with triethylamine (0.4 mL, 2.8 mmol) and acetic anhydride (Ac$_2$O) (0.3 mL, 2.8 mmol) then stirred 18 hours. The reaction was treated with H$_2$O and extracted with ethyl acetate. The extracts were dried (Na$_2$SO$_4$), filtered and concentrated to a yellow oil which was dissolved in anhydrous DMF (3 mL) and treated with 60% NaH in oil (32 mg, 1.08 mmol). After stirring 18 hours, additional 60% NaH in oil was introduced (33 mg) and the mixture was stirred 2 hours. The reaction was quenched with H$_2$O (5 mL) and extracted with 80% ethyl acetate/hexanes (3×30 mL). The organic layer was washed with H$_2$O (3×20 mL), dried (Na$_2$SO$_4$), filtered and concentrated and chromatographed to provide an oil (40% ethyl acetate/hexanes R$_f$ 0.56).

D) 7-Methyl-5-oxa-6, 13-diazatetracyclo[9.3.1. 0$^{2,10}$.0$^{4,8}$]pentadeca-2,4(8),6,9-tetraene hydrochloride Utilizing the methods described in Example 9C, 2,2,2-Trifluoro-7-Methyl-5-oxa-6,13-diazatetracyclo [9.3.1.0$^{2,10}$.0$^{4,8}$]pentadeca-2,4(8),6,9-tetraene-ethanone was converted to the title compound. This was treated with 3N HCl ethyl acetate (3 mL), concentrated and dissolved in a minimum of CH$_2$Cl$_2$ which was saturated with hexanes and stirred. After 18 hours the white crystalline product was collected by filtration (18 mg, 13% overall). $^1$H NMR (400 MHz, DMSO-d$_6$) δ 7.72 (s, 1H), 7.63 (s, 1H), 3.42–2.98 (m, 6H), 2.50 (s, 3H), 2.23 (m, 1H), 2.08 (d, J=10.5 Hz, 1H). APCI MS m/e 215.2 [(M+1)+]

EXAMPLE 37

4-(2-METHYL-2H-PYRAZOL-3-YL)-10-AZA-TRICYCLO[6.3.1.0$^{2,7}$]DODECA-2(7),3,5TRIENE HYDROCHLORIDE and 4-(1-METHYL-1H-PYRAZOL-3-YL)-10-AZA-TRICYCLO[6.3.1.0$^{2,7}$] DODECA-2(7),3,5-TRIENE HYDROCHLORIDE 1-(4-Acetyl-10-aza-tricyclo[6.3.1.0$^{2,7}$]dodeca-2(7),3,5-trien-10-yl)-2,2,2-trifluoro-ethanone (1.0 g, 3.3 mmol) and dimethylformamide dimethylacetal (DMF-DMA) (4.0 g, 33.6 mmol) were warmed to 140° C. for 18 hours. After cooling, a crystalline precipitate was filtered and rinsed with ethyl acetate (690 mg, 58%).

The above solid, 3-dimethylamino-1-(10-trifluoroacetyl-10-aza-tricyclo[6.3.1.0$^{2,7}$]-dodeca-2(7),3,5-trien-4-yl)-propenone, (200 mg, 0.56 mmol) was dissolved in ethanol (2 mL) and treated with 5N HCl ethanol (0.1 mL) followed by methyl hydrazine (0.6 mmol). The resulting mixture was warmed to 70° C. for 4 hours. The mixture was cooled, diluted with water and extracted with ethyl acetate, dried (Na$_2$SO$_4$) and concentrated. Chromatography on Silica gel provided a 3/1 mixture of regioisomeric products (130 mg, 68%). (TLC 50% ethyl acetate/hexanes R$_f$ 0.40).

The above oil (130 mg, 0.388 mmol) and Na$_2$CO$_3$(s) (82 mg, 0.775 mmol) were stirred in methanol (10 mL) and H$_2$O (5 mL) for 18 hours. After cooling the reaction was diluted with water, extracted with CH$_2$Cl$_2$ dried through a cotton plug and concentrated. The product was purified by chromatography on Silica gel and concentrated to an oil. The salt was generated with 2N HCl methanol, concentrated and recrystallized from methanol/ethyl acetate to provide a 3/1 mixture of regioisomeric pyrrazoles (85 mg, 58%). (5% methanol/CH$_2$Cl$_2$ (NH$_3$) R$_f$ 0.25). TFA-precursor APCI MS m/e 336.2 [(M+1) $^+$].

EXAMPLE 38

4,5-DICHLORO-10-AZATRICYCLO[6.3.1.0$^{2,7}$] DODECA-2(7),3,5-TRIENE HYDROCHLORIDE

A) 1-(4,5-Dichloro-10-aza-tricyclo[6.3.1.0$^{2,7}$] dodeca-2(7),3,5-trien-10-yl)-2,2,2-trifluoro-ethanone (Based on Campaigne, E.; Thompson, W. *J. Org. Chem.* 1950, 72, 629.)

1-(10-Aza-tricyclo[6.3.1.0$^{2,7}$]dodeca-2(7),3,5-trien-10-yl)-2,2,2-trifluoro-ethanone (539 mg, 2.1 mmol) was stirred in CH$_2$Cl$_2$ (5 mL) and treated with ICl$_3$ (s) (982 mg, 4.21 mmol). The resulting orange solution was stirred 0.5 hours, poured into saturated aqueous NaHSO$_3$ solution (25 mL), extracted with CH$_2$Cl$_2$ (3×25 mL), dried through a cotton plug and concentrated to an oil (570 mg, 84%) (TLC 50% ethyl acetate/hexanes R$_f$ 0.62).

B) 4,5-dichloro-10-azatricyclo[6.3.1.0$^{2,7}$]dodeca-2(7),3,5-triene hydrochloride 1-(4,5-Dichloro-10-aza-tricyclo[6.3.1.0$^{2,7}$]dodeca-2(7),3,5-trien-10-yl)-2,2,2-trifluoro-ethanone (570 mg, 1.75 mmol) was stirred in methanol (25 mL) and treated with Na$_2$CO$_3$(s) (5 g, 47 mmol) in H$_2$O (5 mL). The stirred mixture was warmed to 70° C. for 4 hours, concentrated to solids, diluted with H$_2$O and extracted with ethyl acetate (3×40 mL). The product was extracted into 1N aqueous HCl solution (2×40 mL) which was washed with ethyl acetate then neutralized with saturated aqueous Na$_2$CO$_3$ solution to pH~10. Product was extracted with CH$_2$Cl$_2$ (3×40 mL), filtered through a cotton plug and concentrated to an oil (400 mg, 100%).

The oil was dissolved in methanol and treated with 3N HCl ethyl acetate (4 mL) and concentrated, then dissolved in a minimum of methanol and which was saturated with Et$_2$O and stirred 18 hours. The product was collected by filtration (210 mg, 45%). (TLC 50% ethyl acetate/hexanes (NH$_3$) R$_f$ 0.08). $^1$H NMR (400 MHz, DMSO-d$_6$) δ 7.58 (s, 2H), 3.33–2.97 (m, 6H), 2.18 (m, 1H), 1.99 (d, J=10.5 Hz, 1H). $^{13}$C NMR (100 MHz,DMSO-d$_6$) δ 141.02, 130.60, 126.58, 45.54, 40.55, 38.30. GCMS m/e 227, 229 (M$^+$). M.p. 283–291° C.

EXAMPLE 39

N$^4$,N$^4$-DIMETHYL-10-AZATRICYCLO[6.3.1. 0$^{2,7}$]-DODECA-2(7),3,5-TRIENE-4-SULFONAMIDE HYDROCHLORIDE

A) 10-Trifluoroacetyl-10-aza-tricyclo[6.3.1.0$^{2,7}$] dodeca-2(7),3,5-triene-4-sulfonyl chloride 1-(10-Aza-tricyclo[6.3.1.0$^{2,7}$]dodeca-2(7),3,5-trien-10-yl)-2,2,2-trifluoro-ethanone (530 mg, 2.1 mmol) was added to chlorosulfonic acid (2 mL, 30 mmol) and stirred for 5 minutes. The mixture was quenched with ice, extracted with ethyl acetate, dried (Na$_2$SO$_4$), filtered and concentrated to provide an oil (640 mg, 87%). (TLC 30% ethyl acetate/hexanes R$_f$ 0.15).

B) N$^4$,N$^4$-Dimethyl-10-azatricyclo[6.3.1.0$^{2,7}$] dodeca-2(7),3,5-triene-4-sulfonamide hydrochloride 10-Trifluoroacetyl-10-aza-tricyclo[6.3.1.0$^{2,7}$]dodeca-2(7),3,5-triene-4-sulfonyl chloride (320 mg, 0.9 mmol) was stirred in THF (10 mL) and treated with 40% Me$_2$NH/H$_2$O (1.5 mL). After 10 minutes the mixture was concentrated and chromatographed on Silica gel (TLC 30% ethyl acetate/hexanes R$_f$ 0.31) to provide an oil (256 mg, 78%). This material was dissolved in methanol (6 mL) and NH$_4$OH (2 mL) and stirred 18 hours. The mixture was concentrated and azeotroped from methanol (3 times) The resulting oil was dissolved in methanol and treated with 3N HCl ethyl acetate (4 mL), concentrated, dissolved in a minimum of methanol and which was saturated with Et$_2$O and stirred 18 hours. The product was collected by filtration as a white powder (163 mg, 59%). (TLC 10% methanol/CH$_2$Cl$_2$ (NH$_3$) R$_f$ 0.54). $^1$H NMR (data, free base) (400 MHz, CDCl$_3$) δ 7.64 (m, 2H), 7.41 (d, J=8.0 Hz, 1H), 3.30 (m, 2H), 3.20 (d, J=12.5 Hz, 2H), 3.07 (dd, J=12.5,2.2 Hz, 2H), 2.69 (s, 6H), 2.45, (m, 1H), 2.00 (d, J=11.0 Hz, 1H). $^{13}$C NMR (100 MHz, CDCl$_3$) δ 128,43, 124.16, 122,75, 46.67, 46.55, 42.11, 39, 44, 37,81. GCMS m/e 266 (M$^+$). (data HCl salt) $^1$H NMR (400 MHz, DMSO-d$_6$) δ 7.68–7.52 (3H), 3.38 (m, 2H), 3.24 (m, 2H), 3.04 (m,-2H), 2.58 (s, 6H), 2.22 (m, 1H), 2.04 (d, J=11.0 Hz, 1H). GCMS m/e 266 (M$^+$). Anal. Calcd. for C$_{13}$H$_{18}$N$_2$O$_2$HCl: C, 51.56; H, 6.32; N, 9.25. Found C, 51.36; H,6.09; N,9.09.

EXAMPLE 40

4-(1-PYRROLIDINYLSULFONYL)-10-AZATRICYCLO[6.3.1.0$^{2,7}$]-DODECA-2(7),3,5-TRIENE HYDROCHLORIDE

The pyrrolidine analogue was prepared from 10-trifluoroacetyl-10-aza-tricyclo[6.3.1.0$^{2,7}$]dodeca-2(7),3,5-triene-4-sulfonyl chloride (320 mg, 0.9 mmol) as by substituting pyrroline in the coupling step described in Example 39B. The TFA product was isolated as an oil (314 mg, 89%). Deprotection and conversion to the salt as in Example 39B affords a white powder (189 mg, 63%). (TLC 10% methanol/CH$_2$Cl$_2$ (NH$_3$) R$_f$ 0.60). (TLC 50% ethyl acetate/hexanes R$_f$ 0.65). $^1$H NMR (400 MHz, CDCl$_3$) δ 7.66 (d, J=8.0 Hz, 1H), 7.64 (s, 1H), 7.37 (d, J=8.0 Hz, 1H), 3.30–3.15 (m, 8H), 3.00 (m 2H), 2.39 (m, 1H), 1.98 (d, J=11.5 Hz, 1H), 1.72 (m, 4H). $^{13}$C NMR (100 MHz, CDCl$_3$) δ 146.91, 144.08, 136.65, 127.90, 124.18, 122.36, 50.43, 47.87, 46.80, 46.63, 42.11, 39.63, 25.10. APCI MS m/e 293 [(M+1)$^+$]. (data HCl salt) $^1$H NMR (400 MHz, DMSO-d$_6$) δ 9.78 (br s, NH), 8.1

(br s, NH), 7.73 (d, J=1.5 Hz,1H), 7.66 (dd, J=8.0,1.5 Hz, 1H), 7.53 (d, J=8.0 Hz, 1H), 3.39–3.01 (10H), 2.21 (m, 1H), 2.04 (d, J=11.0 Hz, 1H), 1.66 (m, 4H). GCMS m/e 292 (M$^+$). Anal. Calcd. For $C_{13}H_{18}N_2O_2HCl.1/2$methanol: C, 54.07; H, 6.47; N, 8.51. Found C, 53.98; H,6.72; N, 8.12

EXAMPLE 41

5,13-DIAZATETRACYCLO[9.3.1.0$^{2,10}$.0$^{4,8}$]-PENTADECA-2,4(8),9-TRIEN-6-ONE HYDROCHLORIDE (The title compound was prepared following the procedures described in Quallich, G. J.; Morrissey, P. M. *Synthesis* 1993, 51–53, treating 4,5-dinitro-10-aza-tricyclo[6.3.1.0$^{2,7}$] dodeca-2(7),3,5-triene-10-carboxylic acid tert-butyl ester as an equivalent to an ortho fluoro phenyl moiety.) $^1$H NMR (400 MHz, DMSO-d$_6$) δ 10.42 (s, NH), 9.88 (br s, NH), 7.52 (br s, 1H), 7.15 (s, 1H), 6.79 (s, 1H), 3.41 (d, J=5.0 Hz, 2H), 3.35–3.13 (m, 4H), 2.93 (m, 2H), 2.12 (m, 1H), 1.95 (d, J=11.5 Hz, 1H). APCI MS m/e 215.2 [(M+1)$^+$].

EXAMPLE 42

6-OXO-5-OXA-7,13-DIAZATETRACYCLO [9.3.1.0$^{2,10}$.0$^{4,9}$]-PENTADECA-2(10),3,8-TRIENE HYDROCHLORIDE (For references, see: Nachman, R. J. *J. Het. Chem.* 1982, 1545.) 2,2,2-Trifluoro-1-(4-hydroxy-5-amino-10-aza-tricyclo[6.3.1.0$^{2,7}$]dodeca-2(7),3,5-trien-10-yl)-ethanone (317 mg, 1.11 mmol) was stirred in THF (10 mL), treated with carbonyldiimidazole (269 mg, 1.66 mmol) and warmed to 60° C. for 18 hours. The mixture was concentrated, diluted with CH$_2$Cl$_2$ (50 mL) and washed with 1N aqueous HCl solution (3×10 mL). The organic layer was dried through a cotton plug, concentrated and chromatographed on Silica gel (50% ethyl acetate/Hexanes) to provide an oil (130 mg). This material converted to the title compound by the methods described in Example 9C. $^1$H NMR (400 MHz, DMSO-d$_6$) δ 11.78 (s, NH), 9.56 (br s, NH), 7.63 (br s, NH), 7.24 (s, 1H), 7.07 (s, 1H), 3.26 (br s, 2H), 3.16 (br t, J=9.5 Hz, 1H), 2.93 (br s, 1H), 2.18 (m, 1H), 1.97 (d, J=11.0 Hz, 1H). APCI MS m/e 217.2 [(M+1)$^+$].

EXAMPLE 43

6-BENZYL-5-OXA-7,13-DIAZATETRACYCLO [9.3.1.0$^{2,10}$.0$^{4,8}$]-PENTADECA-2(10),3,6,8-TETRAENE HYDROCHLORIDE 2,2,2-Trifluoro-1-(4-hydroxy-5-amino-10-aza-tricyclo [6.3.1.0$^{2,7}$]dodeca-2(7),3,5-trien-10-yl)-ethanone and phenyl-acetyl chloride were converted to the title compound following the procedures described in Example 47. $^1$H NMR (400 MHz, CD$_3$OD) δ 7.63 (s, 1H), 7.58 (s, 1H), 7.36–7.24 (5H), 4.29 (s, 2H), 3.46 (d, J=2.5 Hz, 2H), 3.39 (d, J=12.0 Hz, 2H), 3.18 (2H), 2.42 (m, 1H), 2.15 (d, J=11.5 Hz, 1H). APCI MS m/e 291.2 [(M+1)$^+$].

EXAMPLE 44

3-PHENYL-10-AZA-TRICYCLO[6.3.1.0$^{2,7}$] DODECA-2(7),3,5-TRIENE HYDROCHLORIDE

A) 5-Fluoro-1,4-dihydro-1,4-methano-naphthalene and 5-iodo-1,4-dihydro-1,4-methano-naphthalene (Eisch, J. J.; Burlinson, N. E. *J. Amer. Chem. Soc.* 1976, 98, 753–761. Paquette, L. A.; Cottrell, D. M.; Snow, R. A. *J. Amer. Chem. Soc.* 1977, 99, 3723–3733.)

Magnesium turnings (9.37 g, 385 mmol) were stirred in anhydrous THF (1000 mL) in a flame dried 2L 3 neck round bottom flask equipped with a non-equalizing addition funnel with a N$_2$ flow adapter, magnetic stirrer and efficient condenser equipped with a N$_2$ flow adapter. The flask was stirred and warmed to reflux by a removable heating mantle. 2,6-Difluoro-iodobenzene (0.3 g) was added followed by of 3N EtMgBr in THF (0.3 mL). The addition funnel was charged with an intimate mixture of cyclopentadiene (24.24 g, 367 mmol) and 2,6-difluoro-iodobenzene (88.0 g, 367 mmol). Small portions (~1 mL) of the intimate mixture were introduced to assist initiation (~4 times). After ~15 minutes, the reaction initiated (exotherm, and vapor condensation) and heating was maintained as necessary during the addition of the contents of the addition funnel. The reaction was then maintained at reflux for ~1 hour (no SM by GCMS).

The reaction was cooled to room temperature and quenched with H$_2$O (200 mL) followed by aqueous 1N HCl solution (200 mL) to dissolve the solids. Product was extracted with hexanes (4×150 mL). The combined organic layer was washed with saturated aqueous NaHCO$_3$ solution (150 mL), dried (Na$_2$SO$_4$), filtered through a Silica plug with hexanes rinse and concentrated to an oil (70 g). Chromatography on Silica gel eluting with hexanes provided two lots (9.0 and 21.0 g), which contained primarily 5-iodo-1,4-dihydro-1,4-methano-naphthalene. (TLC hexanes R$_f$ 0.63).

B) 5-Iodo-1,2,3,4-tetrahydro-1,4-methano-naphthalene-2,3-diol

5-Iodo-1,4-dihydro-1,4-methano-naphthalene (20 g) and N-methyl morpholine N-oxide (17.61 g, 130 mmol) were stirred in acetone (90 mL) and H$_2$O (13 mL). To this was added a solution of OsO$_4$ (0.2 mL, 2.5% wt. solution in t-butanol, 0.02 mmol). After 144 hours, Florisil (5 g) and saturated aqueous NaHSO$_3$ solution (3 mL) were added and stirred for ½ hour. The mixture was filtered through a Celite pad and the filtrate concentrated to produce an oil which was purified by chromatography on Silica gel eluting with a gradient of hexanes to 100% ethyl acetate to provide a yellow solid (13.73 g). APCI MS m/e 301.1 [(M–1)$^+$].

C) 10-Benzyl-3-iodo-10-aza-tricyclo[6.3.1.0$^{2,7}$] dodeca-2(7),3,5-triene

5-Iodo-1,2,3,4-tetrahydro-1,4-methano-naphthalene-2,3-diol (8.33 g, 27.6 mmol) and Et$_3$NBnCl (10 mg) were vigorously stirred in dichloroethane (25 mL) and H$_2$O (75 mL) then treated with sodium periodate (6.17 g, 29.0 mmol). After 1.5 hours, the layers were separated and the aqueous layer extracted with DCE (2×40 mL). The combined organic layer was washed with H$_2$O-(4×30 mL) until no reaction to starch iodide paper was observed, then with saturated aqueous NaCl solution (30 mL). The organic layer was dried through a cotton plug and treated with benzyl amine (3.16 mL, 29.0 mmol) and stirred for 2 minutes then transferred to an addition funnel. This solution was added over ~10 minutes to a vigorously stirred cooled (0° C.) mixture of NaHB(OAc)$_3$ (18.72 g, 88.0 mmol) in DCE (150 mL). After addition was complete, the mixture was stirred without cooling for 2 hours. The mixture was quenched with saturated aqueous Na$_2$CO$_3$ solution (100 mL) and stirred for 1 hour, then the layers were separated and the aqueous layer was extracted with CH$_2$Cl$_2$ (3×50 mL). The combined organic layer was washed with saturated aqueous NaCl solution (50 mL), dried through a cotton plug and concentrated. Chromatography on Silica gel provided an oil (6.3 g, 61%). (TLC 5% ethyl acetate/hexanes R$_f$ 0.10). $^1$H NMR (400 MHz, CDCl$_3$) δ 7.61 (d, J=8.0 Hz, 1H), 7.28–7.22 (m, 3H), 7.13 (d, J=8.0 Hz,1H), 6.98–6.94 (m, 3H), 3.58 (AB dd, J=14.2 Hz, 2H), 3.26 (br s, 1H), 3.21 (br s, 1H), 3.04 (br d, J=10.2 Hz, 1H), 2.83 (br d, J=10.2 Hz, 1H), 2.47 (d, J=10.0 Hz, 1H), 2.39 (d, J=10.0 Hz, 1H), 2.34 (m, 1H), 1.72 (d, J=10.5 Hz, 1H). APCI MS m/e 376.0 [(M+1)$^+$].

D) 10-Benzyl-3-phenyl-10-aza-tricyclo[6.3.1.0$^{2,7}$] dodeca-2(7),3,5-triene (For a discussion, see: Miyaura, N.; Suzuki, A. *Chem. Rev.* 1995, 95, 2457–2483.) 10-Benzyl-3-iodo-10-aza-tricyclo[6.3.1.0$^{2,7}$]dodeca-2(7),3,5-triene (375.3 mg, 1.0 mmol), potassium acetate (785 mg, 8.0 mmol) and phenyl boronic acid (183 mg, 1.5 mmol) were combined in 10/1 ethanol/H$_2$O (5 mL). The mixture was degassed (3 vacuum/N$_2$ cycles), treated with tetrakis(triphenylphosphine)palladium (0) (57.5 mg, 0.05 mmol) and warmed to 90° C. for 18 h. The reaction was cooled, diluted with H$_2$O and extracted with Et$_2$O (3×50 mL). The organic layer was washed with brine (50 mL), dried (MgSO$_4$), filtered and concentrated to provide an oil (180 mg, 55%). (TLC 4% ethyl acetate/hexanes R$_f$ 0.18). GCMS m/e 325 (M)$^+$.

E) 3-Phenyl-10-aza-tricyclo[6.3.1.0$^{2,7}$]dodeca-2(7), 3,5-triene hydrochloride 10-Benzyl-3-phenyl-10-aza-tricyclo[6.3.1.0$^{2,7}$]dodeca-2(7),3,5-triene was converted into the title compound utilizing the conditions described in Example 2D. (TLC 10% methanol/CH$_2$Cl$_2$ (NH$_3$) R$_f$ 0.30). (data for free base) $^1$H NMR (400 MHz, CDCl$_3$) δ 7.46–7.15 (8H), 3.17 (br s, 1H), 3.01 (m, 2H), 2.93 (d, J=13.0 Hz, 1H), 2.72 (dd, J=10.5,2.5 Hz, 1H), 2.63 (dd, J=10.5,2.5 Hz, 1H), 2.41 (m, 1H), 1.91 (d, J=10.5 Hz, 1H). APCI MS m/e 236.2 [(M+1)$^+$]. (HCl salt) M.p. 262–265° C. Anal. Calcd. for C$_{17}$H$_{17}$N.HCl.1/3H$_2$O: C, 73.26; H, 6.86; N, 5.19. Found C, 73.50; H, 6.77; N, 5.04.

EXAMPLE 45

3-HYDROXY-10-AZA-TRICYCLO[6.3.1.0$^{2,7}$] DODECA-2(7),3,5-TRIENE HYDROCHLORIDE

A) 10-Benzyl-3-boronic acid-10-aza-tricyclo [6.3.1.0$^{2,7}$]dodeca-2(7),3,5-triene 10-Benzyl-3-iodo-10-aza-tricyclo[6.3.1.0$^{2,7}$]dodeca-2(7),3,5-triene (3.0 g, 7.99 mmol) was stirred in anhydrous THF (40 mL) at −78° C. under nitrogen and treated dropwise with n-BuLi (3.84 mL of 2.5M solution in hexanes, 9.59 mmol). After 10 minutes, tri-isopropylborate (4.61 mL, 20.0 mmol) was added dropwise. After ~½ hour, the reaction was poured into saturated aqueous NaHCO$_3$ solution, stirred 5 minutes and extracted with ethyl acetate (3×50 mL) and concentrated. The residue was dissolved in 30% Et$_2$O/hexanes and extracted with 1N NaOH aqueous solution (4×50 mL). The combined aqueous basic layer was treated with concentrated HCl to achieve pH 8 and extracted with ethyl acetate (4×25 mL), dried (Na$_2$SO$_4$) and stripped. Chromatography on Silica gel eluting first with 3% ethyl acetate/hexanes to remove non-polar components, then with 5% methanol/CH$_2$Cl$_2$ provides the title compound. (TLC 25% ethyl acetate/hexanes R$_f$ 0.60).

B) 10-Benzyl-3-hydroxy-10-aza-tricyclo[6.3.1.0$^{2,7}$] dodeca-2(7),3,5-triene

10-Benzyl-3-boronic acid-10-aza-tricyclo[6.3.1.0$^{2,7}$] dodeca-2(7),3,5-triene (140 mg, 0.48 mmol) dissolved in THF (5 mL) was treated with N-methylmorpholine-N-oxide (64.5 mg, 0.48 mmol) and brought to reflux for 1 hour. The reaction was concentrated and chromatographed on Silica gel to provide product. (TLC 25% ethyl acetate/hexanes R$_f$ 0.18). $^1$H NMR (400 MHz, CDCl$_3$) δ 7.18–7.15 (3H), 7.04 (dd, J=8.0,7.0 Hz, 1H), 6.95 (m, 2H), 6.75 (d, J=7.0 Hz, 1H), 6.59 (dd, J=8.0,1.0 Hz, 1H), 3.53 (br s, OH), 3.51 (AB d, J=14.0 Hz, 2H), 3.28 (br s, 1H), 3.06 (br s, 1H), 2.91 (dd, J=8.5,1.5 Hz, 1H), 2.79 (ddd, J=8.5,1.5,1.5 Hz, 1H), 2.42 (d, J=11.0 Hz, 1H), 2.39 (d, J=11.0 Hz, 1H), 2.23 (m, 1H), 1.65 (d, J=10.5 Hz, 1H). APCI MS m/e 266.5 [(M+1)$^+$].

C) 3-Hydroxy-10-aza-tricyclo[6.3.1.0$^{2,7}$]dodeca-2 (7),3,5-triene hydrochloride 10-Benzyl-3-hydroxy-10-aza-tricyclo[6.3.1.0$^{2,7}$]dodeca-2(7),3,5-triene (160 mg, 0.60 mmol) was converted into the title compound by the methods described in Example 1D. $^1$H NMR (400 MHz, CDCl$_3$) δ 7.15 (dd, J=8.0,7.5 Hz, 1H), 6.84 (d, J=7.5 Hz, 1H), 6.76 (d, J=8.0 Hz, 1H), 3.51 (br s, 1H), 3.33–3.25 (3H), 3.16 (d, J=12.0 Hz, 1H), 3.09 (d, J=12.0 Hz, 1H), 2.29 (m, 1H), 2.02 (d, J=11.0 Hz, 1H). APCI MS m/e 175.8 [(M+1)$^+$]. (HCl salt) M.p. 253–255° C.

EXAMPLE 46

4,5-DIFLUORO-10-AZA-TRICYCLO[6.3.1.0$^{2,7}$] DODECA-2(7),3,5-TRIENE HYDROCHLORIDE

The title compound was prepared by the methods described in Examples 1 and 2 starting with 2,4,5-trifluorobromobenzene. $^1$H NMR (400 MHz, CDCl$_3$) δ 7.31 (t, J=8.5 Hz, 2H), 3.48–3.13 (6H), 2.38 (m, 1H), 2.11 (d, J=11.5 Hz, 1H). APCI MS m/e 196.2 [(M+1)$^+$]. (HCl salt) M.p. 301–303° C. Anal. Calcd. for C$_{11}$H$_{11}$F$_2$N.HCl.1/6H$_2$O: C, 56.30; H, 5.30; N, 5.97. Found C, 56.66; H, 5.41; N, 5.96.

EXAMPLE 47

6-ETHYL-5-OXA-7,13-DIAZATETRACYCLO [9.3.1.0$^{2,10}$.0$^{4,8}$]-PENTADECA-2(10),3,6,8-TETRAENE HYDROCHLORIDE 2,2,2-Trifluoro-1-(4-hydroxy-5-amino-10-aza-tricyclo [6.3.1.0$^{2,7}$]dodeca-2(7),3,5-trien-10-yl)-ethanone and propionyl chloride were converted to the title compound following the procedures described in Example 30 and Goldstein, S. W.; Dambek, P. J. *J. Het. Chem.* 1990, 27, 335. $^1$H NMR (400 MHz, CD$_3$OD) δ 7.64 (s, 1H), 7.62 (s, 1H), 3.48 (d, J=2.5 Hz, 2H), 3.41 (d, J=12.0 Hz, 2H), 3.20 (2H), 3.01 (q, J=7.5 Hz, 2H), 2.45 (m, 1H), 2.17 (d, J=11.5 Hz, 1H), 1.42 (t, J=7.5 Hz, 3H). APCI MS m/e 229.2 [(M+1)$^+$].

EXAMPLE 48

6-ISOPROPYL-5-OXA-7,13-DIAZATETRACYCLO[9.3.1.0$^{2,10}$.0$^{4,8}$]-PENTADECA-2(10),3,6,8-TETRAENE HYDROCHLORIDE 2,2,2-Trifluoro-1-(4-hydroxy-5-amino-10-aza-tricyclo[6.3.1.0$^{2,7}$]dodeca-2(7),3,5-trien-10-yl)-ethanone and isobutyryl chloride were converted to the title compound following the procedures described in Example 47. (TLC 25% ethyl acetate/hexanes R$_f$ 0.14). $^1$H NMR (400 MHz, CD$_3$OD) δ 7.65 (2H), 3.49 (br s, 2H), 3.41 (d, J=12.0 Hz, 2H), 3.33–3.19 (3H), 2.45 (m, 1H), 2.18 (d, J=11.5 Hz, 1H), 1.45 (d, J=7.0 Hz, 6H). APCI MS m/e 243.2 [(M+1)$^+$]. (HCl salt) M.p. 249–251° C.

EXAMPLE 49

5,14-DIAZATETRACYCLO[10.3.1.0$^{2,11}$.0$^{4,9}$]HEXADECA-2(11),3,5,7,9-PENTAENE HYDROCHLORIDE

A) 1-(5,14-Diazatetracyclo[10.3.1.0$^{2,11}$.0$^{4,9}$]hexadeca-2(11),3,5,7,9-pentaen-10-yl)-2,2,2-trifluoro-ethanone (Based on the method of Campbell, K. N.; Schaffner, I. J. *J. Am. Chem. Soc.* 1945, 67, 86.)

1-(4-Amino-10-aza-tricyclo[6.3.1.0$^{2,7}$]dodeca-2(7),3,5-trien-10-yl)-2,2,2-trifluoro-ethanone (607 mg, 1.98 mmol) was dissolved in 95% ethanol/H$_2$O (5 mL) and treated with FeCl$_3$.6H$_2$O (800 mg, 2.97 mmol), ZnCl$_2$ (27 mg, 0.20 mmol) in ethanol (2 mL). The mixture was warmed to 65° C. for 15 min., treated with acrolein (0.2 mL, 2.97 mmol) and warmed to reflux for 2.5 hours. The mixture was judged complete by TLC, cooled and quenched into saturated aqueous NaHCO$_3$ solution (40 mL). The mixture (pH 8.5) was extracted with CH$_2$Cl$_2$ (8×30 mL). The organic layer was washed with H$_2$O and saturated aqueous NaCl solution then dried through a cotton plug. Concentration afforded a dark oil which was chromatographed on Silica gel to provide a yellow oil (105 mg, 17%). (TLC 50% ethyl acetate/hexanes R$_f$ 0.08).

B) 5,14-Diazatetracyclo[10.3.1.0$^{2,11}$.0$^{4,9}$]hexadeca-2(11),3,5,7,9-pentaene hydrochloride 1-(5,14-Diazatetracyclo[10.3.1.0$^{2,11}$.0$^{4,9}$]hexadeca-2(11),3,5,7,9-pentaen-10-yl)-2,2,2-trifluoro-ethanone (94.7 mg, 0.31 mmol) was converted to the title compound using methods described in Example 7 to provide a crystalline solid (36.9 mg). $^1$H NMR (400 MHz, CD$_3$OD) δ 9.19 (m, 2H), 8.33 (s, 1H), 8.27 (s, 1H), 8.10 (dd, J=8.3, 5.6 Hz, 1H), 3.78 (br s, 1H), 3.74 (br s, 1H), 3.58 (br d, J=11.4 Hz, 2H), 3.40 (M, 2H), 2.50 (m, 1H), 2.34 (d, J=11.6 Hz, 1H). APCI MS m/e 210.9 [(M+1)$^+$]; M.p. 260° C. (dec.); Anal. Calcd. for C$_{14}$H$_{14}$N$_2$.2HCl: C, 59.38; H, 5.69; N, 9.89. Found C, 59.69; H, 5.82; N, 9.79.

EXAMPLE 50

6-METHYL-5,14-DIAZATETRACYCLO[10.3.1.0$^{2,11}$.0$^{4,9}$]HEXADECA-2(11),3,5,7,9-PENTAENE HYDROCHLORIDE

A) 1-((6-Methyl-5,14-diazatetracyclo[10.3.1.0$^{2,11}$.0$^{4,9}$]hexadeca-2(11),3,5,7,9-pentaen-10-yl)-2,2,2-trifluoro-ethanone Following the method described in Example 49A, 1-(4-Amino-10-aza-tricyclo[6.3.1.0$^{2,7}$]dodeca-2(7),3,5-trien-10-yl)-2,2,2-trifluoro-ethanone (686 mg, 2.00 mmol) was reacted with (E)-2-butenal (0.2 mL, 2.97 mmol) to provide a yellow oil. (335.6 mg, 52%). (TLC 75% ethyl acetate/hexanes R$_f$ 0.25).

B) 6-Methyl-5,14-diazatetracyclo[10.3.1.0$^{2,11}$.0$^{4,9}$]hexadeca-2(11),3,5,7,9-pentaene hydrochloride 1-(6-Methyl-5,14-diazatetracyclo[10.3.1.0$^{2,11}$.0$^{4,9}$]hexadeca-2(11),3,5,7,9-pentaen-10-yl)-2,2,2-trifluoro-ethanone (308 mg, 0.96 mmol) was converted to the title compound using methods described in Example 7 to provide a crystalline solid (186 mg). $^1$H NMR (400 MHz, CD$_3$OD) δ 9.00 (d, J=8.5 Hz, 1H), 8.25 (s, 1H), 8.17 (s, 1H), 7.94 (d, J=8.5 Hz, 1H), 3.76 (br s, 1H), 3.71 (br s, 1H), 3.57 (br d, J=11.8 Hz, 2H), 3.38 (M, 2H), 3.01 (s, 3H), 2.49 (m, 1H), 2.32 (d, J=11.6 Hz, 1H). APCI MS m/e 225.2 [(M+1)$^+$]; M.p.>300° C. (dec.); Anal. Calcd. for C$_{15}$H$_{16}$N$_2$.2HCl.1/2H$_2$O: C, 58.83; H, 6.25; N, 9.15. Found C, 58.49; H, 6.22; N, 9.02.

EXAMPLE 51

7-METHYL-5,14-DIAZATETRACYCLO[10.3.1.0$^{2,11}$.0$^{4,9}$]HEXADECA-2(11),3,5,7,9-PENTAENE HYDROCHLORIDE

A) 1-(7-Methyl-5,14-diazatetracyclo[10.3.1.0$^{2,11}$.0$^{4,9}$]hexadeca-2(11),3,5,7,9-pentaen-10-yl)-2,2,2-trifluoro-ethanone Following the method described in Example 49A, 1-(4-Amino-10-aza-tricyclo[6.3.1.0$^{2,7}$]dodeca-2(7),3,5-trien-10-yl)-2,2,2-trifluoro-ethanone (686 mg, 2.00 mmol) was reacted with 2-methylpropenal (0.25 mL, 3.00 mmol) to provide a yellow oil (94 mg, 15%). (TLC 10% methanol/CH$_2$Cl$_2$ R$_f$ 0.16).

B) 7-Methyl-5,14-diazatetracyclo[10.3.1.0$^{2,11}$.0$^{4,9}$]hexadeca-2(11),3,5,7,9-pentaene hydrochloride 1-(7-Methyl-5,14-diazatetracyclo[10.3.1.0$^{2,11}$.0$^{4,9}$]hexadeca-2(11),3,5,7,9-pentaen-10-yl)-2,2,2-trifluoro-ethanone (86 mg, 0.27 mmol) was converted to the title compound using methods described in Example 7 to provide a crystalline solid (12.6 mg). $^1$H NMR (400 MHz, CD$_3$OD) δ 9.10 (s, 1H), 9.00 (s, 1H), 8.22 (s, 1H), 8.20 (s, 1H), 3.76 (br s, 1H), 3.72 (br s, 1H), 3.57 (br d, J=11.5 Hz, 2H), 3.39 (M, 2H), 2.71 (s, 3H), 2.48 (m, 1H), 2.32 (d, J=11.6 Hz, 1H). APCI MS m/e 225.0 [(M+1)$^+$].

EXAMPLE 52

7-ETHYL-5,14-DIAZATETRACYCLO[10.3.1.0$^{2,11}$.0$^{4,9}$]HEXADECA-2(11),3,5,7,9-PENTAENE HYDROCHLORIDE

A) 1-(7-Ethyl-5,14-diazatetracyclo[10.3.1.0$^{2,11}$.0$^{4,9}$]hexadeca-2(11),3,5,7,9-pentaen-10-yl)-2,2,2-trifluoro-ethanone Following the method described in Example 49A, 1-(4-Amino-10-aza-tricyclo[6.3.1.0$^{2,7}$]dodeca-2(7),3,5-trien-10-yl)-2,2,2-trifluoro-ethanone (686 mg, 2.00 mmol) was reacted with 2-ethylpropenal (0.35 mL, 3.60 mmol) to provide a yellow oil (110 mg, 16%). (TLC 75% ethyl acetate/hexanes R$_f$ 0.32).

B) 7-Ethyl-5,14-diazatetracyclo[10.3.1.0$^{2,11}$.0$^{4,9}$]hexadeca-2(11),3,5,7,9-pentaene hydrochloride 1-(7-Ethyl-5,14-diazatetracyclo[10.3.1.0$^{2,11}$.0$^{4,9}$]hexadeca-2(11),3,5,7,9-pentaen-10-yl)-2,2,2-trifluoro-ethanone (94 mg, 0.28 mmol) was converted to the title compound using methods described in Example 7 to provide a crystalline solid (33 mg). $^1$H NMR (400 MHz, CD$_3$OD) δ 9.12 (s, 1H), 9.00 (s, 1H), 8.23 (s, 1H), 8.18 (s, 1H), 3.76 (br s, 1H), 3.72 (br s, 1H), 3.56 (br d, J=11.5 Hz, 2H), 3.37 (M, 2H), 3.05 (q, J=7.5 Hz, 2H), 2.48 (m, 1H), 2.32 (d, J=11.6 Hz, 1H), 1.44 (t, J=7.5 Hz, 3H). APCI MS m/e 239.1 [(M+1)$^+$]; M.p. 288–291° C. (dec.); Anal. Calcd. for C$_{16}$H$_{18}$N$_2$.2HCl.H$_2$O: C, 58.36; H, 6.73; N, 8.51. Found C, 57.98; H, 5.99; N, 8.41.

EXAMPLE 53

8-METHYL-5,14-DIAZATETRACYCLO[10.3.1.0$^{2,11}$.0$^{4,9}$]HEXADECA-2(11),3,5,7,9-PENTAENE HYDROCHLORIDE

A) 1-(8-Methyl-5,14-diazatetracyclo[10.3.1.0$^{2,11}$.0$^{4,9}$]hexadeca-2(11),3,5,7,9-pentaen-10-yl)-2,2,2-trifluoro-ethanone Following the method described in Example 49A, 1-(4-Amino-10-aza-tricyclo[6.3.1.0$^{2,7}$]dodeca-2(7),3,5-trien-10-yl)-2,2,2-trifluoro-ethanone (775 mg, 2.52 mmol) was reacted with 1-buten-3-one (0.32 mL, 3.79 mmol) to provide a yellow oil. (424 mg, 52%). (TLC 50% ethyl acetate/hexanes R$_f$ 0.08).

B) 8-Methyl-5,14-diazatetracyclo[10.3.1.0$^{2,11}$.0$^{4,9}$]hexadeca-2(11),3,5,7,9-pentaene hydrochloride 1-(8-Methyl-5,14-diazatetracyclo[10.3.1.0$^{2,11}$.0$^{4,9}$]hexadeca-2(11),3,5,7,9-pentaen-10-yl)-2,2,2-trifluoro-ethanone (403 mg, 1.26 mmol) was converted to the title compound using methods described in Example 7 to provide a crystalline solid (266 mg). $^1$H NMR (400 MHz, CD$_3$OD) δ 9.01 (d, J=5.6 Hz, 1H), 8.49 (s, 1H), 8.22 (s, 1H), 7.97 (d, J=5.6 Hz, 1H), 3.76 (br m, 2H), 3.58 (br d, J=11.5 Hz, 2H), 3.40 (m, 2H), 3.06 (s, 3H), 2.48 (m, 1H), 2.33 (d, J=11.6 Hz, 1H). Anal. Calcd. for C$_{15}$H$_{16}$N$_2$.2HCl.H$_2$O: C, 57.15; H, 6.39; N, 8.89. Found C, 57.43; H, 6.44; N, 8.82.

EXAMPLE 54

5,14-DIAZATETRACYCLO[10.3.1.0$^{2,11}$.0$^{4,9}$]HEXADECA-2(11),3,7,9-TETRAEN-6-ONE HYDROCHLORIDE

A) 3,3-Dimethoxypropanoic acid lithium salt (Related to methods described in Alabaster, C. T. et. al., J. Med. Chem. 1988, 31, 2048–2056.) 3,3-Dimethoxypropanoic acid methyl ester (14.25 g, 96.2 mmol) in THF (100 mL) was treated with LiOH.H$_2$O (2.5 g, 106 mmol) and H$_2$O (2 mL). The mixture was brought to reflux for 4 hours, cooled to room temperature and azeotropically dried from THF (4 times) to provide white solids (13.3 g).

B) 1-(4-(N-3',3'-Dimethoxy-propionamide)-10-aza-tricyclo[6.3.1.0$^{2,7}$]dodeca-2(7),3,5-trien-10-yl)-2,2,2-trifluoro-ethanone 3,3-Dimethoxypropanoic acid lithium salt (840 mg, 6.0 mmol) in THF (15 mL) was treated with trifluoroacetic anhydride (0.85 mL, 6.0 mmol) dropwise and stirred for 15 minutes. The resulting yellow solution was added dropwise to a vigorously stirred mixture of 1-(4-amino-10-aza-tricyclo[6.3.1.0$^{2,7}$]dodeca-2(7),3,5-trien-10-yl)-2,2,2-trifluoro-ethanone (540 mg, 2 mmol) in THF (5 mL) and saturated aqueous NaHCO$_3$ solution (2 mL). After 3 hours the reaction mixture was diluted with H$_2$O and extracted with ethyl acetate (3 times). The organic layer was washed with brine, dried over Na$_2$SO$_4$, filtered and concentrated to an oil which was purified by chromatography on Silica gel to provide a white solid (477 mg, 62%). (TLC 50% ethyl acetate/hexanes R$_f$ 0.37).

C) 1-(5,14-Diazatetracyclo[10.3.1.0$^{2,11}$.0$^{4,9}$]hexadeca-2(11),3,7,9-tetraen-6-one-10-yl)-2,2,2-trifluoro-ethanone 1-(4-(N-3',3'-Dimethoxy-propionamide)-10-aza-tricyclo[6.3.1.0$^{2,7}$]dodeca-2(7),3,5-trien-10-yl)-2,2,2-trifluoro-ethanone (460 mg, 1.19 mmol) was treated with trifluoroacetic acid (4 mL) and stirred 18 hours, concentrated, diluted with CH$_2$Cl$_2$ and H$_2$O. The aqueous layer was extracted with CH$_2$Cl$_2$ (4 times) and the organic layer was washed with saturated aqueous NaHCO$_3$ solution (40 mL) and saturated aqueous NaCl solution then dried through a cotton plug. Concentration afforded a yellow solid (320 mg, 83%).

D) 5,14-Diazatetracyclo[10.3.1.0$^{2,11}$.0$^{4,9}$]hexadeca-2(11),3,7,9-tetraen-6-one hydrochloride 1-(5,14-Diazatetracyclo[10.3.1.0$^{2,11}$.0$^{4,9}$]hexadeca-2(11),3,7,9-tetraen-6-one-10-yl)-2,2,2-trifluoro-ethanone (540 mg, 2 mmol) was converted to the title compound using methods described in Example 7 to provide the title compound a pink crystalline solid (72 mg, 71%). $^1$H NMR (400 MHz, CD$_3$OD) δ 8.42 (d, J=8.8 Hz, 1H), 7.90 (s, 1H), 7.66 (s, 1H), 6.98 (d, J=8.8 Hz, 1H), 3.59 (br s, 1H), 3.56 (br s, 1H), 3.49 (dd, J=12.4, 5.8 Hz, 2H), 3.29 (m, 2H), 2.42 (m, 1H), 2.23 (d, J=11.6 Hz, 1H). APCI MS m/e 227 [(M+1)$^+$]; M.p. 300° C. (dec.); Anal. Calcd. for C$_{14}$H$_{14}$N$_2$O.2HCl: C, 56.20; H, 5.39; N, 9.36. Found C, 56.40; H, 5.63; N, 9.25.

EXAMPLE 55

6-CHLORO-5,14-DIAZATETRACYCLO [10.3.1.0$^{2,11}$.0$^{4,9}$]HEXADECA-2(11),3,5,7,9-PENTAENE HYDROCHLORIDE

A) 1-(6-Chloro-5,14-diazatetracyclo [10.3.1.0$^{2,11}$.0$^{4,9}$]hexadeca-2(11),3,5,7,9-pentaen-10-yl)-2,2,2-trifluoro-ethanone 1-(5,14-diazatetracyclo[10.3.1.0$^{2,11}$.0$^{4,9}$]hexadeca-2(11),3,7,9-tetraen-6-one-10-yl)-2,2,2-trifluoro-ethanone (156 mg, 0.49 mmol) was treated with POCl$_3$ (5 mL) and warmed to 100° C. with stirring for 3 hours. After concentration in vacuo, the residue was diluted with CH$_2$Cl$_2$ (15 mL) and carefully treated with saturated NaHCO$_3$ solution (10 mL) with stirring. Once CO$_2$ evolution slowed the mixture was separated and the aqueous layer extracted CH$_2$Cl$_2$ (3 times). The organic layer was washed with H$_2$O and saturated NaCl solution, filtered through cotton and concentrated to a brown oil (217 mg, 93%). (TLC ethyl acetate, R$_f$ 0.3) $^1$H NMR (400 MHz, $^2$HCCl$_3$) δ 8.03 (d, J=8.5 Hz, 1H), 7.83 (s, 1H), 7.62 (s, 1H), 7.35 (d, J=8.5 Hz, 1H), 4.43 (m, 1H), 4.01 (m, 1H), 3.62 (m, 1H), 3.29 (m, 2H), 3.23 (m, 1H), 2.45 (m, 1H), 2.10 (d, J=11.6 Hz, 1H). APCI MS m/e 341.1 [(M+1)$^+$].

B) 6-Chloro-5,14-diazatetracyclo[10.3.1.0$^{2,11}$.0$^{4,9}$] hexadeca-2(11),3,5,7,9-pentaene hydrochloride 1-(6-Chloro-5,14-diazatetracyclo[10.3.1.0$^{2,11}$.0$^{4,9}$]hexadeca-2(11),3,5,7,9-pentaen-10-yl)-2,2,2-trifluoro-ethanone (26 mg, 0.076 mmol) was converted to the title compound using methods described in Example 7 to provide the title compound a solid (5.8 mg, 24%). $^1$H NMR (free base, 400 MHz, 2HCCl$_3$) δ 8.01 (d, J=8.5 Hz, 1H), 7.77 (s, 1H), 7.57 (s, 1H), 7.30 (d, J=8.5 Hz, 1H), 3.28 (br s, 1H), 3.24 (br s, 1H), 3.12 (br d, J=12.5 Hz, 2H), 2.96 (br d, J=12.5 Hz, 2H), 2.41 (m, 1H), 2.02 (d, J=11.6 Hz, 1H). APCI MS m/e 245.1 [(M+1)$^+$].

EXAMPLE 56

6-METHOXY-5,14-DIAZATETRACYCLO 10.3.1.0$^{2,11}$.0$^{4,9}$]HEXADECA-2(11),3,5,7,9-PENTAENE HYDROCHLORIDE

A) 6-Chloro-5,14-diazatetracyclo[10.3.1.0$^{2,11}$.0$^{4,9}$] hexadeca-2(11),3,5,7,9-pentaen-10-carboxylic acid tert-butyl ester 6-Chloro-5,14-diazatetracyclo[10.3.1.0$^{2,11}$.0$^{4,9}$]hexadeca-2(11),3,5,7,9-pentaene (2.82 g, 11.53 mmol) was converted into the title compound as described in Example 12A to provide a brown oil (3.55 g, 89%). (TLC: 5% methanol/CH$_2$Cl$_2$, R$_f$ 0.37).

B) 6-Methoxy-5,14-diazatetracyclo[10.3.1.0$^{2,11}$.0$^{4,9}$] hexadeca-2(11),3,5,7,9-pentaen-10-carboxylic acid tert-butyl ester Sodium metal (~12 mg) was dissolved in methanol (1 mL) under nitrogen with stirring and treated with a solution of 6-chloro-5,14-diazatetracyclo[10.3.1.0$^{2,11}$.0$^{4,9}$]hexadeca-2(11),3,5,7,9-pentaen-10-carboxylic acid tert-butyl ester (118 mg, 0.33 mmol) in methanol (3 mL) and brought to reflux for 18 hours. The mixture was cooled, concentrated, treated with H$_2$O and extracted with CH$_2$Cl$_2$. The organic layer was washed with saturated NaCl solution and filtered through a cotton plug then concentrated to an oil (165 mg). (TLC: 5% methanol/CH$_2$Cl$_2$ R$_f$ 0.55).

C) 6-Methoxy-5,14-diazatetracyclo[10.3.1.0$^{2,11}$.0$^{4,9}$] hexadeca-2(11),3,5,7,9-pentaene hydrochloride 6-Methoxy-5,14-diazatetracyclo[10.3.1.0$^{2,11}$.0$^{4,9}$]hexadeca-2(11),3,5,7,9-pentaen-10-carboxylic acid tert-butyl ester (138 mg, 0.41 mmol) was dissolved in trifluoroacetic acid (4 mL) brought to reflux for 4 hours. The mixture was cooled and concentrated to an oil which was dissolved in ethyl acetate and treated with 3N HCl/ethyl acetate (1 mL). After concentration the residue was recrystallized from methanol/diethyl ether to provide a beige solid (51 mg, 26%). $^1$H NMR (400 MHz, CD$_3$OD) δ 8.77 (d, J=9.5 Hz, 1H), 8.01 (s, 1H), 7.90 (s, 1H), 7.54 (d, J=9.5 Hz, 1H), 4.30 (s, 3H), 3.65 (br s, 1H), 3.61 (br s, 1H), 3.50 (dd, J=12.4, 3.8 Hz, 2H), 3.29 (m, 2H), 2.44 (m, 1H), 2.24 (d, J=11.6 Hz, 1H). APCI MS m/e 241.2 [(M+1)$^+$]; M.p. 240, (darkens), 275° C. (dec.); (TLC: 10% methanol (NH$_3$)/CH$_2$Cl$_2$, R$_f$ 0.38).

EXAMPLE 57

6-CHLORO-10-FLUORO-5,14-DIAZATETRACYCLO[10.3.1.0$^{2,11}$.0$^{4,9}$]HEXADECA-2(11),3,5,7,9-PENTAENE HYDROCHLORIDE

A) 1-(6-Chloro-10-fluoro-5,14-diazatetracyclo [10.3.1.0$^{2,11}$.0$^{4,9}$]hexadeca-2(11),3,5,7,9-pentaen-10-yl)-2,2,2-trifluoro-ethanone 3-Fluoro-10-aza-tricyclo[6.3.1.0$^{2,7}$]-dodeca-2(7),3,5-triene was converted to 1-(3-Fluoro-10-aza-tricyclo [6.3.1.0$^{2,7}$]-dodeca-2(7),3,5-trien-10-yl)-2,2,2-trifluoroethanone by the methods described in Example 7A. This product was nitrated as described in Example 7B. The resulting mixture of nitrated products was reduced as described in Example 8, then converted to a chloroquinoline as described in Examples 54 and 55. These products were separated by column chromatography on silica gel to provide the title compound. (TLC: 50% ethyl acetate/hexanes, R$_f$ 0.50).

B) 6-Chloro-10-fluoro-5,14-diazatetracyclo [10.3.1.0$^{2,11}$.0$^{4,9}$]hexadeca-2(11),3,5,7,9-pentaene hydrochloride 1-(6-Chloro-10-fluoro-5,14-diazatetracyclo[10.3.1.0$^{2,11}$.0$^{4,9}$]hexadeca-2(11),3,5,7,9-pentaen-10-yl)-2,2,2-trifluoro-ethanone was converted to 6-chloro-10-fluoro-5,14-diazatetracyclo[10.3.1.0$^{2,11}$.0$^{4,9}$]hexadeca-2(11),3,5,7,9-pentaene by methods described in Example 7C. $^1$H NMR (400 MHz, CDCl$_3$) δ 8.03 (dd, J=8.5, 1.5 Hz, 1H), 7.36 (d, J=8.5 Hz, 1H), 7.24 (s, 1H), 3.52 (br s, 1H), 3.16 (br s, 1H), 3.11 (dd, J=12.8, 1.6 Hz, 2H), 2.97 (ddd, J=12.8, 2.5, 2.5 Hz, 1H), 2.85 (ddd, J=12.8, 2.5, 2.5 Hz, 1H), 2.46 (m, 1H), 2.06 (d, J=10.8 Hz, 1H). El MS m/e 263 [M$^+$]. This material was converted to the title compound as described in Example 7C.

EXAMPLE 58

5,8,14-TRIAZATETRACYCLO[10.3.1.0$^{2,11}$.0$^{4,9}$]HEXADECA-2(11),3,7,9-TETRAEN-6-ONE HYDROCHLORIDE

A) 1-(5,8,14-Triazatetracyclo[10.3.1.0$^{2,11}$.0$^{4,9}$]hexadeca-2(11),3,7,9-tetraen-6-on-10-yl)-2,2,2-trifluoro-ethanone 1-(4,5-Diamino-10-aza-tricyclo[6.3.1.0$^{2,7}$]dodeca-2(7),3,5-trien-10-yl)-2,2,2-trifluoro-ethanone (536 mg, 1.88 mmol) was stirred in ethanol (4 ml). This mixture was treated with methyl-2-hydroxyl-2-methoxy acetate (0.203 mL, 2.07 mmol) and stirred at 70° C. for 2.5 hours. The reaction was cooled to room temperature and concentrated. Trituration with methanol and filtration provided light yellow solids (337 mg, 55%). (TLC 10% methanol/CH$_2$Cl$_2$ R$_f$ 0.57).

B) 5,8,14-Triazatetracyclo[10.3.1.0$^{2,11}$.0$^{4,9}$]hexadeca-2(11),3,7,9-tetraen-6-one hydrochloride 1-(5,8,14-Triazatetracyclo[10.3.1.0 $^{2,11}$.0$^{4,9}$]hexadeca-2(11),3,7,9-tetraen-6-on-10-yl)-2,2,2-trifluoro-ethanone (145 mg, 0.45 mmol) was converted to the title compound by the methods described in Example 7C to provide a brown solid (26 mg, 46%). $^1$H NMR (400 MHz, D$_2$O) δ 7.94 (s, 1H), 7.58 (s, 1H), 7.18 (s, 1H), 3.39 (br s, 2H), 3.28 (br d, J=12.5 Hz, 1H), 3.12 (br d, J=12.5 Hz, 1H), 2.29 (m, 1H), 1.99 (d, J=12.0 Hz, 1H). APCI MS m/e 228.2 [(M+1)$^+$]; M.p. 296, (darkens), 310° C. (dec.); (TLC: 10% CH$_2$Cl$_2$/methanol (NH$_3$), R$_f$ 0.10).

EXAMPLE 59

10-AZA-TRICYCLO[6.3.1.0$^{2,7}$]DODECA-2(7),3,5-TRIENE TOSYLATE

A) 3-N-Benzyl-2,3,4,5-tetrahydro-1,5-methano-1H-3-benzazepine

A stream of ozone was bubbled through a solution of 4.00 g of benzonorbornadiene (1,4-dihydro-1,4-methanonaphthalene) (28.1 mmol, 1.0 equivalent) in 80 mL of methanol at −78° C. Once the solution developed a blue color, ozone generation was stopped after another few minutes and then oxygen was bubbled through for five minutes to dispel the blue color. Then the solution was purged with nitrogen for 20 to 40 minutes to deoxygenate the solution. To the cold solution was added 0.199 g of 5% platinum on carbon, 55% wet by weight, (0.0281 mmol, 0.001 equivalent). The system was passivated with hydrogen, pressurized to 40 psi of hydrogen, and gradually warmed to room temperature. Once the ozonide was reduced completely (within 45–60 minutes), an additional 0.798 g of 5% platinum on carbon (0.112 mmol, 0.004 equivalent) was added to the reaction mixture at 0° C., followed by 3.07 mL of benzylamine (28.1 mmol, 1.0 equivalent) and 0.561 mL of 96% formic acid (14.0 mmol, 0.50 equivalent). The system was repressurized to 50 psi of hydrogen and allowed to warm to room temperature. After 4 hours, the reaction mixture was removed from the reactor and filtered through a pad of Celite, washing with 20 mL of methanol. This reaction mixture was used in the next step (Example 59B), but isolation of the intermediate was carried out as follows: the filtrate was concentrated in vacuo and partitioned between 40 mL of methylene chloride and 30 mL of a saturated aqueous solution of sodium carbonate; the aqueous layer was extracted with another 30 mL of methylene chloride; the combined organic layers were dried over anhydrous sodium sulfate and concentrated; the residue was dissolved in 10 mL of 9:1 hexane/ethyl acetate and passed through a plug of silica gel; and after concentrating the filtrate, the title compound was obtained as an oil (3.34 g, 48%): $^1$H NMR (400 MHz, CD$_3$OD): δ 7.22–7.19 (m, 7H), 6.93 (d, J=8.0 Hz, 2H), 3.52 (s, 2H), 3.13–3.11 (m, 2H), 2.85 (d, J=9.5 Hz, 2H), 2.47 (d, J=9.5 Hz, 2H), 2.32–2.29 (m, 1H), 1.71 (d, J=10.0 Hz, 1H).

B) 2,3,4,5-Tetrahydro-1,5-methano-1H-3-benzazepine tosylate

A pressure reactor was charged with the crude 3-N-benzyl-2,3,4,5-tetrahydro-1,5-methano-1H-3-benzazepine (from Example 59A prior to workup) in 100 mL of methanol. To the reaction mixture was added 3.74 g of p-toluenesulfonic acid monohydrate (19.7 mmol, 0.7 equivalent) and 0.986 g of 20% palladium hydroxide on carbon, 50% wet by weight (0.703 mmol, 0.025 equivalent). The reactor was pressurized to 50 psi of hydrogen and heated to 40° C. After heating for 15 hours the reactor was cooled to room temperature. The reaction mixture was filtered through Celite, washing with methanol. The filtrate was concentrated in vacuo and stripped down from 20 mL of isopropanol. The residue was redissolved in 32 mL of isopropanol and heated to 70° C. To the hot solution was added 16 mL of hexane and the resulting solution was allowed to slowly cool with stirring. Crystals formed and were stirred at room temperature for 12 hours. The white crystals were filtered and dried to give 2.65 g (28%) of the tosylate salt of 2,3,4,5-tetrahydro-1,5-methano-1H-3-benzazepine tosylate; mp: 207–208° C.; $^1$H NMR (400 MHz, CD$_3$OD): δ 7.69 (d, J=7.9 Hz, 2H), 7.43–7.32 (m, 4H), 7.23 (d, J=7.9 Hz, 2H), 3.37 (d, J=11.2 Hz, 4H), 3.30 (bs, 2H), 3.15 (d, J=12.4 Hz, 2H), 2.36 (s, 3H), 2.40–2.35 (m, 1H), 2.08 (d, J=11.2 Hz, 1H); $^{13}$C NMR (100 MHz, CD$_3$OD): δ 140.8, 140.5, 139.1, 127.2, 127.2, 124.3, 122.3, 45.1, 39.7, 37.3, 18.7; IR (KBr, cm$^{-1}$): 3438, 3021, 2958, 2822, 2758, 2719, 2683, 2611, 2424, 1925, 1606, 1497, 1473, 1428, 1339, 1302, 1259, 1228, 1219, 1176, 1160, 1137, 1122, 1087, 1078, 945, 914, 876, 847, 829, 818, 801, 710, 492; Anal. Calcd for C$_{18}$H$_{21}$NO$_3$S: C, 65.23; H, 6.39; N, 4.23; Found: C, 65.05; H, 6.48; N, 4.26.

EXAMPLE 60

10-AZA-TRICYCLO[6.3.1.0$^{2,7}$]DODECA-2(7),3,5-TRIENE TOSYLATE

A) 3-Oxo-indan-1-carboxylic acid methyl ester

A solution of 10.0 g of 3-oxo-indan-1-carboxylic acid (56.8 mmol, 1.0 equivalent) and 0.25 mL of concentrated sulfuric acid in 20 mL of methanol was heated to a reflux for 4 hours. The reaction mixture was then cooled to room temperature and diluted with 100 mL of methyl-tert-butyl alcohol. The organic solution was washed twice with 60 mL of a saturated aqueous sodium bicarbonate solution, and once with 50 mL of a saturated aqueous sodium chloride solution. The organic layer was dried over anhydrous sodium sulfate and concentrated. The title compound crystallized as a white solid upon concentration, (10.4 g, 96%); mp: 46–47° C.; $^1$H NMR (400 MHz, CDCl$_3$): δ 7.74 (d, J=7.6 Hz, 1H), 7.68 (d, J=7.6 Hz, 1H), 7.62 (t, J=7.6 Hz, 1H), 7.44 (t, J=7.6 Hz, 1H), 4.29 (dd, J=8.0, 3.4 Hz, 1H), 3.76 (s, 3H), 3.13 (dd, J=19.1, 3.4 Hz, 1H), 2.86 (dd, J=19.1, 8.0 Hz, 1H); $^{13}$C NMR (100 MHz, CD$_3$OD): δ 204.4, 172.5, 151.3, 136.5, 135.2, 129.1, 126.7, 124.1, 52.9, 43.8, 39.7; IR (neat, cm$^{-1}$): 2954, 1710, 1602, 1462, 1435, 1403, 1319, 1241, 1206, 1168, 1092, 1044, 1014, 986, 881, 837, 760, 686, 580, 538.

B)
3-Cyano-3-trimethylsilanyloxy-indan-1-carboxylic acid methyl ester

To a solution of 3.80 g of 3-oxo-indan-1-carboxylic acid methyl ester (20.0 mmol, 1 equivalent) in 6 mL of toluene and 2 mL of acetonitrile was added 192 mg of zinc iodide (0.600 mmol, 0.03 equivalent) followed by 3.47 mL of trimethylsilyl cyanide (26.0 mmol, 1.3 equivalent). The reaction mixture was heated to 50° C. for 5 hours. The reaction mixture was then cooled to room temperature and diluted with 12 mL of toluene and 8 mL of a saturated aqueous sodium bicarbonate solution. After stirring the mixture for 1 hour the layers were separated. The organic layer was washed with another 8 mL of a saturated aqueous sodium bicarbonate solution followed by 8 mL of a saturated aqueous sodium chloride solution. The organic layer was dried over anhydrous sodium sulfate and concentrated in vacuo to give 3-cyano-3-trimethylsilanyloxy-indan-1-carboxylic acid methyl ester as an oil (5.61 g, 97%). The silylated cyanohydrin title compound was obtained as a mixture of two diastereomers in a 2:1 ratio: $^1$H NMR (400 MHz, CDCl$_3$): (major isomer) δ 7.54–7.50 (m, 1H), 7.42–7.38 (m, 3H), 4.14 (t, J=7.7 Hz, 1H), 3.78 (s, 3H), 3.01 (dd, J=13.3, 7.5 Hz, 1H), 2.79 (dd, J=13.3, 7.5 Hz, 1H), 0.26 (s, 9H); (minor isomer) 67.59–7.55 (m, 1H), 7.48–7.44 (m, 3H), 4.29 (t, J=7.5 Hz, 1H), 3.78 (s, 3H), 3.03 (dd, J=13.7, 7.5 Hz, 1H), 2.70 (dd, J=13.7, 7.5 Hz, 1H), 0.14 (s, 9H); $^{13}$C NMR (100 MHz, CDCl$_3$): (unassigned) δ 172.3, 172.0, 142.3, 142.1, 140.1, 138.8, 130.8, 130.5, 129.1, 128.9, 125.8, 125.6, 124.7, 124.3, 120.8, 120.6, 75.4, 75.3, 52.7, 52.7, 47.4, 46.8, 45.6, 45.3, 1.4, 1.3; IR (neat, cm$^{-1}$): 2956, 1739, 1477, 1436, 1253, 1197, 1169, 1135, 1092, 1033, 1011, 880, 843, 756, 623; Anal. Calcd for C$_{15}$H$_{19}$NO$_3$Si: C, 62.25; H, 6.62; N, 4.84; Found: C, 62.20; H, 6.53; N, 4.92.

C) 3-Aminomethyl-indan-1-carboxylic acid methyl ester

To a solution of 5.79 g of 3-cyano-3-trimethylsilanyloxy-indan-1-carboxylic acid methyl ester (20.0 mmol, 1.0 equivalent) in 25 mL of methanol was added 5.71 g of p-toluenesulfonic acid monohydrate (30.0 mmol, 1.5 equivalent). The solution was stirred for 15 minutes and then 4.21 g of 20% palladium hydroxide on carbon, 50% wet by weight, (3.00 mmol, 0.15 equivalent) was added. The reaction mixture was subjected to hydrogenolysis at 50 psi of hydrogen over 24 hours. After this time, the reaction mixture was filtered through Celite and typically used-filtrate in the next step (Example 60D). The isolation of the title compound was conducted as follows: the filtrate was concentrated in vacuo; the residue was partitioned between 30 mL of methylene chloride and 20 mL of a saturated aqueous solution of sodium carbonate; the aqueous layer was extracted with 15 mL of methylene chloride; the combined aqueous layers were washed with 40 mL of a saturated aqueous solution of sodium chloride; the organic solution was dried over anhydrous sodium sulfate and concentrated to afford the title compound as an oil (3.65 g, 89%) with approximately a 10:1 ratio of diastereomers; (major diastereomer) $^1$H NMR (400 MHz, CDCl$_3$): δ 7.43 (dd, J=6.9, 1.6 Hz, 1H), 7.29–7.25 (m, 3H), 4.09 (t, J=8.1 Hz, 1H), 3.80 (s, 3H), 3.31–3.24 (m, 1H), 3.14 (dd, J=12.8, 4.7 Hz, 1H), 2.98 (dd, J=12.8, 7.3 Hz, 1H), 2.62–2.52 (m, 1H), 2.31–2.42 (m, 1H), 1.3 (bs, 2H).

D) 9-Oxo-10-aza-tricyclo[6.3.1.0$^{2,7}$]dodeca-2(7),3,5-triene

To a solution of 3-aminomethyl-indan-1-carboxylic acid methyl ester (assume 20.0 mmol, 1 equivalent) in 50 mL of methanol (this was the crude reaction mixture from the prior step, Example 60C) was added 3.84 g of sodium tert-butoxide (40.0 mmol, 2.0 equivalent). The reaction mixture was heated to a reflux for 2 hours. The reaction was cooled to room temperature and concentrated in vacuo. The residue was partitioned between 60 mL of ethyl acetate and 40 mL of 5% aqueous solution of sodium bicarbonate. The aqueous layer was extracted twice more with 50 mL of ethyl acetate. The combined organic layers were dried over anhydrous sodium sulfate and concentrated to provide a solid material. Recrystallization of the solid from 10 mL of toluene provided white crystals of the title compound (1.78 g, 51%). mp=172–173° C.;. $^1$H NMR (400 MHz, CDCl$_3$): δ 7.33 (d, J=7.6 Hz, 1H), 7.31 (d, J=7.6 Hz, 1H), 7.22 (t, J=7.6 Hz, 1H), 7.18 (t, J=7.6 Hz, 1H), 5.62 (s, 1H), 3.68 (dd, J=11.2, 4.1 Hz, 1H), 3.55 (d, J=3.7 Hz, 1H), 3.43–3.37 (m, 1H), 3.18 (d, J=11.2 Hz, 1H), 2.52–2.45 (m, 1H), 2.32 (d, J=11.2 Hz, 1H); $^{13}$C NMR (100 MHz, CDCl$_3$): δ 173.6, 144.7, 144.6, 128.0, 127.7, 123.2, 122.9, 49.3, 47.9, 39.1, 38.4; IR (neat, cm$^{-1}$): 3218, 2949, 2872, 1666, 1485, 1459, 1400, 1328, 1303, 1288, 1250, 1215, 1122, 1104, 1045, 1004, 946, 910, 756, 730, 643, 613; Anal. Calcd for C$_{11}$H$_{21}$NO: C, 76.28; H, 6.40; N, 8.09; Found: C, 75.94; H, 6.27; N, 7.99.

E) 10-Aza-tricyclo[6.3.1.0$^{2,7}$]dodeca-2(7),3,5-triene tosylate

To a solution of 1.38 g of 9-oxo-10-aza-tricyclo[6.3.1.0$^{2,7}$]dodeca-2(7),3,5-triene (8.00 mmol, 1 equivalent) in 8 mL of tetrahydrofuran was added 603 mg of sodium borohydride (16.0 mmol, 2.0 equivalent) followed by slow addition of 2.77 mL of boron trifluoride diethyl etherate (21.6 mmol, 2.7 equivalent). Once the effervescence subsided, the reaction mixture was heated to 50° C. for 5 hours. The reaction was then cooled to room temperature for addition of 10 mL of methanol (added dropwise at first) and 0.125 mL of concentrated hydrochloric acid. Heating was resumed at a reflux for 12 hours. The reaction mixture was then cooled to room temperature and concentrated in vacuo. The residue was diluted with 20 mL of 20% aqueous sodium hydroxide followed by 30 mL of methyl-tert-butyl ether. The mixture was stirred for 30 minutes and then the aqueous layer was extracted with another 30 mL of methyl-tert-butyl ether. The combined organic layers were washed with 40 mL of a saturated aqueous sodium chloride solution and dried over anhydrous sodium sulfate. After concentrating in vacuo, 1.67 g of p-toluenesulfonic acid monohydrate (8.80 mmol, 1.1 equivalent) was added with 20 mL of isopropanol. The solution was heated until homogeneous and then allowed to gradually cool to room temperature with stirring. White crystals of the title compound formed and were collected by filtration (2.17 g, 81%). mp: 207–208° C.; $^1$H NMR (400 MHz, CD$_3$OD): δ 7.69 (d, J=7.9 Hz, 2H), 7.43–7.32 (m, 4H), 7.23 (d, J=7.9 Hz, 2H), 3.37 (d, J=11.2 Hz, 4H), 3.30 (bs, 2H), 3.15 (d, J=12.4 Hz, 2H), 2.36 (s, 3H), 2.40–2.35 (m, 1H), 2.08 (d, J=11.2 Hz, 1H); $^{13}$C NMR (100 MHz, CD$_3$OD): δ 140.8, 140.5, 139.1, 127.2, 127.2, 124.3, 122.3, 45.1, 39.7, 37.3, 18.7; IR (KBr, cm$^{-1}$): 3438, 3021, 2958, 2822, 2758, 2719, 2683, 2611, 2424, 1925, 1606, 1497, 1473, 1428, 1339, 1302, 1259, 1228, 1219, 1176, 1160, 1137, 1122, 1087, 1078, 945, 914, 876, 847, 829, 818, 801, 710, 492; Anal. Calcd for C$_{18}$H$_{21}$NO$_3$S: C, 65.23; H, 6.39; N, 4.23; Found: C, 65.05; H, 6.48; N, 4.26.

The invention claimed is:

1. A compound selected from the group consisting of:
(+)-5,13-diazatetracyclo[9.3.1.0$^{2,10}$.0$^{4,8}$]pentadeca-2,4 (8),9-trien-6-one;
(+)-6-oxo-5-oxa-7,13-diazatetracyclo[9.3.1.0$^{2,10}$.0$^{4,8}$] pentadeca-2(10),3,8-triene;
(+)-2-fluoro-N-(4-hydroxy-10-aza-tricyclo[6.3.1.0$^{2,7}$] dodeca-2(7),3,5-trien-5-yl)-benzamide;
(+)-6-methyl-5-oxo-6,13-diazatetracyclo[9.3.1.0$^{2,10}$.0$^{4,8}$] pentadeca-2(10),3,8-triene;
(+)-5-oxo-6,13-diazatetracyclo[9.3.1.0$^{2,10}$.0$^{4,8}$]pentadeca-2(10),3,8-triene;
(+)-7-dimethylamino-5-thia-5-dioxo-6,13-diazatetracyclo[9.3.1.0$^{2,10}$.0$^{4,8}$]pentadeca-2(10),3,6,8-tetraene;
(+)-5-oxa-7-methyl-6-oxo-7,13-diazatetracyclo[9.3.1. 0$^{2,10}$.0$^{4,8}$]pentadeca-2(10),3,8-triene;
(+)-1-(10-azatricyclo[6.3.1.0$^{2,7}$]dodeca-2(7),3,5-trien-4-yl)-1-ethanone;
(+)-6-methyl-5-thia-7,13-diazatetracyclo[9.3.1.0$^{2,10}$.0$^{4,8}$] pentadeca-2(10),3,6,8-tetraene;
(+)-6-methyl-7-propyl-5,7,13-triazatetracyclo[9.3.1.0$^{2,10}$.0$^{4,8}$]pentadeca-2(10),3,5,8-tetraene;
(+)-7-methyl-5,7,13-triazatetracyclo[9.3.1.0$^{2,10}$.0$^{4,8}$]pentadeca-2(10),3,5,8-tetraene;
(+)-6,7-dimethyl-5,7,13-triazatetracyclo[9.3.1.0$^{2,10}$.0$^{4,8}$] pentadeca-2(10),3,5,8-tetraene;
(+)-7-propyl-5,7,13-triazatetracyclo[9.3.1.0$^{2,10}$.0$^{4,8}$]pentadeca-2(10),3,5,8-tetraene;
(+)-7-butyl-5,7,13-triazatetracyclo[9.3.1.0$^{2,10}$.0$^{4,8}$]pentadeca-2(10),3,5,8-tetraene;
(+)-6-methyl-7-isobutyl-5,7,13-triazatetracyclo[9.3.1.0$^{2,10}$.0$^{4,8}$]pentadeca-2(10),3,5,8-tetraene;
(+)-7-phenyl-5,7,13-triazatetracyclo[9.3.1.0$^{2,10}$.0$^{4,8}$]pentadeca-2(10),3,5,8-tetraene;
(+)-6-methyl-7-phenyl-5,7,13-triazatetracyclo[9.3.1. 0$^{2,10}$.0$^{4,8}$]pentadeca-2(10),3,5,8-tetraene;
(+)-7-neopentyl-5,7,13-triazatetracyclo[9.3.1.0$^{2,10}$.0$^{4,8}$] pentadeca-2(10),3,5,8-tetraene;
(+)-6-methyl-7-neopentyl-5,7,13-triazatetracyclo [9.3.1.0$^{2,10}$.0$^{4,8}$]pentadeca-2(10),3,5,8-tetraene;
(+)-5-oxa-7,13-diazatetracyclo[9.3.1.0$^{2,10}$.0$^{4,8}$]pentadeca-2(10),3,6,8-tetraene;
(+)-6-methyl-5-oxa-7,13-diazatetracyclo[9.3.1.0$^{2,10}$.0$^{4,8}$] pentadeca-2(10),3,6,8-tetraene;
(+)-7-methyl-5-oxa-6,13-diazatetracyclo[9.3.1.0$^{2,10}$.0$^{4,8}$] pentadeca-2,4(8),6,9-tetraene;
and pharmaceutically acceptable salts thereof.

2. A pharmaceutical composition for use in reducing nicotine addiction or aiding In the cessation or lessening of tobacco use in a mammal, comprising an amount of a compound according to claim 1 that is effective in reducing nicotine addiction or aiding In the cessation or lessening of tobacco use and a pharmaceutically acceptable carrier.

3. A method for reducing nicotine addiction or aiding in the cessation or lessening of tobacco use in a mammal, comprising administering to said mammal an amount of a compound according to claim 1 that is effective in reducing nicotine addiction or aiding in the cessation or lessening of tobacco use.

4. A method for treating a disorder or condition selected from inflammatory bowel disease, ulcerative colitis, pyoderma gangrenosum, Crohn's disease, irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis, cognitive dysfunction, hypertension, bulimia, anorexia, obesity, cardiac arrythmias, gastric acid hypersecretion, ulcers, pheochromocytoma, progressive supranuclear palsy; chemical dependencies and addictions; dependencies on, or addictions to, nicotine, tobacco products, alcohol, benzodiazepines, barbiturates, opioids or cocaine; headache, migraine, stroke, traumatic brain injury, obsessive-compulsive disorder, psychosis, Huntington's chorea, tardive dyskinesia, hyperkinesia, dyslexia, schizophrenia, multi-infarct dementia, age related cognitive decline, epilepsy, including petit mal absence epilepsy, senile dementia of the Alzheimer's type, Parkinson's disease, attention deficit hyperactivity disorder and Tourette's Syndrome in a mammal, comprising administering to a mammal in need of such treatment an amount of a compound according to claim 1 that is effective in treating such disorder or condition.

5. A method for treating attention deficit hyperactivity disorder in a mammal, comprising administering to said mammal an amount of a compound according to claim 1 that is effective in attention deficit hyperactivity disorder.

6. A method for treating Tourette's Syndrome in a mammal, comprising administering to said mammal an amount of a compound according to claim 1 that is effective in treating Tourette's Syndrome.

7. A compound selected from the group consisting of:
(+)-4-methyl-10-aza-tricyclo[6.3.1.0$^{2,7}$]dodeca-2(7),3,5-triene;
(+)-4-nitro-10-azatricyclo[6.3.1.0$^{2,7}$]dodeca-2(7),3,5-triene;
(+)-4-amino-10-azatricyclo[6.3.1.0$^{2,7}$]dodeca-2(7),3,5-triene;
(+)-N$^1$-[10-azatricyclo[6.3.1.0$^{2,7}$]dodeca-2(7),3,5-trien-4-yl]acetamide;
(+)-4-chloro-10-azatricyclo[6.3.1.0$^{2,7}$]dodeca-2(7),3,5-triene;
(+)-3-(10-azatricyclo[6.3.1.0$^{2,7}$]dodeca-2(7),3,5-trien-4-yl)-5-methyl-1,2,4-oxadiazole;
(+)-10-azatricyclo[6.3.1.0$^{2,7}$]dodeca-2(7),3,5-trien-4-ol;
(+)-N$^4$,N$^4$-dimethyl-10-azatricyclo[6.3.1.0$^{2,7}$]dodeca-2 (7),3,5-triene-4-sulfonamide;
(+)-4-(1-pyrrolidinylsulfonyl)-10-azatricyclo[6.3.1.0$^{2,7}$] dodeca-2(7),3,5-triene;
(+)-5-fluoro-10-aza-tricyclo[6.3.1.0$^{2,7}$]dodeca-2(7),3,5-triene-4-carbonitrile;
(+)-4-ethynyl-5-fluoro-10-aza-tricyclo[6.3.1.0$^{2,7}$]dodeca-2(7),3,5-triene;
(+)-5-ethynyl-10-aza-tricyclo[6.3.1.0$^{2,7}$]dodeca-2(7),3,5-triene-4-carbonitrile;
(+)-5-chloro-10-aza-tricyclo[6.3.1.0$^{2,7}$]dodeca-2(7),3,5-triene-4-carbonitrile;
(+)-4-ethynyl-5-chloro-10-aza-tricyclo[6.3.1.0$^{2,7}$] dodeca-2(7),3,5-triene;
(+)-4-fluoro-5-trifluoromethyl-10-aza-tricyclo[6.3.1.0$^{2,7}$] dodeca-2(7),3,5-triene;
(+)-4-chloro-5-trifluoromethyl-10-aza-tricyclo[6.3.1.0$^{2,7}$] dodeca-2(7),3,5-triene;

(+)-5-trifluoromethyl-10-aza-tricyclo[6.3.1.0$^{2,7}$]dodeca-2 (7),3,5-triene-4-carbonitrile;

(+)-4-ethynyl-5-trifluoromethyl-10-aza-tricyclo[6.3.1. 0$^{2,7}$]dodeca-2(7),3,5-triene;

and pharmaceutically acceptable salts thereof.

8. A pharmaceutical composition for use in reducing nicotine addiction or aiding in the cessation or lessening of tobacco use in a mammal, comprising an amount of a compound according to claim 7 that is effective in reducing nicotine addiction or aiding in the cessation or lessening of tobacco use and a pharmaceutically acceptable carrier.

9. A method for reducing nicotine addiction or aiding in the cessation or lessening of tobacco use in a mammal, comprising administering to said mammal an amount of a compound according to claim 7 that is effective in reducing nicotine addiction or aiding in the cessation or lessening of tobacco use.

10. A method for treating a disorder or condition selected from inflammatory bowel disease, ulcerative colitis, pyoderma gangrenosum, Crohn's disease, irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis, cognitive dysfunction, hypertension, bulimia, anorexia, obesity, cardiac arrythmias, gastric acid hypersecretion, ulcers, pheochromocytoma, progressive supranuclear palsy; chemical dependencies and addictions; dependencies on, or addictions to, nicotine, tobacco products, alcohol, benzodiazepines, barbiturates, opioids or cocaine; headache, migraine, stroke, traumatic brain injury, obsessive-compulsive disorder, psychosis, Huntington's chorea, tardive dyskinesia, hyperkinesia, dyslexia, schizophrenia, multi-infarct dementia, age related cognitive decline, epilepsy, including petit mal absence epilepsy, senile dementia of the Alzheimer's type, Parkinson's disease, attention deficit hyperactivity disorder and Tourette's Syndrome in a mammal, comprising administering to a mammal in need of such treatment an amount of a compound according to claim 7 that is effective in treating such disorder or condition.

11. A method for treating attention deficit hyperactivity disorder in a mammal, comprising administering to said mammal an amount of a compound according to claim 7 that is effective in attention deficit hyperactivity disorder.

12. A method for treating Tourette's Syndrome in a mammal, comprising administering to said mammal an amount of a compound according to claim 7 that is effective in treating Tourette's Syndrome.

13. A compound selected from the group consisting of:
(+)-3-trifluoromethyl-10-aza-tricyclo[6.3.1.0$^{2,7}$]dodeca-2 (7),3,5-triene;
(+)-4-trifluoromethyl-10-aza-tricyclo[6.3.1.0$^{2,7}$]dodeca-2 (7),3,5-triene;
(+)-3-fluoro-10-aza-tricyclo[6.3.1.0$^{2,7}$]dodeca-2(7),3,5-triene;
(+)-10-azatricyclo[6.3.1.0$^{2,7}$]dodeca-2(7),3,5-trien-4-yl cyanide;
(+)-4-fluoro-10-aza-tricyclo[6.3.1.0$^{2,7}$]dodeca-2(7),3,5-triene;
and pharmaceutically acceptable salts thereof.

14. A pharmaceutical composition for use in reducing nicotine addiction or aiding in the cessation or lessening of tobacco use in a mammal, comprising an amount of a compound according to claim 13 that is effective in reducing nicotine addiction or aiding in the cessation or lessening of tobacco use and a pharmaceutically acceptable carrier.

15. A method for reducing nicotine addiction or aiding in the cessation or lessening of tobacco use in a mammal, comprising administering to said mammal an amount of a compound according to claim 13 that is effective in reducing nicotine addiction or aiding in the cessation or lessening of tobacco use.

16. A method for treating a disorder or condition selected from inflammatory bowel disease, ulcerative colitis, pyoderma gangrenosum, Crohn's disease, irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis, cognitive dysfunction, hypertension, bulimia, anorexia, obesity, cardiac arrythmias, gastric acid hypersecretion, ulcers, pheochromocytoma, progressive supranuclear palsy; chemical dependencies and addictions; dependencies on, or addictions to, nicotine, tobacco products, alcohol, benzodiazepines, barbiturates, opioids or cocaine; headache, migraine, stroke, traumatic brain injury, obsessive-compulsive disorder, psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type, Parkinson's disease, attention deficit hyperactivity disorder and Tourette's Syndrome in a mammal, comprising administering to a mammal in need of such treatment an amount of a compound according to claim 13 that is effective in treating such disorder or condition.

17. A method for treating attention deficit hyperactivity disorder in a mammal, comprising administering to said mammal an amount of a compound according to claim 13 that is effective in attention deficit hyperactivity disorder.

18. A method for treating Tourette's Syndrome in a mammal, comprising administering to said mammal an amount of a compound according to claim 13 that is effective in treating Tourette's Syndrome.

19. A compound selected from the group consisting of:
(+)-5,14-diazatetracyclo[10.3.1.0$^{2,11}$.0$^{4,9}$]hexadeca-2 (11),3,5,7,9-pentaene;
(+)-6-methyl-5,14-diazatetracyclo[10.3.1.0$^{2,11}$.0$^{4,9}$]hexadeca-2(11),3,5,7,9-pentaene;
(+)-7-methyl-5,14-diazatetracyclo[10.3.1.0$^{2,11}$.0$^{4,9}$]hexadeca-2(11),3,5,7,9-pentaene;
(+)-7-ethyl-5,14-diazatetracyclo[10.3.1.0$^{2,11}$.0$^{4,9}$]hexadeca-2(11),3,5,7,9-pentaene;
(+)-8-methyl-5,14-diazatetracyclo[10.3.1.0$^{2,11}$.0$^{4,9}$]hexadeca-2(11),3,5,7,9-pentaene;
(+)-5,14-diazatetracyclo[10.3.1.0$^{2,11}$.0$^{4,9}$]hexadeca-2 (11),3,7,9-tetraen-6-one;
(+)-6-chloro-5,14-diazatetracyclo[10.3.1.0$^{2,11}$.0$^{4,9}$]hexadeca-2(11),3,5,7,9-pentaene;
(+)-6-methoxy-5,14-diazatetracyclo[10.3.1.0$^{2,11}$.0$^{4,9}$]hexadeca-2(11),3,5,7,9-pentaene;
(+)-6-chloro-10-fluoro-5,14-diazatetracyclo[10.3.1.0$^{2,11}$.0$^{4,9}$]hexadeca-2(11),3,5,7,9-pentaene;
(+)-6-chloro-3-fluoro-5,14-diazatetracyclo[10.3.1.0$^{2,11}$.0$^{4,9}$]hexadeca-2(11),3,5,7,9-pentaene;
and pharmaceutically acceptable salts thereof.

20. A pharmaceutical composition for use in reducing nicotine addiction or aiding in the cessation or lessening of tobacco use in a mammal, comprising an amount of a compound according to claim 19 that is effective in reducing nicotine addiction or aiding in the cessation or lessening of tobacco use and a pharmaceutically acceptable carrier.

21. A method for reducing nicotine addiction or aiding in the cessation or lessening of tobacco use in a mammal, comprising administering to said mammal an amount of a compound according to claim 19 that is effective in reducing nicotine addiction or aiding in the cessation or lessening of tobacco use.

22. A method for treating a disorder or condition selected from inflammatory bowel disease, ulcerative colitis, pyoderma gangrenosum, Crohn's disease, irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis, cognitive dysfunction, hypertension, bulimia, anorexia, obesity, cardiac arrythmias, gastric acid hypersecretion, ulcers, pheochromocytoma, progressive supranuclear palsy; chemical dependencies and addictions; dependencies on, or addictions to, nicotine, tobacco products, alcohol, benzodiazepines, barbiturates, opioids or cocaine; headache, migraine, stroke, traumatic brain injury, obsessive-compulsive disorder, psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type, Parkinson's disease, attention deficit hyperactivity disorder and Tourette's Syndrome in a mammal, comprising administering to a mammal in need of such treatment an amount of a compound according to claim 19 that is effective in treating such disorder or condition.

23. A method for treating attention deficit hyperactivity disorder in a mammal, comprising administering to said mammal an amount of a compound according to claim 19 that is effective in attention deficit hyperactivity disorder.

24. A method for treating Tourette's Syndrome in a mammal, comprising administering to said mammal an amount of a compound according to claim 19 that is effective in treating Tourette's Syndrome.

* * * * *